(12) United States Patent
Lombardi Borgia et al.

(10) Patent No.: US 9,408,850 B2
(45) Date of Patent: Aug. 9, 2016

(54) SUBSTITUTED INDAZOLE DERIVATIVES ACTIVE AS KINASE INHIBITORS

(75) Inventors: Andrea Lombardi Borgia, Paullo (IT); Marina Ciomei, Corsico (IT); Daniele Donati, Nerviano (IT); Marcella Nesi, Saronno (IT)

(73) Assignee: NERVIANO MEDICAL SCIENCES S.R.L., Nerviano (MI) (IT)

( * ) Notice: Subject to any disclaimer, the term of this patent is extended or adjusted under 35 U.S.C. 154(b) by 133 days.

(21) Appl. No.: 14/116,512

(22) PCT Filed: May 7, 2012

(86) PCT No.: PCT/EP2012/058389
§ 371 (c)(1),
(2), (4) Date: Nov. 8, 2013

(87) PCT Pub. No.: WO2012/152763
PCT Pub. Date: Nov. 15, 2012

(65) Prior Publication Data
US 2014/0080807 A1    Mar. 20, 2014

(30) Foreign Application Priority Data
May 12, 2011  (EP) .................................... 11165882

(51) Int. Cl.
| | | |
|---|---|---|
| C07D 231/56 | (2006.01) | |
| C07D 401/12 | (2006.01) | |
| C07D 295/185 | (2006.01) | |
| C07D 405/12 | (2006.01) | |
| C07D 403/12 | (2006.01) | |
| A61K 31/496 | (2006.01) | |
| A61K 31/416 | (2006.01) | |
| A61K 31/5377 | (2006.01) | |
| C07D 401/14 | (2006.01) | |
| C07D 403/14 | (2006.01) | |
| A61K 31/454 | (2006.01) | |
| A61K 45/06 | (2006.01) | |
| C07D 295/155 | (2006.01) | |

(52) U.S. Cl.
CPC .......... *A61K 31/5377* (2013.01); *A61K 31/416* (2013.01); *A61K 31/454* (2013.01); *A61K 31/496* (2013.01); *A61K 45/06* (2013.01); *C07D 231/56* (2013.01); *C07D 295/155* (2013.01); *C07D 295/185* (2013.01); *C07D 401/12* (2013.01); *C07D 401/14* (2013.01); *C07D 403/12* (2013.01); *C07D 403/14* (2013.01); *C07D 405/12* (2013.01)

(58) Field of Classification Search
None
See application file for complete search history.

(56) References Cited

FOREIGN PATENT DOCUMENTS

| WO | WO 03/028720 A1 | 4/2003 |
| WO | WO 2005/073224 A2 | 8/2005 |
| WO | WO 2005/085206 A1 | 9/2005 |
| WO | WO 2008/003396 A1 | 1/2008 |
| WO | WO 2010/069966 A1 | 6/2010 |

OTHER PUBLICATIONS

Antonescu C.R., "The GIST Paradigm: Lessons for Other Kinase-Driven Cancers", Journal of Pathology 223:251-261 (2011).
Cohen P., "The Development and Therapeutic Potential of Protein Kinase Inhibitors", Current Opinion in Chemical Biology 3:459-465 (1999).
Cohen P., "Protein Kinases—The Major Drug Targets of the Twenty-First Century?", Nature Reviews—Drug Discovery 1:309-315 (Apr. 2002).
Colombo M. et al., "A Fully Automated Method for Accurate Mass Determination Using High-Performance Liquid Chromatography with a Quadrupole/Orthogonal Acceleration Time-of-Flight Mass Spectrometer", Rapid Communications in Mass Spectrometry 18:511-517 (2004).
Curtin J.A. et al., "Somatic Activation of KIT in Distinct Subtypes of Melanoma", Journal of Clinical Oncology 24(26):4340-4346 (Sep. 10, 2006).
Horiike S. et al., "Tandem Duplications of the FLT3 Receptor Gene are Associated with Leukemic Transformation of Myelodysplasia", Leukemia 11:1442-1446 (1997).
Hunter T., "Signaling-2000 and Beyond", Cell 100:113-127 (Jan. 7, 2000).
Lim K-H et al., "KIT and Mastocytosis", Acta Haematol 119:194-198 (2008).
Malaise M. et al., "Clinical Implications of C-Kit Mutations in Acute Myelogenous Leukemia", Current Hematologic Malignancy Reports 4:77-82 (2009).
Masson K. et al., "Oncogenic Signaling from the Hematopoietic Growth Factor Receptors C-Kit and Flt3", Cellular Signalling 21:1717-1726 (2009).
Micke P. et al., "Characterization of C-Kit Expression in Small Cell Lung Cancer: Prognostic and Therapeutic Implications", Clinical Cancer Research 9:188-194 (Jan. 2003).
Morris P.G. et al., "Novel Targeted Agents for Platelet-Derived Growth Factor Receptor and C-Kit in Malignant Gliomas", Targ Oncol 5:193-200 (2010).
Murakami T. et al., "New KIT Mutations in Patients with Piebaldism", Journal of Dermatological Science 35:29-33 (2004).
Nakao M. et al., "Internal Tandem Duplication of the Flt3 Gene Found in Acute Myeloid Leukemia", Leukemia 10:1911-1918 (1996).

(Continued)

*Primary Examiner* — Kamal Saeed
(74) *Attorney, Agent, or Firm* — Scully, Scott, Murphy & Presser, P.C.

(57) ABSTRACT

The present invention relates to substituted indazole compounds which modulate the activity of protein kinases and are therefore useful in treating diseases caused by degulated protein kinase activity, like cancer. The present invention also provides methods for preparing these compounds, pharmaceutical compositions comprising these compounds, and methods of treating diseases utilizing such these compounds or the pharmaceutical compositions containing them.

6 Claims, No Drawings

(56) References Cited

OTHER PUBLICATIONS

Nikolaou M. et al., "Kit Expression in Male Germ Cell Tumors", Anticancer Research 27:1685-1688 (2007).

Pittoni P. et al., "Tumor-Intrinsic and -Extrinsic Roles of C-Kit: Mast Cells as the Primary Off-Target of Tyrosine Kinase Inhibitors", Oncogene 30:757-769 (2011).

Strobel P. et al., "Thymoma and Thymic Carcinoma-Molecular Pathology and Targeted Therapy", Journal of Thoracic Oncology 5(10), Supplement 4:S286-S290 (Oct. 2010).

Velculescu V.E., "Defining the Blueprint of the Cancer Genome", Carcinogensis 29(6):1087-1091 (2008).

Vila L. et al., "Identification of C-Kit Gene Mutations in Primary Adenoid Cystic Carcinoma of the Salivary Gland", Modern Pathology 22:1296-1302 (2009).

International Search Report dated Jun. 19, 2012 issued in PCT/EP2012/058389.

SEQUENCE LISTING

<160> NUMBER OF SEQ ID NOS: 2

<210> SEQ ID NO 1
<211> LENGTH: 25
<212> TYPE: PRT
<213> ORGANISM: Artificial
<220> FEATURE:
<223> OTHER INFORMATION: peptide substrate

<400> SEQUENCE: 1

Gly Gly Lys Lys Lys Val Ser Arg Ser Gly Leu Tyr Arg Ser Pro Ser
1               5                   10                  15

Met Pro Glu Asn Leu Asn Arg Pro Arg
            20                  25

<210> SEQ ID NO 2
<211> LENGTH: 31
<212> TYPE: PRT
<213> ORGANISM: Artificial
<220> FEATURE:
<223> OTHER INFORMATION: Peptide substrate

```
<400> SEQUENCE: 2

Lys Val Val Glu Glu Ile Asn Gly Asn Asn Tyr Val Tyr Ile Asp Pro
1               5                   10                  15

Thr Gln Leu Pro Tyr Asp His Lys Trp Glu Phe Pro Arg Asn Arg
            20                  25                  30
```

SUBSTITUTED INDAZOLE DERIVATIVES ACTIVE AS KINASE INHIBITORS

INCORPORATION BY REFERENCE OF SEQUENCE LISTING

The Sequence Listing in an ASCII text file, named as 30545_SequenceList.txt of 1 KB, created on Oct. 28, 2013, and submitted to the United States Patent and Trademark Office via EFS-Web, is incorporated herein by reference.

The present invention relates to certain substituted indazole compounds, which modulate the activity of protein kinases. The compounds of this invention are therefore useful in treating diseases caused by deregulated protein kinase activity. The present invention also provides methods for preparing these compounds, pharmaceutical compositions comprising these compounds, and methods of treating diseases utilizing pharmaceutical compositions comprising these compounds.

The malfunctioning of protein kinases (PKs) is the hallmark of numerous diseases. A large share of the oncogenes and proto-oncogenes involved in human cancers encode for PKs. The enhanced activities of PKs are also implicated in many non-malignant diseases, such as benign prostate hyperplasia, familial adenomatosis, polyposis, neuro-fibromatosis, psoriasis, vascular smooth cell proliferation associated with atherosclerosis, pulmonary fibrosis, arthritis glomerulonephritis and post-surgical stenosis and restenosis.

PKs are also implicated in inflammatory conditions and in the multiplication of viruses and parasites. PKs may also play a major role in the pathogenesis and development of neurodegenerative disorders.

For a general reference to PKs malfunctioning or deregulation see, for instance, Current Opinion in Chemical Biology (1999) 3, 459-465; Cell (2000) 100, 113-127; Nature Rev. Drug Discov. (2002) 1, 309-315; and Carcinogenesis (2008) 29, 1087-191.

A subset of PK is a group of membrane receptors with intrinsic protein-tyrosine kinase activity (RPTK). Upon binding of growth factors, RPTKs become activated and phosphorylate themselves and a series of substrates in the cytoplasm. Through this mechanism, they can transduce intracellular signallings for proliferation, differentiation or other biological changes. Structural abnormalities, over-expression and activation of RTPKs are frequently observed in human tumors, suggesting that constitutive ignition of the signal transduction leading to cell proliferation can result in malignant transformation.

FMS-like tyrosine kinase 3 (FLT3) and KIT are both members of the PDGFR family class III receptor tyrosine kinases characterized by an extracellular domain with 5 immunoglobulin-like loops, a transmembrane region and a cytoplasmic domain containing not only the kinase domain (divided in two regions) but also an autoinhibitory juxtamembrane (JM) domain that docks with the kinase domain to stabilize a catalytically inactive conformation.

Normally, FLT3 has a crucial role in normal haematopoiesis and its expression is restricted to CD34+ hematopoietic stem/progenitor cells, brain, placenta, and gonads. Activation of FLT3 by FLT3-ligand promotes the normal growth of early progenitor cells.

In acute leukemia, mutations of the FLT3 gene have been found to be one of the most common acquired genetic lesions. FLT3 mutations can be detected in 30% of acute myeloid leukemia (AML) patients (Nakao M, et al. Leukemia. 1996 December; 10(12): 1911-8), and also in 5-10% of patients with myelodisplastic syndrome (Horiike S, et al. Leukemia. 1997 September; 11(9): 1442-6). There are two frequent types of somatic FLT3 genetic mutations: internal tandem duplications (ITDs) in the JM domain and point mutations in the activation loop of the tyrosine kinase domain (TKD). ITD mutations are any elongation or shortening of the JM domain of FLT3 due to additions or deletions of amino acids that result in the constitutive activation of FLT3. The presence of FLT3/ITD mutations is associated with a poor clinical outcome in both pediatric and adult patients with AML. Point mutations in the activation loop of the kinase domain (FLT3/TKD) involve the aspartic acid, D835 residue, which leads to an activated configuration and transformation of myeloid cells. D835 mutations are missense mutations that result in substitution of tyrosine, histidine, valine, glutamic acid or asparagine for aspartatic acid at amino acid 835 of FLT3. These mutations have been reported in 7% of patients with AML. TKD mutations, unlike ITD mutations, have not been shown to have any prognostic significance in AML patients. Both types of FLT3 mutation cause ligand-independent activation of the receptor and activation of downstream signalling pathways. Mutant FLT3 provides survival advantage to leukemic cells because it causes activation of three major intracellular signalling pathways: PI3K/AKT; RAS/RAF/MAPK and JAK/STAT (Masson K, Rönnstrand L. Cell Signal. 2009 December; 21(12): 1717-26).

In conclusion, interfering with the FLT3 signalling likely represents a specific and effective way to block tumor cell proliferation in AML and possibly other indications.

KIT is normally activated by stem cell factor. Signalling by KIT plays an important role in erythropoiesis, lymphopoiesis, mast cell development and function, megakaryopoiesis, gametogenesis and melanogenesis. Hematopoietic stem cells, multipotent progenitors and common myeloid progenitors, but also early T lineage progenitors and thymocytes express high levels of KIT. In addition, mast cells, melanocytes in the skin, and interstitial cells of Cajal in the digestive tract express KIT (Pittoni P. et al. Oncogene 2011 Feb. 17; 30(7): 757-69).

KIT overexpression or mutations can lead to cancer. Mutations in this gene are frequently associated with gastrointestinal stromal tumors (GIST) (Antonescu C R. J Pathol. 2011; 223(2): 251-6). About 65-85% of GISTs have KIT mutations, divided into two categories: mutations of the receptor regulatory domains (extracellular and juxtamembrane) and mutation in the enzymatic domain. At diagnosis, the most frequent mutations, deletions and point mutations, affect JM domain. Extracellular domain mutations are the second most common mutations followed by tyrosine kinase domain mutations. Mutation of KIT have been identified also in melanoma (Curtin J A, JCO, 2006, 24 (26): 4340-4346), acute myeloid leukemia (Malaise M, Steinbach D, Corbacioglu S, Curr Hematol Malig Rep. 2009, 4(2): 77-82), and primary adenoid cystic carcinoma of the salivary gland (Vila L, Liu H, Al-Quran S Z, Coco D P, Dong H J, Liu C, Mod Pathol. 2009; 22(10): 1296-302). Overexpression is reported also in thymic carcinoma (Ströbel P, Hohenberger P, Marx A, J Thorac Oncol. 2010; 5 (10 Suppl 4): S286-90), glioma (Morris P G, Abrey L E. Target Oncol. 2010; 5(3):193-200), testicular seminoma (Nikolaou M. et al. Anticancer Res. 2007; 27(3B): 1685-8), and small cell lung cancers (SCLC) (Micke P, et al. Clin Cancer Res. 2003; 9(1): 188-94). Additional disorders are linked to KIT activation such as mast cell disease (Lim K H, Pardanani A, Tefferi A. Acta Haematol. 2008; 119(4):194-8) or piebaldism (Murakami T, et al. J Dermatol Sci. 2004 June; 35(1):29-33).

Based on the collection of data, KIT kinase activation appears to be the triggering factor for an important group of malignancies, both hematological and solid cancer diseases, thereby suggesting that it could represent a good therapeutic target for the treatment of these pathologies.

Several indazole derivatives useful for the therapy of a variety of diseases such as cancers, neurodegeneration and atherosclerosis have been disclosed in WO2003028720, WO2005085206, WO2008003396 and WO201069966 in the name respectively of Pharmacia Italia spa, Hoffmann La Roche AG, Merck GMBH and Nerviano Medical Sciences. Despite these developments, there is still a need for more effective agents.

We have now discovered that a series of indazoles are potent protein kinase inhibitors and are thus useful in anti-cancer therapy.

Accordingly, a first object of the present invention is to provide a substituted indazole compound represented by formula (I),

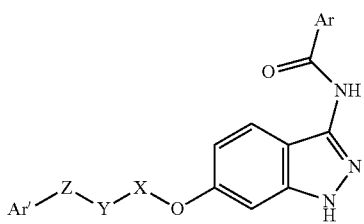

(I)

wherein:
Ar is a group selected from

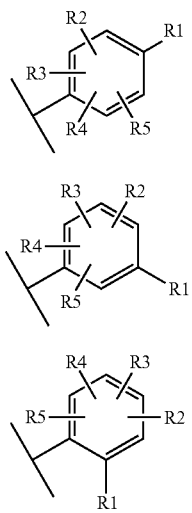

Ar1

Ar2

Ar3 wherein:
R1 is A, NR6R7, OR8, SO$_n$R9, COR10, nitro, cyano or an optionally substituted group selected from $C_3$-$C_6$ cycloalkyl, heterocyclyl and heteroaryl;

R2, R3, R4 and R5 are independently hydrogen, halogen, nitro, cyano, SO$_n$R9, COR10, NR11R12, OR13 or an optionally substituted group selected from straight or branched $C_1$-$C_6$ alkyl, straight or branched $C_2$-$C_6$ alkenyl, straight or branched $C_2$-$C_6$ alkynyl, $C_3$-$C_6$ cycloalkyl and heterocyclyl wherein:

A is a straight or branched $C_1$-$C_6$ alkyl substituted with a group selected from an optionally substituted heterocyclyl, an optionally substituted heteroaryl, SO$_n$R9, COR10, NR11R12 and OR13;

R6 is hydrogen or an optionally substituted group selected from straight or branched $C_1$-$C_6$ alkyl, straight or branched $C_2$-$C_6$ alkenyl, straight or branched $C_2$-$C_6$ alkynyl, $C_3$-$C_6$ cycloalkyl, heterocyclyl, aryl and heteroaryl;

R7 is hydrogen, SO$_n$R9, COR10, a substituted straight or branched $C_1$-$C_6$ alkyl or an optionally substituted group selected from straight or branched $C_2$-$C_6$ alkenyl, straight or branched $C_2$-$C_6$ alkynyl, $C_3$-$C_6$ cycloalkyl, heterocyclyl, aryl and heteroaryl or R6 and R7, taken together with the nitrogen atom to which they are bound, may form an optionally substituted heterocyclyl group;

R8 is hydrogen, A, COR10 or an optionally substituted group selected from straight or branched $C_2$-$C_6$ alkenyl, straight or branched $C_2$-$C_6$ alkynyl, $C_3$-$C_6$ cycloalkyl, heterocyclyl, aryl and heteroaryl, wherein A is as defined above;

R9 is NR11R12 or an optionally substituted group selected from straight or branched $C_1$-$C_6$ alkyl, straight or branched $C_2$-$C_6$ alkenyl, straight or branched $C_2$-$C_6$ alkynyl, $C_3$-$C_6$ cycloalkyl, heterocyclyl, aryl and heteroaryl;

R10 is hydrogen, NR11R12, OR13 or an optionally substituted group selected from straight or branched $C_1$-$C_6$ alkyl, straight or branched $C_2$-$C_6$ alkenyl, straight or branched $C_2$-$C_6$ alkynyl, $C_3$-$C_6$ cycloalkyl, heterocyclyl, aryl and heteroaryl;

R11 and R12 are independently hydrogen, SO$_n$R9, COR10 or an optionally substituted group selected from straight or branched $C_1$-$C_6$ alkyl, straight or branched $C_2$-$C_6$ alkenyl, straight or branched $C_2$-$C_6$ alkynyl, $C_3$-$C_6$ cycloalkyl, heterocyclyl, aryl and heteroaryl, wherein R9 and R10 are as defined above, or R11 and R12, taken together with the nitrogen atom to which they are bound, may form an optionally substituted heterocyclyl group;

R13 is hydrogen, COR10 or an optionally substituted group selected from straight or branched $C_1$-$C_6$ alkyl, straight or branched $C_2$-$C_6$ alkenyl, straight or branched $C_2$-$C_6$ alkynyl, $C_3$-$C_6$ cycloalkyl, heterocyclyl, aryl and heteroaryl, wherein R10 is as defined above;

n is 0, 1 or 2;
X is a bond or an optionally substituted group selected from straight or branched $C_1$-$C_6$ alkyl, heterocycly and aryl;

Y is a bond, oxygen, or an optionally substituted group selected from straight or branched $C_1$-$C_6$ alkyl, straight or branched $C_2$-$C_6$ alkenyl, straight or branched $C_2$-$C_6$ alkynyl, heterocyclyl and aryl;

Z is a bond, oxygen or an optionally substituted straight or branched $C_1$-$C_6$ alkyl;

Ar' is an optionally substituted aryl or an optionally substituted heteroaryl;

or a pharmaceutically acceptable salt thereof.

The present invention also provides methods of synthesizing the substituted indazole derivatives of formula (I) prepared through a process consisting of standard synthetic transformations and isomers, tautomers, hydrates, solvates, complexes, metabolites, prodrugs, carriers, N-oxides.

The present invention also provides a method of treating diseases caused by and/or associated with deregulated protein kinase activity, particularly ABL, ACK1, AKT1, ALK, AUR1, AUR2, BRK, BUB1, CDC7/DBF4, CDK2/CYCA, CHK1, CK2, EEF2K, EGFR1, EphA2, EphB4, ERK2, FAK, FGFR1, FLT3, GSK3beta, Haspin, IGFR1, IKK2, IR, JAK1, JAK2, JAK3, KIT, LCK, LYN, MAPKAPK2, MELK, MET, MNK2, MPS1, MST4, NEK6, NIM1, P38alpha, PAK4, PDGFR, PDK1, PERK, PIM1, PIM2, PKAalpha, PKCbeta, PLK1, RET, ROS1, SULU1, Syk, TLK2, TRKA, TYK, VEGFR2, VEGFR3 or ZAP70 activity, more particularly FLT3, PDGFR, VEGFR3, TRKA or KIT activity, and furthermore particularly FLT3 or KIT activity, which comprises administering to a mammal in need thereof an effective amount of a substituted indazole compound represented by formula (I) as defined above.

A preferred method of the present invention is to treat a disease caused by and/or associated with deregulated protein kinase activity selected from the group consisting of cancer, cell proliferation disorders and immune cell-associated diseases and disorders.

Another preferred method of the present invention is to treat specific types of cancer selected from the group consisting of, but not limited to, carcinoma such as bladder, breast, colon, kidney, liver, lung (including small cell lung cancer), salivary gland, esophagus, gall-bladder, ovary, pancreas, stomach, cervix, thyroid, thymus, prostate, and skin, including squamous cell carcinoma; hematopoietic tumors of lymphoid lineage, including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkitt's lymphoma; hematopoietic tumors of myeloid lineage, including acute and chronic myelogenous leukemias, myelodysplastic syndrome and promyelocytic leukemia; tumors of mesenchymal origin, including gastrointestinal stromal tumor, fibrosarcoma and rhabdomyosarcoma; tumors of the central and peripheral nervous system, including astrocytoma neuroblastoma, glioma and schwannomas; other tumors, including mast cell disease, melanoma, seminoma, teratocarcinoma, osteosarcoma, xeroderma pigmentosum, keratoxanthoma, thyroid follicular cancer, Kaposi's sarcoma and mesothelioma and others.

Another preferred method of the present invention is to treat specific cellular proliferation disorders such as, for example, benign prostate hyperplasia, familial adenomatosis polyposis, neurofibromatosis, psoriasis, vascular smooth cell proliferation associated with atherosclerosis, pulmonary fibrosis, arthritis, glomerulonephritis and post-surgical stenosis and restenosis.

Another preferred method of the present invention is to treat immune cell-associated diseases and disorders, such as inflammatory and autoimmune diseases, for examples multiple sclerosis, systemic lupus erythematosis, inflammatory bowel diseases (IBD), Crohn's disease, irritable bowel syndrome, pancreatitis, ulcerative colitis, diverticulosis, myasthenia gravis, vasculitis, psoriasis, scleroderma, asthma, allergy, systemic sclerosis, vitiligo, arthritis such as osteoarthritis, juvenile rheumatoid arthritis, ankylosing spondylitis.

Another preferred method of the present invention is to treat FLT3 mutated cancers, such as acute myeloid leukemia or myelodisplastic syndrome.

Another preferred method of the present invention is to treat KIT mutated cancers, such as gastrointestinal stromal tumors, melanoma, acute myeloid leukemia, primary adenoid cystic carcinoma of the salivary gland, thymic carcinoma, glioma, testicular seminoma, small cell lung cancers, mast cell disease or piebaldism.

In addition, the method of the present invention also provides tumor angiogenesis and metastasis inhibition.

In a further preferred embodiment, the method of the present invention further comprises subjecting the mammal in need thereof to a radiation therapy or chemotherapy regimen in combination with at least one cytostatic or cytotoxic agent.

Moreover the invention provides an in vitro method for inhibiting FLT3 or KIT protein kinase activity which comprises contacting the said protein with an effective amount of a compound of formula (I).

The present invention also provides a pharmaceutical composition comprising a therapeutically effective amount of a compound of formula (I) or a pharmaceutically acceptable salt thereof and at least one pharmaceutically acceptable excipient, carrier and/or diluent.

The present invention further provides a pharmaceutical composition comprising a compound of formula (I) in combination with one or more chemotherapeutic—e.g. cytostatic or cytotoxic—agents, antibiotic-type agents, alkylating agents, antimetabolite agents, hormonal agents, immunological agents, interferon-type agents, cyclooxygenase inhibitors (e.g. COX-2 inhibitors), matrixmetalloprotease inhibitors, telomerase inhibitors, tyrosine kinase inhibitors, anti-growth factor receptor agents, anti-HER agents, anti-EGFR agents, anti-angiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like.

Additionally, the invention provides a product comprising a compound of formula (I) or a pharmaceutically acceptable salt thereof, as defined above, and one or more chemotherapeutic agents, as a combined preparation for simultaneous, separate or sequential use in anticancer therapy.

In yet another aspect the invention provides a compound of formula (I) or a pharmaceutically acceptable salt thereof, as defined above, for use as a medicament.

Moreover, the invention provides a compound of formula (I) or a pharmaceutically acceptable salt thereof, as defined above, for use in a method of treating cancer.

Finally, the invention provides the use of a compound of formula (I) or a pharmaceutically acceptable salt thereof, as defined above, in the manufacture of a medicament with antitumor activity.

The compounds of formula (I) may have one or more asymmetric centres, and may therefore exist as individual optical isomers or racemic mixtures. Accordingly, all the possible isomers, and their mixtures, of the compounds of formula (I) are within the scope of the present invention.

In cases in which the compounds of formula (I) have unsaturated carbon-carbon double bonds, both the cis (Z) and trans (E) isomers are within the scope of this invention.

Derivatives of compounds of formula (I) originating from metabolism in a mammal, and the pharmaceutically acceptable bio-precursors (otherwise referred to as pro-drugs) of the compounds of formula (I) are also within the scope of the present invention.

In addition to the above, as known to those skilled in the art, the unsubstituted nitrogen on the pyrazole ring of the compounds of formula (I) rapidly equilibrates in solution to form a mixture of tautomers, as depicted below:

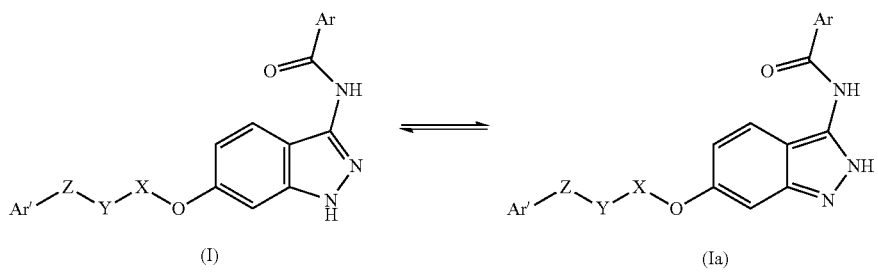

wherein Ar, Ar', X, Y and Z are as defined above.

Accordingly, in the present invention, where only one tautomer is indicated for the compounds of formula (I), the other tautomer (Ia) is also within the scope of the present invention, unless specifically noted otherwise.

Moreover, if easily obtainable from the compounds of formula (I) as defined above, also their hydrates, solvates, complexes and N-oxides are within the scope of the present invention.

N-oxides are compounds of formula (I) wherein nitrogen and oxygen are tethered through a dative bond.

The general terms as used herein, unless otherwise specified, have the meaning reported below.

The term "straight or branched $C_1$-$C_6$ alkyl" refers to a saturated aliphatic hydrocarbon radical, including straight chain and branched chain groups of from 1 to 6 carbon atoms, e.g. methyl, ethyl, propyl, 2-propyl, n-butyl, iso-butyl, tert-butyl, pentyl and the like. The alkyl group may be substituted or unsubstituted; when not otherwise specified, the substituent groups are preferably one to three, independently selected from the group consisting of halogen, cyano, nitro, $SO_nR9$, COR10, NR11R12, OR13, R11R12N—($C_1$-$C_6$)-alkyl, R13O—($C_1$-$C_6$)-alkyl and an optionally further substituted group selected from $C_2$-$C_6$ alkenyl, $C_2$-$C_6$ alkynyl, $C_3$-$C_6$ cycloalkyl, heterocyclyl, aryl and heteroaryl, wherein R9, R10, R11, R12, R13 and n are as defined above.

The term "$C_3$-$C_6$ cycloalkyl" refers to a 3- to 6-membered all-carbon monocyclic ring, which may contain one or more double bonds but does not have a completely conjugated π-electron system. Examples of cycloalkyl groups, without limitation, are cyclopropyl, cyclobutyl, cyclopentyl, cyclopentenyl, cyclohexyl, cyclohexenyl and cyclohexadienyl. A cycloalkyl group may be substituted or unsubstituted; when not otherwise specified, the substituent groups are preferably one to three, independently selected from the group consisting of halogen, cyano, nitro, $SO_nR9$, COR10, NR11R12, OR13, R11R12N—($C_1$-$C_6$)-alkyl, R13O—($C_1$-$C_6$)-alkyl and an optionally further substituted straight or branched $C_1$-$C_6$ alkyl, $C_2$-$C_6$ alkenyl, $C_2$-$C_6$ alkynyl, heterocyclyl, aryl and heteroaryl, wherein R9, R10, R11, R12, R13 and n are as defined above.

The term "heterocyclyl" refers to a 3- to 7-membered, saturated or partially unsaturated carbocyclic ring where one or more carbon atoms are replaced by heteroatoms such as nitrogen, oxygen and sulfur. Not limiting examples of heterocyclyl groups are, for instance, oxiranyl, aziridinyl, oxetanyl, azetidinyl, tetrahydrofuranyl, dihydrofuranyl, tetrahydrothiophenyl, dihydrothiophenyl, pyrrolidinyl, dihydropyrrolyl, pyranyl, dihydropyranyl, tetrahydropyranyl, tetrahydrothiopyranyl, piperidinyl, pyrazolinyl, isoxazolidinyl, isoxazolinyl, thiazolidinyl, thiazolinyl, isothiazolinyl, dioxanyl, piperazinyl, morpholinyl, thiomorpholinyl, examethyleneiminyl, homopiperazinyl and the like. A heterocyclyl group may be substituted or unsubstituted; when not otherwise specified, the substituent groups are preferably one to three, independently selected from the group consisting of halogen, cyano, nitro, $SO_nR9$, COR10, NR11R12, OR13, R11R12N—($C_1$-$C_6$)-alkyl, R13O—($C_1$-$C_6$)-alkyl and an optionally further substituted straight or branched $C_1$-$C_6$ alkyl, $C_2$-$C_6$ alkenyl, $C_2$-$C_6$ alkynyl, $C_3$-$C_6$ cycloalkyl, heterocyclyl, aryl and heteroaryl, wherein R9, R10, R11, R12, R13 and n are as defined above.

The term "aryl" refers to a mono-, bi- or poly-carbocyclic hydrocarbon with from 1 to 4 ring systems, optionally further fused or linked to each other by single bonds, wherein at least one of the carbocyclic rings is "aromatic", wherein the term "aromatic" refers to completely conjugated π-electron bond system. Non limiting examples of such aryl groups are phenyl, α- or β-naphthyl or biphenyl groups.

The term "heteroaryl" refers to aromatic heterocyclic rings, typically 5- to 7-membered heterocycles with from 1 to 3 heteroatoms selected among N, O and S; the heteroaryl ring can be optionally further fused or linked to aromatic and non-aromatic carbocyclic and heterocyclic rings. Not limiting examples of such heteroaryl groups are, for instance, pyridyl, pyrazinyl, pyrimidinyl, pyridazinyl, indolyl, imidazolyl, thiazolyl, isothiazolyl, pyrrolyl, phenyl-pyrrolyl, furyl, phenyl-furyl, oxazolyl, isoxazolyl, pyrazolyl, thienyl, benzothienyl, isoindolinyl, benzoimidazolyl, quinolinyl, isoquinolinyl, 1,2,3-triazolyl, 1-phenyl-1,2,3-triazolyl, 2,3-dihydroindolyl, 2,3-dihydrobenzofuranyl, 2,3-dihydrobenzothiophenyl; benzopyranyl, 2,3-dihydrobenzoxazinyl, 2,3-dihydroquinoxalinyl and the like.

The aryl and heteroaryl groups may be substituted or unsubstituted; when not otherwise specified, the substituent groups are preferably one to three, independently selected from the group consisting of halogen, cyano, nitro, $SO_nR9$, COR10, NR11R12, OR13, R11R12N—($C_1$-$C_6$)-alkyl, R13O—($C_1$-$C_6$)-alkyl and an optionally further substituted straight or branched $C_1$-$C_6$ alkyl, $C_2$-$C_6$ alkenyl, $C_2$-$C_6$ alkynyl, $C_3$-$C_6$ cycloalkyl, heterocyclyl, aryl and heteroaryl, wherein R9, R10, R11, R12, R13 and n are as defined above.

The term "halogen" indicates fluorine, chlorine, bromine or iodine.

The term "$C_2$-$C_6$ alkenyl" indicates an aliphatic $C_2$-$C_6$ hydrocarbon chain containing at least one carbon-carbon double bond and which can be straight or branched. Representative examples include, but are not limited to, ethenyl, 1-propenyl, 2-propenyl, 1- or 2-butenyl, and the like.

The term "$C_2$-$C_6$ alkynyl" indicates an aliphatic $C_2$-$C_6$ hydrocarbon chain containing at least one carbon-carbon triple bond and which can be straight or branched. Representative examples include, but are not limited to, ethynyl, 1-propynyl, 2-propynyl, 1- or 2-butynyl, and the like.

The alkenyl and alkynyl groups may be substituted or unsubstituted; when not otherwise specified, the substituent groups are preferably one to three, independently selected from the group consisting of halogen, cyano, nitro, $SO_nR9$, COR10, NR11R12, OR13, R11R12N—($C_1$-$C_6$)-alkyl, R13O—($C_1$-$C_6$)-alkyl and an optionally further substituted straight or branched $C_1$-$C_6$ alkyl, $C_3$-$C_6$ cycloalkyl, heterocyclyl, aryl and heteroaryl, wherein R9, R10, R11, R12, R13 and n are as defined above.

The term "nitro" indicates a —$NO_2$ group.

The term "cyano" indicates a —CN residue.

The term "pharmaceutically acceptable salt" of compounds of formula (I) refers to those salts that retain the biological effectiveness and properties of the parent compound. Such salts include acid addition salts with inorganic acids such as hydrochloric, hydrobromic, nitric, phosphoric, sulfuric, perchloric acid and the like, or with organic acids such as acetic, trifluoroacetic, propionic, glycolic, lactic, (D) or (L) malic, maleic, fumaric, methanesulfonic, ethanesulfonic, benzoic, p-toluenesulfonic, salicylic, cinnamic, mandelic, tartaric, citric, succinic, malonic acid and the like; salts formed when an acidic proton present in a compound of formula (I) is either replaced by a metal ion, —e.g. an alkali metal ion such as sodium or potassium—or an alkaline earth ion, such as calcium or magnesium, or coordinates with an organic base such as ethanolamine, diethanolamine, triethanolamine, tromethamine, N-methylglucamine, and the like.

A preferred class of compounds of formula (I) are the compounds wherein:

R1 is A, NR6R7, OR8 or an optionally substituted heterocyclyl, wherein A, R6, R7 and R8 are as defined above.

A more preferred class of compounds of formula (I) are the compounds wherein:

Ar is Ar1 or Ar2; and R2, R3, R4, R5 are each independently hydrogen, halogen, NR11R12 or OR13, wherein R11, R12 and R13 are as defined above.

Specific compounds (Cpd.) of the invention or a salt thereof are listed below:

1. N-(6-Benzyloxy-1H-indazol-3-yl)-4-(4-methyl-piperazin-1-yl)-benzamide,
2. 4-(4-Methyl-piperazin-1-yl)-N-(6-phenoxy-1H-indazol-3-yl)-benzamide,
3. N-[6-(3-Fluoro-phenoxy)-1H-indazol-3-yl]-4-(4-methyl-piperazin-1-yl)-benzamide,
4. N-[6-(4-Benzyloxy-phenoxy)-1H-indazol-3-yl]-4-(4-methyl-piperazin-1-yl)-benzamide,
5. 4-(4-Methyl-piperazin-1-yl)-N-[6-(3-phenoxy-benzyloxy)-1H-indazol-3-yl]-benzamide,
6. N-[6-(1-Benzyl-piperidin-4-yloxy)-1H-indazol-3-yl]-4-(4-methyl-piperazin-1-yl)-benzamide,
7. 4-(4-Methyl-piperazin-1-yl)-N-[6-(3-phenyl-prop-2-ynyloxy)-1H-indazol-3-yl]-benzamide,
8. 4-(4-Methyl-piperazin-1-yl)-N-[6-(4-phenoxy-phenoxy)-1H-indazol-3-yl]-benzamide,
9. N-[6-(3-Benzyloxy-phenoxy)-1H-indazol-3-yl]-4-(4-methyl-piperazin-1-yl)-benzamide,
10. 4-(4-Methyl-piperazin-1-yl)-N-[6-(2-phenoxy-ethoxy)-1H-indazol-3-yl]-benzamide,
11. N-[6-(2-Benzyloxy-ethoxy)-1H-indazol-3-yl]-4-(4-methyl-piperazin-1-yl)-benzamide,
12. N-[6-(1-Benzyl-piperidin-3-yloxy)-1H-indazol-3-yl]-4-(4-methyl-piperazin-1-yl)-benzamide,
13. N-[6-(1-Benzyl-pyrrolidin-2-ylmethoxy)-1H-indazol-3-yl]-4-(4-methyl-piperazin-1-yl)-benzamide,
14. N-[6-(2-Benzyloxy-ethoxy)-1H-indazol-3-yl]-4-(4-methyl-4-oxy-piperazin-1-yl)-benzamide,
15. N-[6-(2-Benzyloxy-ethoxy)-1H-indazol-3-yl]-4-(4-dimethylamino-piperidin-1-yl)-benzamide,
16. N-[6-(2-Benzyloxy-ethoxy)-1H-indazol-3-yl]-4-[(2-dimethylamino-ethyl)-methyl-amino]-benzamide,
17. N-[6-(2-Benzyloxy-ethoxy)-1H-indazol-3-yl]-4-[(3-dimethylamino-propyl)-methyl-amino]-benzamide,
18. 4-{4-[6-(2-Benzyloxy-ethoxy)-1H-indazol-3-ylcarbamoyl]-phenyl}-piperazine-1-carboxylic acid tert-butyl ester,
19. N-[6-(2-Benzyloxy-ethoxy)-1H-indazol-3-yl]-4-(1-methyl-piperidin-4-ylamino)-benzamide,
20. N-[6-(2-Benzyloxy-ethoxy)-1H-indazol-3-yl]-4-piperazin-1-yl-benzamide,
21. N-[6-(2-Benzyloxy-ethoxy)-1H-indazol-3-yl]-4-dimethylaminomethyl-benzamide,
22. N-[6-(2-Benzyloxy-ethoxy)-1H-indazol-3-yl]-4-(1-methyl-piperidin-4-yloxy)-benzamide,
23. N-[6-(2-Benzyloxy-ethoxy)-1H-indazol-3-yl]-4-[methyl-(1-methyl-piperidin-4-yl)-amino]-benzamide,
24. N-[6-(2-Benzyloxy-ethoxy)-1H-indazol-3-yl]-4-morpholin-4-yl-benzamide,
25. N-[6-(2-Benzyloxy-ethoxy)-1H-indazol-3-yl]-4-(2-morpholin-4-yl-ethylamino)-benzamide,
26. N-[6-(2-Benzyloxy-ethoxy)-1H-indazol-3-yl]-4-(tetrahydro-pyran-4-ylamino)-benzamide,
27. N-[6-(2-Benzyloxy-ethoxy)-1H-indazol-3-yl]-4-[(1-methyl-piperidin-4-ylmethyl)-amino]-benzamide,
28. N-[6-(2-Benzyloxy-ethoxy)-1H-indazol-3-yl]-4-(3-pyrrolidin-1-yl-azetidin-1-yl)-benzamide, 29. N-[6-(2-Benzyloxy-ethoxy)-1H-indazol-3-yl]-3-(4-methyl-piperazin-1-yl)-benzamide,
30. N-{6-[2-(2-Fluoro-benzyloxy)-ethoxy]-1H-indazol-3-yl}-4-(4-methyl-piperazin-1-yl)-benzamide,
31. N-{6-[2-(3-Fluoro-benzyloxy)-ethoxy]-1H-indazol-3-yl}-4-(4-methyl-piperazin-1-yl)-benzamide,
32. N-{6-[2-(4-Fluoro-benzyloxy)-ethoxy]-1H-indazol-3-yl}-4-(4-methyl-piperazin-1-yl)-benzamide,
33. 4-(4-Methyl-piperazin-1-yl)-N-{6-[2-(4-trifluoromethyl-benzyloxy)-ethoxy]-1H-indazol-3-yl}-benzamide,
34. 4-(4-Methyl-piperazin-1-yl)-N-{6-[2-(3-trifluoromethyl-benzyloxy)-ethoxy]-1H-indazol-3-yl}-benzamide,
35. 4-(4-Methyl-piperazin-1-yl)-N-{6-[2-(pyridin-4-yl-methoxy)-ethoxy]-1H-indazol-3-yl}-benzamide,
36. 4-(4-Methyl-piperazin-1-yl)-N-{6-[2-(pyridin-3-yl-methoxy)-ethoxy]-1H-indazol-3-yl}-benzamide,
37. 4-(4-Methyl-piperazin-1-yl)-N-{6-[2-(pyridin-2-yl-methoxy)-ethoxy]-1H-indazol-3-yl}-benzamide,
38. N-[6-(2-Benzyloxy-ethoxy)-1H-indazol-3-yl]-2-fluoro-4-(4-methyl-piperazin-1-yl)-benzamide,
39. 4-(4-Methyl-piperazin-1-yl)-N-[6-((E)-3-phenyl-allyloxy)-1H-indazol-3-yl]-benzamide,
40. N-{6-[2-(4-Methoxy-benzyloxy)-ethoxy]-1H-indazol-3-yl}-4-(4-methyl-piperazin-1-yl)-benzamide,
41. N-[6-(2-Benzyloxy-ethoxy)-1H-indazol-3-yl]-4-[methyl-(1-methyl-1-oxy-piperidin-4-yl)-amino]-benzamide,
42. 4-(4-Methyl-4-oxy-piperazin-1-yl)-N-{6-[2-(4-trifluoromethyl-benzyloxy)-ethoxy]-1H-indazol-3-yl}-benzamide and
43. N-[6-(2-Benzyloxy-ethoxy)-1H-indazol-3-yl]-2,4-bis-(4-methyl-piperazin-1-yl)-benzamide.

The present invention also provides a process for the preparation of a compound of formula (I) as defined above, by using the reaction routes and synthetic schemes described below, employing the techniques available in the art and starting materials readily available. The preparation of certain embodiments of the present invention is described in the examples that follow, but those of ordinary skill in the art will recognize that the preparations described may be readily adapted to prepare other embodiments of the present invention. For example, the synthesis of non-exemplified compounds according to the invention may be performed by modifications apparent to those skilled in the art, for instance by appropriately protecting interfering groups, by changing to other suitable reagents known in the art, or by making routine modifications of reaction conditions. Alternatively other reactions referred to herein or known in the art will be recognized as having adaptability for preparing other compounds of the invention.

The reported Scheme 1 and Scheme 2 show the preparations of a compound of formula (I).

Scheme 1

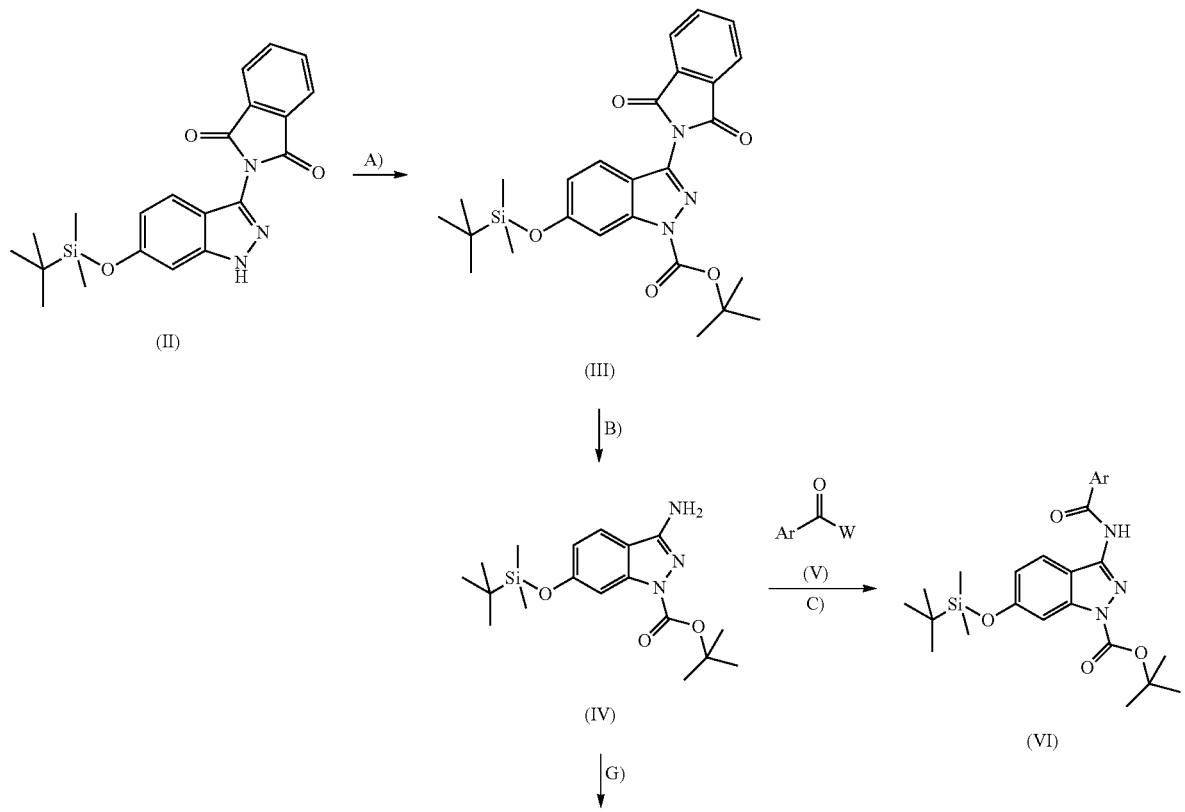

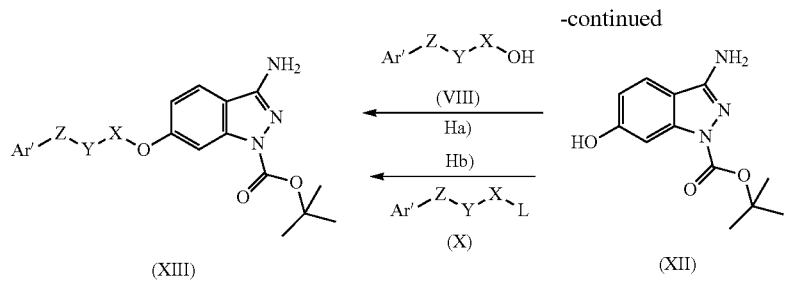
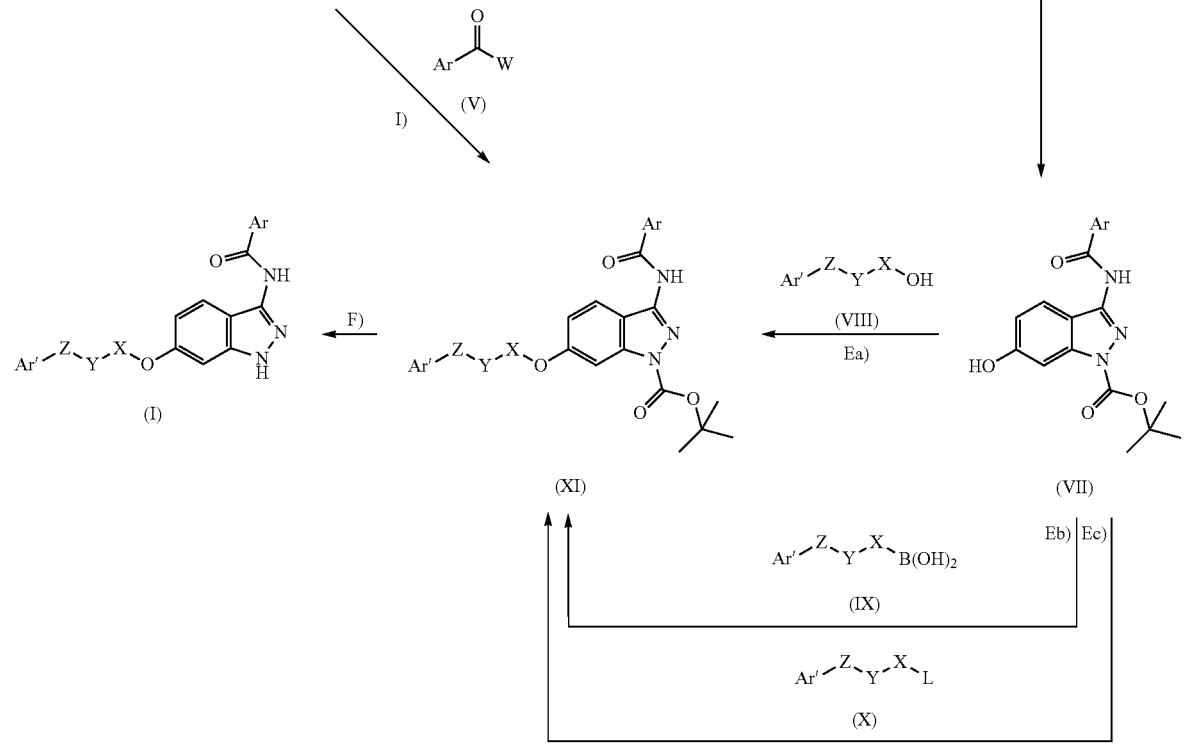
wherein Ar is as defined in formula (I); W is hydroxy, halogen or a suitable leaving group; X, Y, Z and Ar' are as defined in formula (I); and L is a suitable leaving group, such as halogen, methanesulfonyloxy, trifluoromethanesulfonyloxy or p-toluenesulfonyloxy.
Scheme 2
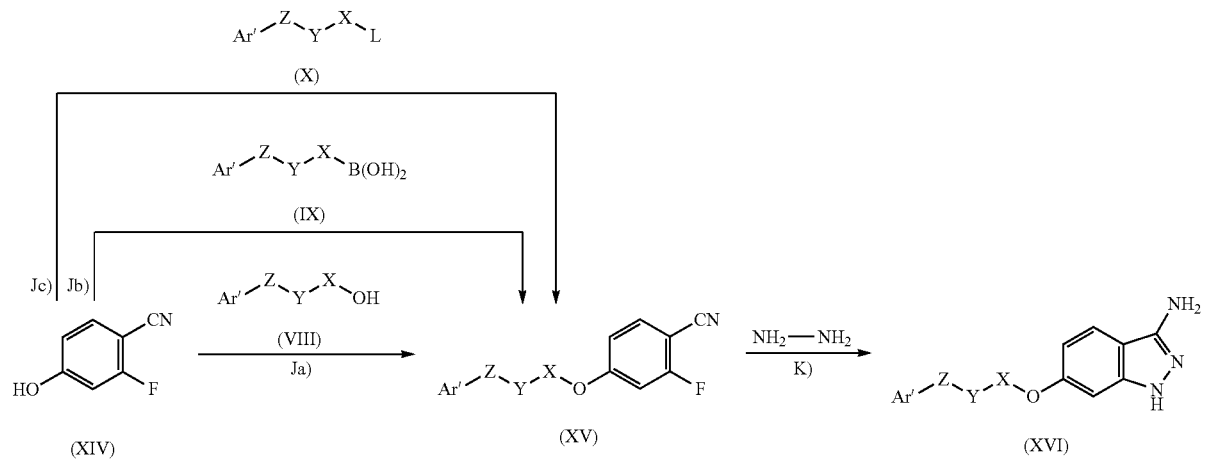

wherein Ar is as defined in formula (I); W is hydroxy, halogen or a suitable leaving group; X, Y, Z and Ar' are as defined in formula (I); and L is a suitable leaving group, such as halogen, methanesulfonyloxy, trifluoromethanesulfonyloxy or p-toluenesulfonyloxy.

All those with ordinary skills in the art will appreciate that any transformation performed according to said methods may require standard modifications such as, for instance, protection of interfering groups, change to other suitable reagents known in the art, or make routine modifications of reaction conditions.

Accordingly, a process of the present invention comprises the following steps:

A) introducing the tert-butoxy-carbonyl group into the compound of formula (II)

B) cleaving the phthalimido group of the resultant compound of formula (III)

C) acylating the resultant compound of formula (IV)

by reaction with a compound of formula (V)

wherein Ar is as defined in formula (I) and W is hydroxy, halogen or a suitable leaving group;

D) selectively cleaving the tert-butyldimethylsilyl ether of the resultant compound of formula (VI)

(VI)

wherein Ar is as defined in formula (I);

E) coupling the resultant compound of formula (VII)

(VII)

wherein Ar is as defined in formula (I), alternatively with:

Ea) a compound of formula (VIII)

$$Ar'\text{-}Z\text{-}Y\text{-}X\text{-}OH$$ (VIII)

wherein Ar', Z and Y are as defined in formula (I) and X is an optionally substituted group selected from straight or branched $C_1$-$C_6$ alkyl and heterocyclyl;

or

Eb) a compound of formula (IX)

$$Ar'\text{-}Z\text{-}Y\text{-}X\text{-}B(OH)_2$$ (IX)

wherein Ar', Z and Y are as defined in formula (I) and X is an optionally substituted aryl or wherein Ar' is as defined in formula (I) and X, Y and Z are a bond;

or

Ec) a compound of formula (X)

$$Ar'\text{-}Z\text{-}Y\text{-}X\text{-}L$$ (X)

wherein Ar', Z and Y are as defined in formula (I), X is an optionally substituted group selected from straight or branched $C_1$-$C_6$ alkyl or heterocyclyl and L is a suitable leaving group, such as halogen, methanesulfonyloxy, trifluoromethanesulfonyloxy or p-toluenesulfonyloxy;

F) cleaving the tert-butoxy-carbonyl group of the resultant compound of formula (XI) obtained in step Ea), Eb) or Ec)

(XI)

wherein Ar, Ar', X, Y and Z are as defined in formula (I), so as to obtain a compound of formula (I), as defined above; optionally separating the resultant compound of formula (I) into the single isomers; optionally converting the resultant compound of formula (I) into a different compound of formula (I), and/or into a pharmaceutically acceptable salt if desired.

Alternatively, the intermediate compound of formula (XI), wherein Ar, Ar', Y and Z are as defined in formula (I) and X is an optionally substituted group selected from straight or branched $C_1$-$C_6$ alkyl and heterocyclyl, can be obtained in a process comprising the following steps:

G) selectively cleaving the tert-butyldimethylsilyl ether of the compound of formula (IV), as defined above;

H) coupling the resultant compound of formula (XII)

(XII)

alternatively with:

Ha) a compound of formula (VIII), as defined above;

or

Hb) a compound of formula (X), as defined above;

I) acylating the resultant compound of formula (XIII)

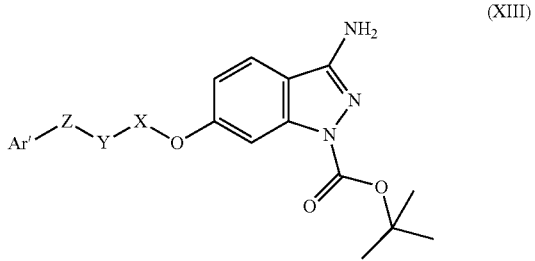

wherein Ar, Ar', Y and Z are as defined in formula (I) and X is an optionally substituted group selected from straight or branched $C_1$-$C_6$ alkyl and heterocyclyl, with a compound of formula (V), as defined above, so as to obtain a compound of formula (XI), wherein Ar, Ar', Y and Z are as defined in formula (I) and X is an optionally substituted group selected from straight or branched $C_1$-$C_6$ alkyl and heterocyclyl.

It is a further object of the present invention a process for preparing the compound of formula (I), as defined above, comprising the following steps:

J) coupling the compound of formula (XIV)

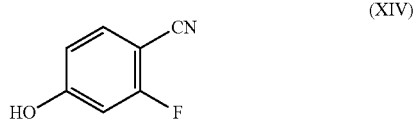

alternatively with:
Ja) a compound of formula (VIII), as defined above; or
Jb) a compound of formula (IX), as defined above; or
Jc) a compound of formula (X), as defined above;
K) converting the resultant compound of formula (XV)

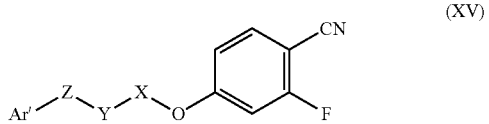

wherein Ar', X, Y and Z are as defined in formula (I);
L) acylating the resultant compound of formula (XVI)

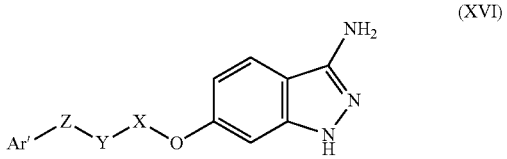

wherein Ar', X, Y and Z are as defined in formula (I), with a compound of formula (V), as defined above, so as to obtain a compound of formula (I), as defined above; optionally separating the resultant compound of formula (I) into the single isomers; optionally converting the resultant compound of formula (I) into a different compound of formula (I), and/or into a pharmaceutically acceptable salt if desired.

It is a further object of the present invention a process for preparing a compound of formula (I), wherein R1 is NR6R7, wherein R6 is as defined above and R7 is hydrogen, a substituted straight or branched $C_1$-$C_6$ alkyl or an optionally substituted group selected from straight or branched $C_2$-$C_6$ alkenyl, straight or branched $C_2$-$C_6$ alkynyl, $C_3$-$C_6$ cycloalkyl, heterocyclyl, aryl and heteroaryl, and wherein Ar, Ar', X, Y and Z are as defined above, comprising the following steps:
M) acylating the compound of formula (XVI), as defined above, with a compound of formula (XVII)

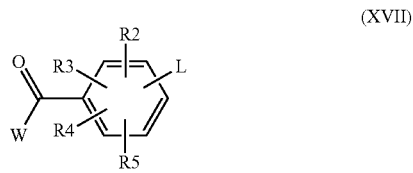

wherein R2, R3, R4 and R5 are as defined in formula (I) and W and L are as defined above;
N) coupling the resultant compound of formula (XVIII)

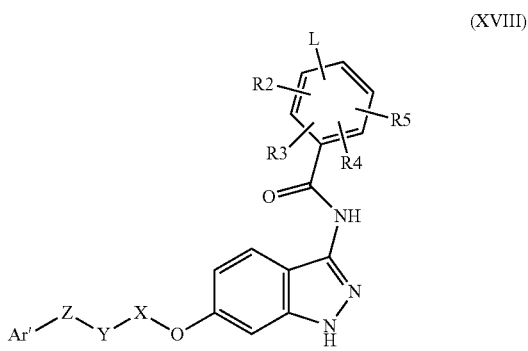

wherein Ar', X, Y, Z, R2, R3, R4 and R5 are as defined in formula (I) and L is as defined above, with a compound of formula (XIX)

wherein R6 is as defined in formula (I) and R7 is hydrogen, a substituted straight or branched $C_1$-$C_6$ alkyl or an optionally substituted group selected from straight or branched $C_2$-$C_6$ alkenyl, straight or branched $C_2$-$C_6$ alkynyl, $C_3$-$C_6$ cycloalkyl, heterocyclyl, aryl and heteroaryl, so as to obtain a compound of formula (I), wherein R1 is NR6R7, wherein R6 is as defined in formula (I) and R7 is hydrogen, a substituted straight or branched $C_1$-$C_6$ alkyl or an optionally substituted group selected from straight or branched $C_2$-$C_6$ alkenyl, straight or branched $C_2$-$C_6$ alkynyl, $C_3$-$C_6$ cycloalkyl, heterocyclyl, aryl and heteroaryl, and Ar, Ar', X, Y and Z are as defined in formula (I); optionally separating the resultant compound of formula (I) into the single isomers; optionally converting the resultant compound of formula (I) into a different compound of formula (I), and/or into a pharmaceutically acceptable salt if desired.

As said above, the compounds of formula (I) which are prepared according to the process object of the invention, can be conveniently converted into other compounds of formula (I) by operating according to well-known synthetic conditions, the following being examples of possible conversions:

1) reducing a compound of formula (I) wherein one of the substituents R1, R2, R3, R4 or R5 is $NO_2$, for obtaining the corresponding compound of formula (I) wherein such substituent is $NH_2$;
2) acylating a compound of formula (I) wherein one of the substituents R1, R2, R3, R4 or R5 is $NH_2$, by reaction with an acylating agent of formula (XX) or (XXI)

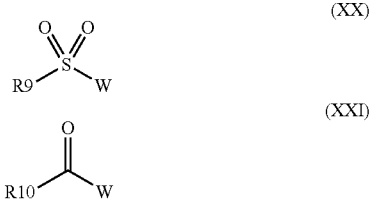

wherein R9, R10 and W are as defined above, for obtaining the corresponding compound of formula (I) wherein such substituent is a $NHSO_2R9$ or NHCOR10 residue, wherein R9 and R10 are as defined above;
3) reacting a compound of formula (I) wherein the substituent R1 is $NH_2$, with a suitable aldehyde or ketone in the presence of a reducing agent, for obtaining the corresponding compound of formula (I) wherein such substituent is a NR6R7 group, wherein R7 is hydrogen and R6 is as defined in formula (I) except hydrogen;
4) reacting a compound of formula (I) wherein one of the substituents R2, R3, R4 or R5 is $NH_2$, with a suitable aldehyde or ketone in the presence of a reducing agent, for obtaining the corresponding compound of formula (I) wherein such substituent is a NR11R12 group, wherein one of the R11 or R12 is hydrogen and the other is as defined in formula (I) except hydrogen, $SO_nR9$ or COR10;
5) hydrolysing a compound of formula (I) wherein one of the substituents R1, R2, R3, R4 or R5 is a COOR13 residue, wherein R13 is a straight or branched $C_1$-$C_6$ alkyl, under acid or basic catalysis, so as to obtain the corresponding compound of formula (I) wherein such substituent is a COOH group, in which case R13 represents hydrogen;
6) amidating a compound of formula (I) wherein one of the substituents R1, R2, R3, R4 or R5 is a COOH residue, with an amine of formula (XXII)

wherein R11 and R12 are as defined in formula (I) except $SO_nR9$ or COR10, for obtaining the corresponding compound of formula (I) wherein such substituent is a CONR11R12 residue, wherein R11 and R12 are as defined in formula (I) except $SO_nR9$ or COR10;
7) oxidazing a compound of formula (I) wherein R1 is 4-methyl-piperazin-1-yl for obtaining the corresponding compound of formula (I) wherein such substituent is 4-methyl-4-oxy-piperazin-1-yl;
8) cleaving the tert-butoxy-carbonyl group of a compound of formula (I) wherein R1 is 4-tert-butoxycarbonyl-piperazin-1-yl for obtaining the corresponding compound of formula (I) wherein such substituent is piperazin-1-yl.

According to step A), the transformation of the compound of formula (II) into the compound of formula (III) can be accomplished in a variety of ways and experimental conditions, which are widely known in the art for the introduction of the tert-butoxy-carbonyl group, for example using di-tert-butyl dicarbonate. Preferably, this reaction is carried out in a suitable solvent such as, for instance, tetrahydrofuran, dichloromethane, toluene, 1,4-dioxane, and in the presence of a proton scavenger such as, for example, pyridine, triethylamine, N,N-diisopropylethylamine, at a temperature ranging from room temperature to reflux, for a time ranging from about 30 min. to about 96 hours.

According to step B), the cleavage of the phthalimido group of the compound of formula (III) to give the compound of formula (IV) can be accomplished in a variety of ways and experimental conditions, which are widely known in the art, for example using hydrazine. Preferably, this reaction is carried out in a suitable solvent such as, for instance, tetrahydrofuran, dichloromethane, toluene, 1,4-dioxane, at a temperature ranging from room temperature to reflux, for a time ranging from about 30 min. to about 96 hours.

According to step C), a compound of formula (VI) can be obtained by reacting a compound of formula (IV) with a compound of formula (V) in a variety of ways and experimental conditions, which are widely known in the art for acylation reactions. Preferably a compound of formula (V) wherein W is hydroxy is converted into its corresponding acyl chloride wherein W is chlorine in the presence of thionyl chloride or oxalyl chloride, in a suitable solvent, such as toluene, dichloromethane, chloroform, diethyl ether, tetrahydrofuran, 1,4-dioxane, or a mixture thereof, at a temperature ranging from about −10° C. to reflux and for a period of time varying from about 1 hour to about 96 hours. The acyl chloride is isolated by evaporation of the solvent and further reacted with (IV) in the presence of a base such as pyridine, triethylamine or N,N-diisopropylethylamine, at a temperature ranging from about −40° C. to reflux and for a period of time varying from about 1 hour to about 96 hours. A suitable solvent may also be added, such as toluene, dichloromethane, chloroform, diethyl ether, tetrahydrofuran, 1,4-dioxane. Alternatively, a compound of formula (IV) is reacted with a compound of formula (V) wherein W is hydroxy in the presence of an activating agent such as hydroxybenzotriazole, dicyclohexyl carbodiimide, diisopropyl carbodiimide, 1-ethyl-3-(3'-dimethylamino)carbodiimide hydrochloric acid salt, O-(benzotriazol-1-yl)-N,N,N',N'-tetramethyluronium tetrafluoroborate. Preferably, this reaction is carried out in a suitable solvent such as, for instance, tetrahydrofuran, dichloromethane, toluene, 1,4-dioxane, N,N-dimethylformamide, N,N-dimethylacetamide and in the presence of a proton scavenger such as, for example, pyridine, triethylamine, N,N-diisopropylethylamine, at a temperature ranging from room temperature to reflux, for a time ranging from about 30 min. to about 96 hours.

According to step D), the selective cleavage of the tert-butyldimethylsilyl ether of the compound of formula (VI) to give the compound of formula (VII) can be carried out in a variety of ways, according to conventional methods well known in the literature. Preferably this conversion is carried out in the presence of tetrabutylammonium fluoride in a suitable solvent, such as, for instance, tetrahydrofuran, dichloromethane, toluene, 1,4-dioxane, at a temperature ranging from −10° C. to reflux, for a time ranging from about 30 min. to about 96 hours.

According to step Ea), the coupling of a compound of formula (VII) with an alcohol of formula (VIII) to give a compound of formula (XI) can be accomplished in a variety of ways and experimental conditions which are widely known in the art for the synthesis of aryl ethers under Mitsunobu-like conditions. Preferably this conversion is carried out in the presence of an azodicarboxylate, such as, for example, diethyl azodicarboxylate, diisopropyl azodicarboxylate or di-tert-butyl azodicarboxylate and a phosphine, such as, for example, triphenylphosphine or polymer-bound triphenylphosphine, in a suitable solvent, such as, for instance, tetrahydrofuran, dichloromethane, 1,4-dioxane, toluene, acetonitrile at a temperature ranging from −20° C. to reflux, for a time ranging from about 30 min. to about 96 hours.

According to step Eb), the coupling of a compound of formula (VII) with a boronic acid of formula (IX) to give a compound of formula (XI) can be accomplished in a variety of ways and experimental conditions which are widely known in the art for the synthesis of di-aryl ethers. Preferably this conversion is carried out in the presence of copper diacetate and 4A molecular sieve or silica gel, in a suitable solvent, such as, for instance, tetrahydrofuran, dichloromethane, 1,4-dioxane and in the presence of a proton scavenger such as, for example, pyridine, triethylamine, N,N-diisopropylethylamine, at a temperature ranging from −10° C. to reflux, for a time ranging from about 30 min. to about 96 hours.

According to step Ec), the coupling of a compound of formula (VII) with a compound of formula (X) to give a compound of formula (XI) can be accomplished in a variety of ways and experimental conditions which are widely known in the art for the alkylation of phenols. Preferably a compound of formula (VII) is treated with a chloride, bromide, iodide, mesylate or triflate of formula (X), in which case L represents chlorine, bromine, iodine, methanesulfonyloxy or trifluoromethanesulfonyloxy, respectively, in the presence of a proton scavenger such as, for example, triethylamine, N,N-diisopropylethylamine, sodium, potassium or cesium carbonate, in a suitable solvent such as, for instance, tetrahydrofuran, 1,4-dioxane, N,N-dimethylformamide, N,N-dimethylacetamide, dimethoxyethane, at a temperature ranging from −10° C. to reflux, for a time ranging from about 30 min. to about 96 hours.

According to step F), the transformation of a compound of formula (XI) into a compound of formula (I) can be carried out in a variety of ways, according to conventional methods well known in the literature for the cleavage of a tert-butoxycarbonyl group. As an example, this reaction may be run under acidic conditions, for example in the presence of an inorganic or organic acid such as hydrochloric, trifluoroacetic or methanesulfonic acid, in a suitable solvent such as dichloromethane, 1,4-dioxane, a lower alcohol, such as methanol or ethanol, water, or a mixture thereof, at a temperature ranging from room temperature to reflux and for a period of time ranging from about 30 min. to about 96 hours.

According to step G), the transformation of the compound of formula (IV) into the compound of formula (XII) can be carried out in a way analogous to that specified above under D).

According to step Ha), the coupling between the compound of formula (XII) and an alcohol of formula (VIII) can be carried out in a way analogous to that specified above under Ea).

According to step Hb), the coupling between the compound of formula (XII) and a compound of formula (X) can be carried out in a way analogous to that specified above under Ec).

According to step I), the acylation of the compound of formula (XIII) with a compound of formula (V) can be carried out in a way analogous to that specified above under C).

According to step Ja), the coupling between the compound of formula (XIV) and an alcohol of formula (VIII) can be carried out in a way analogous to that specified above under Ea).

According to step Jb), the coupling between the compound of formula (XIV) and a boronic acid of formula (IX) can be carried out in a way analogous to that specified above under Eb).

According to step Jc), the coupling between the compound of formula (XIV) and a compound of formula (X) can be carried out in a way analogous to that specified above under Ec).

According to step K), a compound of formula (XV) can be transformed into a compound of formula (XVI) in a variety of ways and experimental conditions. Preferably, this reaction is carried out in the presence of hydrazine or hydrazine monohydrate in a suitable solvent such as, for instance, toluene, tetrahydrofuran, 1,4-dioxane, dimethyl sulfoxide, acetonitrile, methanol, ethanol or n-butanol, at a temperature ranging from 0° C. to reflux and for a period of time varying from about 30 min to about 96 hours.

According to step L), the acylation of the compound of formula (XVI) with a compound of formula (V) can be carried out in a way analogous to that specified above under C).

According to step M), the acylation of the compound of formula (XVI) with a compound of formula (XVII) can be carried out in a way analogous to that specified above under C).

According to step N), the coupling of a compound of formula (XVIII) with an amine of formula (XIX) can be carried out in a variety of ways, according to conventional methods well known in the literature for Buchwald-Hartwig aminations. Preferably a compound of formula (XVIII) wherein L is chlorine, bromine, iodine or trifluoromethanesulfonyloxy is reacted with a compound of formula (XIX) in a suitable solvent such as, for example, tetrahydrofuran, 1,4-dioxane, N,N-dimethylformamide, N,N-dimethylacetamide, dimethoxyethane, acetonitrile, toluene, in the presence of catalytic amounts of a palladium derivative, such as, for example, tris(dibenzylideneacetone)dipalladium(0), palladium diacetate, and a phosphine ligand, such as, for example, 2,2'-bis(diphenylphosphino)-1,1'-binaphthyl, 4,5-bis(diphenylphosphino)-9,9-dimethylxanthene, 2-dicyclohexylphosphino-2',4',6'-triisopropylbiphenyl, 2-dicyclohexylphosphino-2'-(N,N-dimethylamino)biphenyl, in the presence of a base, such as, for instance, sodium or lithium bis(trimethylsilyl)amide, sodium or potassium tert-butoxide, sodium, potassium or cesium carbonate, at a temperature ranging from 0° C. to reflux and for a period of time varying from about 15 min to about 96 hours.

According to the conversion 1), the reduction of a compound of formula (I) wherein one of the substituents R1, R2, R3, R4 or R5 is nitro, for obtaining a compound of formula (I) wherein such substituent is amino, can be carried out in a variety of ways, according to conventional methods well known in the literature. Preferably this conversion is carried out in a suitable solvent such as, for instance, methanol, ethanol, water, tetrahydrofuran, 1,4-dioxane, N,N-dimethylformamide, acetic acid, or a mixture thereof, in the presence of a suitable reducing agent, such as, for instance, hydrogen and a hydrogenation catalyst, or by treatment with cyclohexene or cyclohexadiene, or formic acid or ammonium formate and a hydrogenation catalyst, or a metal such as iron or zinc in the presence of an inorganic acid, such as hydrochloric acid, or by treatment with tin (II) chloride or sodium hydrosulfite in the presence of tetrabutylammonium chloride, at a temperature ranging from 0° C. to reflux and for a time varying from about 1 hour to about 96 hours. The hydrogenation catalyst is usually a metal, most often palladium, which can be used as such or supported on carbon.

According to the conversion 2), the acylation of a compound of formula (I) wherein one of the substituents R1, R2, R3, R4 or R5 is $NH_2$, by reaction with an acylating agent of formula (XX) or (XXI) to give a compound of formula (I) wherein such substituent is a $NHSO_2R9$ or NHCOR10 residue, can be carried out in a variety of ways, according to conventional methods well known in the literature. Preferably this conversion is carried out in a way analogous to that specified above under C).

According to the conversion 3), the reaction of a compound of formula (I), wherein the substituent R1 is $NH_2$, with a suitable aldehyde or ketone for obtaining a compound of formula (I) wherein such substituent is a NR6R7 group, can be conducted in a variety of ways, according to conventional methods for carrying out reductive alkylations. Preferably, this reaction is carried out in a suitable solvent such as, for instance, methanol, N,N-dimethylformamide, dichloromethane, tetrahydrofuran, or a mixture thereof, in the presence of a suitable reducing agent such as, for instance, sodium borohydride, tetra-alkylammonium borohydride, sodium cyano borohydride, sodium triacetoxyborohydride, tetramethylammonium triacetoxy borohydride and in the presence of an acid catalyst, such as, for instance, acetic acid or trifluoroacetic acid, at a temperature ranging from about 0° C. to reflux and for a time varying from about 1 hour to about 96 hours.

According to the conversion 4), the reaction of a compound of formula (I), wherein one of the substituents R2, R3, R4 or R5 is $NH_2$, with a suitable aldehyde or ketone in the presence of a reducing agent, for obtaining a compound of formula (I) wherein such substituent is a NR11R12 group, can be conducted in a variety of ways, according to conventional methods for carrying out reductive alkylations. Preferably this conversion is carried out in a way analogous to that specified above under 3).

According to the conversion 5), the hydrolysis of a compound of formula (I) wherein one of the substituents R1, R2, R3, R4 or R5 is a COOR13 residue, wherein R13 is a straight or branched $C_1$-$C_6$ alkyl, to give the corresponding carboxylic acid can be conducted in a variety of ways, according to methods widely known in the art for the hydrolysis of ester groups. Preferably such hydrolysis is carried out in the presence of an inorganic base, such as, for example, lithium, sodium or potassium hydroxide, or an inorganic or organic acid, such as, for example, hydrochloric acid, trifluoroacetic acid, in a suitable solvent such as, for instance, methanol, ethanol, tetrahydrofuran, 1,4-dioxane, water or a mixture thereof, at a temperature ranging from about 0° C. to reflux and for a time varying from about 1 hour to about 96 hours.

According to the conversion 6), the amidation of a compound of formula (I) wherein one of the substituents R1, R2, R3, R4 or R5 is a COOH residue, with an amine of formula (XXII), can be can be conducted in a variety of ways, according to conventional methods for the synthesis of carboxamides. Preferably, this conversion is carried out in the presence of an activating agent such as hydroxybenzotriazole, dicyclohexyl carbodiimide, diisopropyl carbodiimide, 1-ethyl-3-(3'-dimethylamino)carbodiimide hydrochloric acid salt, O-(benzotriazol-1-yl)-N,N,N',N'-tetramethyluronium tetrafluoroborate, in a suitable solvent such as, for instance, tetrahydrofuran, dichloromethane, toluene, 1,4-dioxane, N,N-dimethylformamide, N,N-dimethylacetamide and in the presence of a proton scavenger such as, for example, pyridine, triethylamine, N,N-diisopropylethylamine, at a temperature ranging from room temperature to reflux, for a time ranging from about 30 min. to about 96 hours.

According to the conversion 7), the oxidation of a compound of formula (I) wherein R1 is 4-methyl-piperazin-1-yl for obtaining a compound of formula (I) wherein such substituent is 4-methyl-4-oxy-piperazin-1-yl can be conducted in a variety of ways, according to conventional methods for the N-oxidation of tertiary amines. Preferably, this conversion is carried out in the presence of an oxidizing agent such as, for example, 3-chloroperbenzoic acid, hydrogen peroxide, dimethyldioxirane, in a suitable solvent such as, for instance, dichloromethane, methanol, ethanol, water, acetone, or a mixture thereof, at a temperature ranging from −10° C. to reflux, for a time ranging from about 30 min. to about 96 hours.

According to the conversion 8) the cleavage of the tert-butoxy-carbonyl group of a compound of formula (I) wherein R1 is 4-tert-butoxycarbonyl-piperazin-1-yl for obtaining a compound of formula (I) wherein such substituent is piperazin-1-yl can be carried out in a way analogous to that specified above under F).

It is known to the skilled person that when a compound of formula (V), formula (XVII), formula (XX) or formula (XXI) carries functional groups that may interfere in acylation reactions, such groups have to be protected before carrying out the reaction. In particular, when a compound of formula (V), formula (XVII), formula (XX) or formula (XXI) is substituted by residues of general formula NR6R7, NR11R12, OR8, or OR13 wherein R8 or R13 or at least one of R6 and R7 or at least one of R11 and R12 represent hydrogen, such groups may be protected as known in the art. It is also known to the skilled person that such protecting group may be removed just after the reaction or at a later stage in the synthetic process.

The deprotection of a compound of formula (I) wherein one of the substituents is a protected amino group can be made in a variety of ways according to conventional methods for deprotecting amino groups. Depending on the amino protecting group, this reaction can be conducted in different ways. In one aspect, such reaction can be carried out by treatment with an inorganic acid, such as hydrochloric, sulphuric or perchloric acid, or an organic acid, such as trifluoroacetic or methanesulfonic acid, in a suitable solvent, such as water, methanol, ethanol, 1,4-dioxane, tetrahydrofuran, diethyl ether, diisopropyl ether, acetonitrile, N,N-dimethylformamide, dichloromethane or mixtures thereof, at a temperature ranging from −20° C. to 80° C., and for a period of time ranging from 30 minutes to 48 hours. In another aspect, such reaction can be carried out by treatment with an inorganic base, such as lithium or sodium or potassium hydroxide, or sodium or potassium or cesium carbonate, or with an organic base, such as triethylamine or N,N-diisopropylethylamine, or with anhydrous hydrazine or hydrazine hydrate in a suitable solvent such as water, methanol, ethanol, 1,4-dioxane, tetrahydrofuran, diethyl ether, diisopropyl ether, acetonitrile, N,N-dimethylformamide, dichlorometane or mixtures thereof, at a temperature ranging from −20° C. to 80° C., and for a period of time ranging from 30 minutes to 72 hours.

It is known to the skilled person that transformation of a chemical function into another may require that one or more reactive centers in the compound containing this function be protected in order to avoid undesired side reactions. Protection of such reactive centers, and subsequent deprotection at the end of the synthetic transformations, can be accomplished following standard procedures described, for instance, in: Green, Theodora W. and Wuts, Peter G.M.—Protective Groups in Organic Synthesis, Third Edition, John Wiley & Sons Inc., New York (N.Y.), 1999.

In cases where a compound of formula (I) contains one or more asymmetric centers, said compound can be separated into the single isomers by procedures known to those skilled in the art. Such procedures comprise standard chromatographic techniques, including chromatography using a chiral stationary phase, or crystallization. General methods for separation of compounds containing one or more asymmetric centers are reported, for instance, in Jacques, Jean; Collet, André; Wilen, Samuel H., —Enantiomers, Racemates, and Resolutions, John Wiley & Sons Inc., New York (N.Y.), 1981.

A compound of formula (I) can also be transformed into a pharmaceutically acceptable salt according to standard procedures that are known to those skilled in the art. Alternatively, a compound of formula (I) that is obtained as a salt can be transformed into the free base or the free acid according to standard procedures that are known to the skilled person.

According to any variant of the process for preparing the compounds of formula (I), the starting materials and any other reactant, i.e. compounds of formula (II), (V), (VIII), (IX), (X), (XIV), (XVII), (XIX), (XX), (XXI) and (XXII) are either commercially available, known, or easily prepared according to well-known methods described, for instance, in: B. M. Trost and I. Fleming, Comprehensive Organic Synthesis, 1991, Pergamon Press; A. R. Katritzky, O. Meth-Cohn and C. W. Rees, Comprehensive Organic Functional Group Transformations, 1995, Elsevier Pergamon; A. R. Katritzky and R. J. K. Taylor, Comprehensive Organic Functional Group Transformations II, 2005, Elsevier Pergamon. In particular, the compound of formula (II) can be prepared as described in WO2003028720 and the compound of formula (XIV) is commercially available.

The compounds of the present invention can be administered either as single agents or, alternatively, in combination with known anticancer treatments such as radiation therapy or chemotherapy regimen in combination with cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors), matrixmetalloprotease inhibitors, telomerase inhibitors, tyrosine kinase inhibitors, anti-growth factor receptor agents, anti-HER agents, anti-EGFR agents, anti-angiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like.

If formulated as a fixed dose, such combination products employ the compounds of this invention within the dosage range described below and the other pharmaceutically active agent within the approved dosage range.

Compounds of formula (I) may be used sequentially with known anticancer agents when a combination formulation is inappropriate.

The compounds of formula (I) of the present invention, suitable for administration to a mammal, e.g., to humans, can be administered by the usual routes and the dosage level depends upon the age, weight, conditions of the patient and administration route.

For example, a suitable dosage adopted for oral administration of a compound of formula (I) may range from about 10 to about 1000 mg per dose, from 1 to 5 times daily. The compounds of the invention can be administered in a variety of dosage forms, e.g., orally, in the form tablets, capsules, sugar or film coated tablets, liquid solutions or suspensions; rectally in the form suppositories; parenterally, e.g., intramuscularly, or through intravenous and/or intrathecal and/or intraspinal injection or infusion.

The present invention also includes pharmaceutical compositions comprising a compound of formula (I) or a pharmaceutically acceptable salt thereof in association with a pharmaceutically acceptable excipient, which may be a carrier or a diluent.

The pharmaceutical compositions containing the compounds of the invention are usually prepared following conventional methods and are administered in a suitable pharmaceutical form. For example, the solid oral forms may contain, together with the active compound, diluents, e.g., lactose, dextrose saccharose, sucrose, cellulose, corn starch or potato starch; lubricants, e.g., silica, talc, stearic acid, magnesium or calcium stearate, and/or polyethylene glycols; binding agents, e.g., starches, arabic gum, gelatine methylcellulose, carboxymethylcellulose or polyvinyl pyrrolidone; disintegrating agents, e.g., starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. These pharmaceutical preparations may be manufactured in known manner, for example, by means of mixing, granulating, tabletting, sugar-coating, or film-coating processes.

The liquid dispersions for oral administration may be, e.g., syrups, emulsions and suspensions. As an example, the syrups may contain, as carrier, saccharose or saccharose with glycerine and/or mannitol and sorbitol.

The suspensions and the emulsions may contain, as examples of carriers, natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g., sterile water, olive oil, ethyl oleate, glycols, e.g., propylene glycol and, if desired, a suitable amount of lidocaine hydrochloride.

The solutions for intravenous injections or infusions may contain, as a carrier, sterile water or preferably they may be in the form of sterile, aqueous, isotonic, saline solutions or they may contain propylene glycol as a carrier.

The suppositories may contain, together with the active compound, a pharmaceutically acceptable carrier, e.g., cocoa butter, polyethylene glycol, a polyoxyethylene sorbitan fatty acid ester surfactant or lecithin.

With the aim of better illustrating the present invention, without posing any limitation to it, the following examples are now given.

EXPERIMENTAL SECTION

For a reference to any specific compound of formula (I) of the invention, optionally in the form of a pharmaceutically acceptable salt, see the experimental section and claims. Referring to the examples that follow, compounds of the present invention were synthesized using the methods described herein, or other methods, which are well known in the art.

In the examples below, the short forms and abbreviations used herein have the following meaning.

| ABBREVIATIONS | |
|---|---|
| EtOAc | Ethyl acetate |
| DCM | Dichloromethane |
| DIPEA | N,N-Diisopropylethylamine |

ABBREVIATIONS

| | |
|---|---|
| DMF | N,N-dimethylformamide |
| DMSO | Dimethyl sulfoxide |
| $Et_2O$ | Diethyl ether |
| EtOH | Ethanol |
| HCl | Hydrochloric acid |
| $K_2CO_3$ | Potassium carbonate |
| LiHMDS | Lithium bis(trimethylsilyl)amide |
| MeOH | Methanol |
| $NaHCO_3$ | Sodium hydrogencarbonate |
| NaOH | Sodium hydroxide |
| $Pd_2(dba)_3$ | Tris(dibenzylideneacetone)dipalladium(0) |
| $SOCl_2$ | Thionyl chloride |
| TBAF | Tetra-n-butylammonium fluoride |
| TEA | Triethylamine |
| TFA | Trifluoroacetic acid |
| THF | Tetrahydrofurane |
| g | Gram |
| mg | Milligram |
| ml | Milliliter |
| μl | Microliter |
| M | Molar |
| mM | Millimolar |
| μM | Micromolar |
| N | Normal |
| mol | Mole |
| mmol | Millimole |
| h | Hour |
| min | Minute |
| r.t. | Room temperature |
| Hz | Hertz |
| MHz | Mega-Hertz |
| CV | Column volume |
| HRMS | High Resolution Mass Spectra |
| ESI | Electrospray ionization |
| HPLC | High-performance liquid chromatography |

With the aim at better illustrating the present invention, without posing any limitation to it, the following examples are now given.

As used herein the symbols and conventions used in the processes, schemes and examples are consistent with those used in the contemporary scientific literature, for example, the *Journal of the American Chemical Society* or the *Journal of Biological Chemistry*.

Unless otherwise noted, all materials were obtained from commercial suppliers, of the best grade and used without further purification. Anhydrous solvent such as DMF, THF, DCM and toluene were obtained from the Aldrich Chemical Company. All reactions involving air- or moisture-sensitive compounds were performed under nitrogen or argon atmosphere.

General Purification and Analytical Methods

Thin-layer chromatography (TLC) was performed on Merck silica gel 60 $F_{254}$ pre-coated plates. Column chromatography was conducted either under medium pressure on silica (Merck silica gel 40-63 μm) or performed by using a Biotage SP1 Flash Purification system with prepacked silica gel cartridges (Biotage or Varian).

$^1$H-NMR spectra were recorded in DMSO-$d_6$ or $CDCl_3$ at a constant temperature of 28° C. on a Varian INOVA 400 spectrometer operating at 400.50 MHz and equipped with a 5 mm z-axis PFG Indirect Detection Probe ($^1H\{^{15}N-^{31}P\}$) and on a Varian Inova 500 spectrometer operating at 499.75 MHz. Residual solvent signal was used as reference (δ=2.50 or 7.27 ppm). Chemical shifts (δ) are reported in parts per million (ppm) and coupling constants (J) in Hz. The following abbreviations are used for multiplicities: s=singlet; bs=broad signal; d=doublet; t=triplet; m=multiplet; dd=doublet of doublets.

Electrospray (ESI) mass spectra were obtained on a Finnigan LCQ ion trap. Unless otherwise specified, all final compounds were homogeneous (purity of not less than 95%), as determined by high-performance liquid chromatography (HPLC). HPLC-UV-MS analyses, used to assess compound purity, were carried out combining the ion trap MS instrument with HPLC system SSP4000 (Thermo Separation Products) equipped with an autosampler LC Pal (CTC Analytics) and UV6000LP diode array detector (UV detection 215-400 nm). Instrument control, data acquisition and processing were performed with the Xcalibur 1.2 software (Finnigan). HPLC chromatography was run at r.t., and 1 mL/min flow rate, using a Waters×Terra RP 18 column (4.6×50 mm; 3.5 μm). Mobile phase A was ammonium acetate 5 mM buffer (pH 5.5 with acetic acid): acetonitrile 90:10, and mobile phase B was ammonium acetate 5 mM buffer (pH 5.5 with acetic acid): acetonitrile 10:90; the gradient was from 0 to 100% B in 7 minutes then hold 100% B for 2 minutes before requilibration.

ESI(+) high resolution mass spectra (HRMS) were obtained on a Waters Q-Tof Ultima directly connected with micro HPLC 1100 Agilent as previously described (Colombo, M.; Riccardi-Sirtori, F.; Rizzo, V.; A fully automated method for accurate mass determination using high-performance liquid chromatography with a quadrupole/orthogonal acceleration time-of-flight mass spectrometer. *Rapid Commun. Mass Spectrom.* 2004, 18, 511-517).

Preparation 1

6-(tert-butyl-dimethyl-silanyloxy)-3-(1,3-dioxo-1,3-dihydro-isoindol-2-yl)-indazole-1-carboxylic acid tert-butyl ester (III)

Scheme 1, Step A)

A solution of 2-[6-(tert-butyl-dimethyl-silanyloxy)-1H-indazol-3-yl]-isoindole-1,3-dione (786 mg, 2 mmol) in dry THF (10 ml) and DIPEA (1.4 ml, 8 mmol), under argon atmosphere, was treated with di-tert-butyl dicarbonate (495 mg, 2.2 mmol) and stirred at r.t. overnight. The solvent was evaporated under reduced pressure and the crude residue purified by flash chromatography over silica gel eluting with hexane/EtOAc 7:3 affording 884 mg (yield: 89%) of the title compound as a white solid.

$^1$H-NMR (400 MHz), δ (ppm, DMSO-$d_6$): 8.09-8.04 (m, 2 H), 8.02-7.96 (m, 2 H), 7.77 (d, J=8.29 Hz, 1 H), 7.55 (d, J=1.95 Hz, 1H), 7.00 (dd, J=2.07, 8.78 Hz, 1H), 1.69 (s, 9H), 1.01 (s, 9H), 0.28 (s, 6H)

ESI (+) MS m/z 494 ($MH^+$)

Preparation 2

3-Amino-6-(tert-butyl-dimethyl-silanyloxy)-indazole-1-carboxylic acid tert-butyl ester (IV)

Scheme 1, Step B)

A solution of 6-(tert-butyl-dimethyl-silanyloxy)-3-(1,3-dioxo-1,3-dihydro-isoindol-2-yl)-indazole-1-carboxylic acid tert-butyl ester (1.17 g, 2.37 mmol) in dry THF (20 ml), under argon atmosphere, was treated with 3.56 ml of 1M hydrazine in THF (3.56 mmol). The mixture was stirred at reflux for 1 h then more 1M hydrazine in THF was added (8 ml). After stirring for additional 2 h at reflux, the reaction mixture was cooled to r.t. and the precipitated solid filtered and washed with THF. The filtrate was evaporated to dryness and the residue purified by flash chromatography over silica gel eluting with DCM/acetone 7:3 affording 785 mg (yield: 91%) of the title compound as a yellowish solid.

$^1$H-NMR (400 MHz), δ (ppm, DMSO-$d_6$): 7.71 (d, J=8.90 Hz, 1 H), 7.37 (bs, 1H), 6.81 (dd, J=2.07, 8.54 Hz, 1H), 6.21 (bs, 2H), 1.59 (s, 9H), 0.99 (s, 9H), 0.23 (s, 6H)

ESI (+) MS m/z 364 (MH$^+$)

Preparation 3

6-(tert-Butyl-dimethyl-silanyloxy)-3-[4-(4-methyl-piperazin-1-yl)-benzoylamino]-indazole-1-carboxylic acid tert-butyl ester Scheme 1, Step C)

To a suspension of 4-(4-methyl-piperazin-1-yl)-benzoic acid (1.64 g, 7.48 mmol) in dry THF (50 ml), under argon atmosphere, at r.t., was added thionyl chloride (1.37 ml, 18.9 mmol) and 3 drops of dry DMF. The reaction mixture was heated to 50° C. and stirred for 5 h then the volatiles were removed under reduced pressure. The residue was taken up in dry toluene (50 ml), re-evaporated and the solid residue dried under high vacuum. The resultant crude 4-(4-methyl-piperazin-1-yl)-benzoyl chloride hydrochloride was suspended in 20 ml of dry THF and treated dropwise at r.t., under argon atmosphere, with a solution of 3-amino-6-(tert-butyl-dimethyl-silanyloxy)-indazole-1-carboxylic acid tert-butyl ester (1.81 g, 4.98 mmol) in 20 ml of dry THF and 2.56 ml of DIPEA (14.96 mmol). The reaction mixture was heated to 50° C. and stirred for 22 h. The volatiles were removed under reduced pressure, the residue diluted with DCM (100 ml) and washed with a saturated solution of NaHCO$_3$ (75 ml). The organic layer was separated, dried over sodium sulfate and evaporated to dryness. The crude residue was purified by flash chromatography over silica gel eluting with DCM/MeOH/30% NH$_3$ 95:5:0.5 affording 1.88 g (yield: 67%) of the title compound.

$^1$H-NMR (400 MHz), δ (ppm, DMSO-$d_6$): 10.95 (s, 1H), 8.03-7.96 (m, 2H), 7.73 (d, J=9.15 Hz, 1 H), 7.51 (d, J=2.07 Hz, 1H), 7.06-7.01 (m, 2H), 6.90 (dd, J=2.19, 8.78 Hz, 1H), 3.34-3.32 (m, 4H), 2.53-2.50 (m, 4H), 2.27 (s, 3H), 1.65 (s, 9H), 1.00 (s, 9H), 0.27 (s, 6H)

ESI (+) MS m/z 566 (MH$^+$)

Preparation 4

6-Hydroxy-3-[4-(4-methyl-piperazin-1-yl)-benzoylamino]-indazole-1-carboxylic acid tert-butyl ester Scheme 1, Step D)

A solution of 6-(tert-butyl-dimethyl-silanyloxy)-3-[4-(4-methyl-piperazin-1-yl)-benzoylamino]-indazole-1-carboxylic acid tert-butyl ester 1.88 g (3.33 mmol) in dry THF (20 ml) was treated with 1M TBAF in THF (4 ml, 4 mmol) and stirred at r.t. for 30 min. Water (20 ml) was then added and the mixture extracted with EtOAc (100 ml). The separated organic layer was dried over sodium sulfate and evaporated to dryness. The residue was purified by flash chromatography over silica gel eluting with DCM/MeOH/30% NH$_3$ 92:8:0.8 affording, after trituration with Et$_2$O, 1.5 g (yield: 100%) of the title compound.

$^1$H-NMR (400 MHz), δ (ppm, DMSO-$d_6$): 10.86 (s, 1H), 10.16 (s, 1H), 8.02-7.94 (m, 2H), 7.65 (d, J=8.78 Hz, 1 H), 7.48 (d, J=1.95 Hz, 1H), 7.05-7.00 (m, 2H), 6.82 (dd, J=2.07, 8.78 Hz, 1H), 3.34-3.32 (m, 4H), 2.55-2.45 (m, 4H), 2.27 (s, 3H), 1.65 (s, 9H)

ESI (+) MS m/z 452 (MH$^+$)

Preparation 5

3-[4-(4-Methyl-piperazin-1-yl)-benzoylamino]-6-(3-phenoxy-benzyloxy)-indazole-1-carboxylic acid tert-butyl ester Scheme 1, Step Ea)

A solution of triphenylphosphine (209 mg, 0.798 mmol) and diisopropyl azodicarboxylate (0.152 ml, 0.732 mmol) in dry DCM (2 ml) was stirred under argon at 4° C. for 15 min. The resultant mixture was then added to a stirred solution of 6-hydroxy-3-[4-(4-methyl-piperazin-1-yl)-benzoylamino]-indazole-1-carboxylic acid tert-butyl ester (100 mg, 0.222 mmol) and (3-phenoxy-phenyl)-methanol (149 mg, 0.732 mmol) in 2 ml of dry DCM, at r.t., under argon. After stirring at r.t. overnight the reaction mixture was adsorbed onto silica gel, dried, loaded into a silica gel chromatographic column and eluted with DCM/MeOH/30% NH$_3$ 95:5:0.5 affording 87 mg (yield: 62%) of the title compound.

ESI (+) MS m/z 634 (MH$^+$)

Operating in an analogous way, the following compounds were obtained:

6-Benzyloxy-3-[4-(4-methyl-piperazin-1-yl)-benzoylamino]-indazole-1-carboxylic acid tert-butyl ester ESI (+) MS m/z 542 (MH$^+$)

3-[4-(4-Methyl-piperazin-1-yl)-benzoylamino]-6-(3-phenyl-prop-2-ynyloxy)-indazole-1-carboxylic acid tert-butyl ester ESI (+) MS m/z 566 (MH$^+$)

6-(1-Benzyl-piperidin-4-yloxy)-3-[4-(4-methyl-piperazin-1-yl)-benzoylamino]-indazole-1-carboxylic acid tert-butyl ester ESI (+) MS m/z 625 (MH$^+$)

3-[4-(4-Methyl-piperazin-1-yl)-benzoylamino]-6-(2-phenoxy-ethoxy)-indazole-1-carboxylic acid tert-butyl ester ESI (+) MS m/z 572 (MH$^+$)

6-(1-Benzyl-piperidin-3-yloxy)-3-[4-(4-methyl-piperazin-1-yl)-benzoylamino]-indazole-1-carboxylic acid tert-butyl ester ESI (+) MS m/z 625 (MH$^+$)

6-(1-Benzyl-pyrrolidin-2-ylmethoxy)-3-[4-(4-methyl-piperazin-1-yl)-benzoylamino]-indazole-1-carboxylic acid tert-butyl ester ESI (+) MS m/z 625 (MH+)

Preparation 6

3-[4-(4-Methyl-piperazin-1-yl)-benzoylamino]-6-phenoxy-indazole-1-carboxylic acid tert-butyl ester Scheme 1, Step Eb)

A mixture of 6-hydroxy-3-[4-(4-methyl-piperazin-1-yl)-benzoylamino]-indazole-1-carboxylic acid tert-butyl ester (110 mg, 0.244 mmol), phenylboronic acid (92 mg, 0.732 mmol), copper diacetate (45 mg, 0.244 mmol) and 4A molecular sieves (200 mg) in 5 ml of DCM was treated with TEA (0.339 ml, 2.44 mmol). After stirring at r.t. for 2 days the solvent was removed under reduced pressure, the residue treated with DCM/MeOH/30% $NH_3$ 95:5:0.5, filtered and the filtrate loaded into a silica gel chromatographic column and eluted with DCM/MeOH/30% $NH_3$ 95:5:0.5 affording 88 mg (yield: 68%) of the title compound.

ESI (+) MS m/z 528 (MH+)

Operating in an analogous way, the following compounds were obtained:

6-(3-Fluoro-phenoxy)-3-[4-(4-methyl-piperazin-1-yl)-benzoylamino]-indazole-1-carboxylic acid tert-butyl ester ESI (+) MS m/z 546 (MH+)

6-(4-Benzyloxy-phenoxy)-3-[4-(4-methyl-piperazin-1-yl)-benzoylamino]-indazole-1-carboxylic acid tert-butyl ester ESI (+) MS m/z 634 (MH+)

3-[4-(4-Methyl-piperazin-1-yl)-benzoylamino]-6-(4-phenoxy-phenoxy)-indazole-1-carboxylic acid tert-butyl ester ESI (+) MS m/z 620 (MH+)

6-(3-Benzyloxy-phenoxy)-3-[4-(4-methyl-piperazin-1-yl)-benzoylamino]-indazole-1-carboxylic acid tert-butyl ester ESI (+) MS m/z 634 (MH+)

Preparation 7

3-Amino-6-hydroxy-indazole-1-carboxylic acid tert-butyl ester (XII)

Scheme 1, Step G)

A solution of 3-amino-6-(tert-butyl-dimethyl-silanyloxy)-indazole-1-carboxylic acid tert-butyl ester 672 mg (1.85 mmol) in dry THF (10 ml) was treated with 1M TBAF in THF (1.85 ml, 1.85 mmol) and stirred at r.t. for 30 min. Water (20 ml) was then added and the mixture extracted with EtOAc (3×50 ml). The separated organic layers were combined, dried over sodium sulfate and evaporated to dryness. The residue was purified by flash chromatography over silica gel eluting with DCM/EtOAc 6:4 affording 429 mg (yield: 93%) of the title compound.

$^1$H-NMR (400 MHz), δ (ppm, DMSO-$d_6$): 9.93 (s, 1H), 7.60 (d, J=8.54 Hz, 1H), 7.35 (bs, 1H), 6.71 (dd, J=2.19, 8.54 Hz, 1H), 6.10 (bs, 2H), 1.58 (s, 9H)

ESI (+) MS m/z 250 (MH+)

Preparation 8

3-Amino-6-(2-benzyloxy-ethoxy)-indazole-1-carboxylic acid tert-butyl ester

Scheme 1, Step Hb)

A mixture of 3-amino-6-hydroxy-indazole-1-carboxylic acid tert-butyl ester (249 mg, 1 mmol), $K_2CO_3$ (152 mg, 1.1 mmol) and benzyl 2-bromoethyl ether (0.179 ml, 1.1 mmol) in dry DMF (5 ml) was stirred at 50° C. for 12 h. More benzyl 2-bromoethyl ether (30 μl) was added and the mixture stirred at 50° C. for additional 4 h. The reaction mixture was poured into water (50 ml) and extracted with EtOAc (50 ml). The organic layer wad dried over sodium sulfate and evaporated to dryness. The crude residue was purified by flash chromatography over silica gel eluting with DCM/EtOAc 7:3 affording 274 mg (yield: 72%) of the title compound.

$^1$H-NMR (400 MHz), δ (ppm, DMSO-$d_6$): 7.71 (d, J=8.66 Hz, 1H), 7.48 (bs, 1H), 7.38-7.27 (m, 5H), 6.91 (dd, J=2.19, 8.66 Hz, 1H), 6.19 (bs, 2H), 4.59 (s, 2H), 4.25-4.20 (m, 2H), 3.85-3.80 (m, 2H), 1.58 (s, 9H)

ESI (+) MS m/z 384 (MH+)

Preparation 9

6-(2-Benzyloxy-ethoxy)-3-[4-(4-methyl-piperazin-1-yl)-benzoylamino]-indazole-1-carboxylic acid tert-butyl ester Scheme 1, Step I)

A mixture of 4-(4-methyl-piperazin-1-yl)-benzoyl chloride hydrochloride, prepared from 248 mg (1.13 mmol) of 4-(4-methyl-piperazin-1-yl)-benzoic acid as described above in preparation 3, and DIPEA (0.386 ml, 2.25 mmol) in dry THF (10 ml) was treated dropwise at r.t., under argon atmosphere, with a solution of 3-amino-6-(2-benzyloxy-ethoxy)-indazole-1-carboxylic acid tert-butyl ester (143 mg, 0.374 mmol) in 10 ml of dry THF. The reaction mixture was heated up to 50° C. and stirred for 12 h. The volatiles were removed under reduced pressure, the residue taken up in DCM (100 ml) and washed with a saturated solution of $NaHCO_3$ (75 ml). The organic layer was separated, dried over sodium sulfate and evaporated to dryness and the crude residue purified by flash chromatography over silica gel eluting with DCM/MeOH 98:2 then 90:10 affording 124 mg (yield: 57%) of the title compound as a white solid.

$^1$H-NMR (400 MHz), δ (ppm, DMSO-d$_6$): 10.94 (s, 1H), 8.02-7.96 (m, 2H), 7.75 (d, J=8.90 Hz, 1 H), 7.61 (d, J=2.19 Hz, 1H), 7.39-7.27 (m, 5H), 7.06-7.01 (m, 2H), 7.00 (dd, J=2.19, 8.90 Hz, 1H), 4.60 (s, 2H), 4.31-4.25 (m, 2H), 3.88-3.83 (m, 2H), 3.34-3.32 (m, 4H), 2.53-2.46 (m, 4H), 2.27 (s, 3H), 1.66 (s, 9H)

ESI (+) MS m/z 586 (MH$^+$)

Example 1

4-(4-Methyl-piperazin-1-yl)-N-[6-(3-phenoxy-benzyloxy)-1H-indazol-3-yl]-benzamide (Cpd. 5)

Scheme 1, Step F)

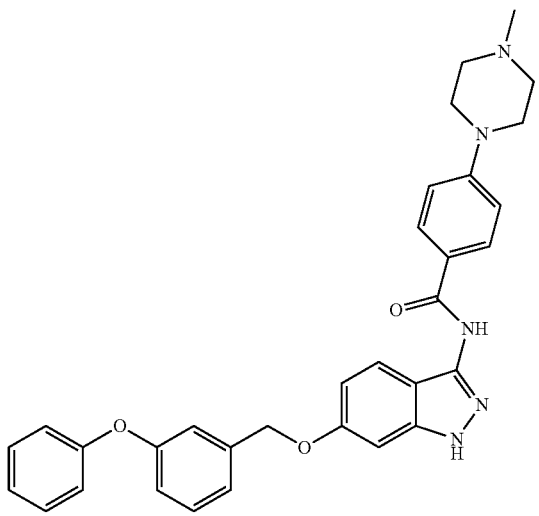 [SMILES: CN1CCN(c2ccc(C(=O)Nc3n[nH]c4cc(OCc5cccc(Oc6ccccc6)c5)ccc34)cc2)CC1]

A solution of 3-[4-(4-methyl-piperazin-1-yl)-benzoylamino]-6-(3-phenoxy-benzyloxy)-indazole-1-carboxylic acid tert-butyl ester (87 mg, 0.137 mmol) in DCM/TFA 8:2 (5 ml) was stirred at r.t. for 2 h. The volatiles were removed under reduced pressure and the residue purified by flash chromatography over silica gel eluting with DCM/MeOH/30% NH$_3$ 90:10:1 affording 71 mg (yield: 97%) of the title compound as a white solid.

$^1$H-NMR (400 MHz), δ (ppm, DMSO-d$_6$): 12.46 (s, 1 H) 10.38 (s, 1 H) 7.94 (d, J=8.97 Hz, 2 H) 7.59 (d, J=8.79 Hz, 1 H) 7.30-7.43 (m, 3 H) 7.25 (d, J=7.69 Hz, 1 H) 7.07-7.17 (m, 2 H) 6.97-7.04 (m, 4 H) 6.95 (dd, J=8.06, 1.83 Hz, 1 H) 6.90 (d, J=2.01 Hz, 1 H) 6.75 (dd, J=8.88, 2.11 Hz, 1 H) 5.18 (s, 2 H) 3.25-3.32 (m, 4 H) 2.42-2.48 (m, 4 H) 2.23 (s, 3 H)

ESI (+) MS m/z 534 (MH$^+$)

ESI (+) HRMS calcd for C$_{32}$H$_{31}$N$_5$O$_3$+H$^+$: 534.2500; found 534.2488

Operating in an analogous way, the following compounds were obtained:

N-(6-Benzyloxy-1H-indazol-3-yl)-4-(4-methyl-piperazin-1-yl)-benzamide (Cpd. 1)

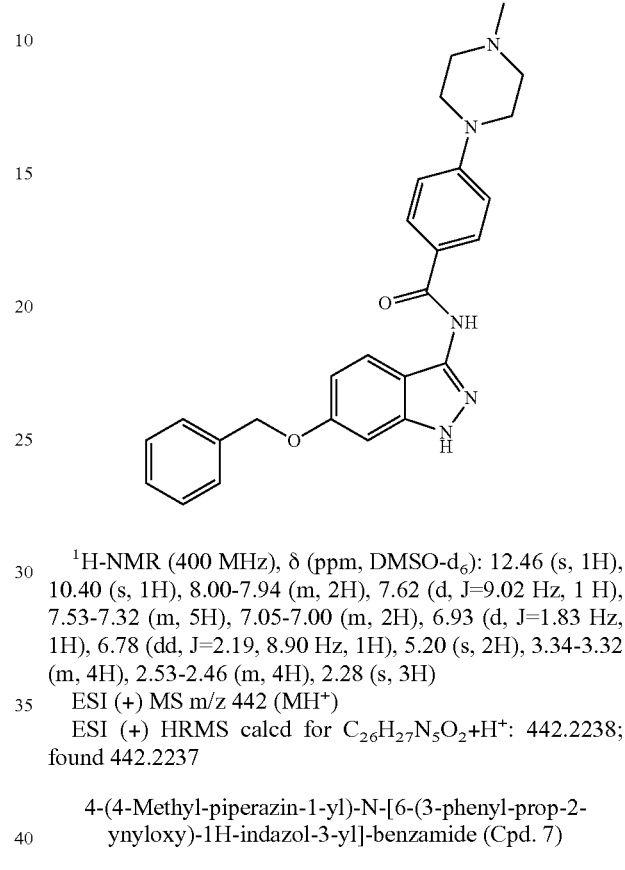

$^1$H-NMR (400 MHz), δ (ppm, DMSO-d$_6$): 12.46 (s, 1H), 10.40 (s, 1H), 8.00-7.94 (m, 2H), 7.62 (d, J=9.02 Hz, 1 H), 7.53-7.32 (m, 5H), 7.05-7.00 (m, 2H), 6.93 (d, J=1.83 Hz, 1H), 6.78 (dd, J=2.19, 8.90 Hz, 1H), 5.20 (s, 2H), 3.34-3.32 (m, 4H), 2.53-2.46 (m, 4H), 2.28 (s, 3H)

ESI (+) MS m/z 442 (MH$^+$)

ESI (+) HRMS calcd for C$_{26}$H$_{27}$N$_5$O$_2$+H$^+$: 442.2238; found 442.2237

4-(4-Methyl-piperazin-1-yl)-N-[6-(3-phenyl-prop-2-ynyloxy)-1H-indazol-3-yl]-benzamide (Cpd. 7)

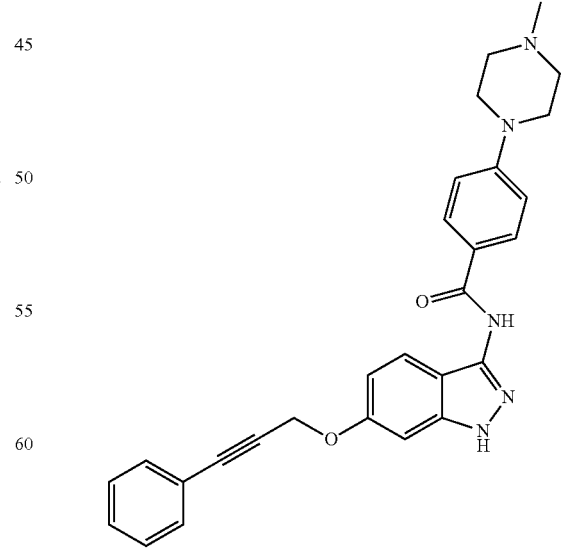

$^1$H-NMR (400 MHz), δ (ppm, DMSO-d$_6$): 12.53 (s, 1H), 10.42 (s, 1H), 8.00-7.95 (m, 2H), 7.64 (d, J=8.90 Hz, 1 H), 7.50-7.37 (m, 5H), 7.06-7.00 (m, 3H), 6.78 (dd, J=2.19, 9.02 Hz, 1H), 5.13 (s, 2H), 3.34-3.32 (m, 4H), 2.53-2.46 (m, 4H), 2.28 (s, 3H)

ESI (+) MS m/z 466 (MH+)

ESI (+) HRMS calcd for $C_{28}H_{27}N_5O_2+H^+$: 466.2237; found 466.2255

N-[6-(1-Benzyl-piperidin-4-yloxy)-1H-indazol-3-yl]-4-(4-methyl-piperazin-1-yl)-benzamide (Cpd. 6)

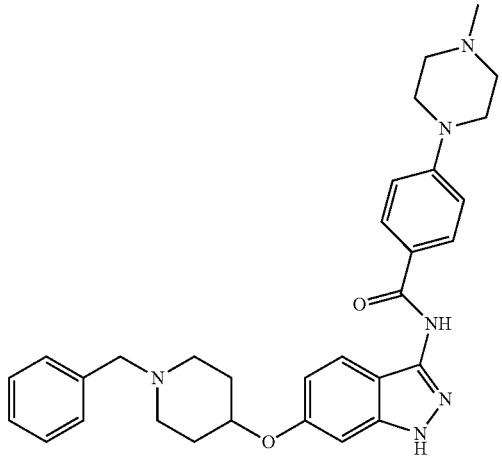 [SMILES: CN1CCN(c2ccc(C(=O)Nc3n[nH]c4cc(OC5CCN(Cc6ccccc6)CC5)ccc34)cc2)CC1]

$^1$H-NMR (400 MHz), δ (ppm, DMSO-d$_6$): 12.38 (s, 1H), 10.39 (s, 1H), 7.99-7.94 (m, 2H), 7.59 (d, J=8.90 Hz, 1 H), 7.38-7.24 (m, 5H), 7.04-6.99 (m, 2H), 6.88 (d, J=2.07 Hz, 1H), 6.71 (dd, J=2.07, 8.90 Hz, 1H), 4.52-4.44 (m, 1H), 3.53 (s, 2H), 3.34-3.32 (m, 4H), 2.78-2.65 (m, 2H), 2.53-2.46 (m, 4H), 2.37-2.23 (m, 5H), 2.05-1.94 (m, 2H), 1.77-1.64 (m, 2H)

ESI (+) MS m/z 525 (MH+)

ESI (+) HRMS calcd for $C_{31}H_{36}N_6O_2+H^+$: 525.2972; found 525.2988

4-(4-Methyl-piperazin-1-yl)-N-[6-(2-phenoxy-ethoxy)-1H-indazol-3-yl]-benzamide (Cpd. 10)

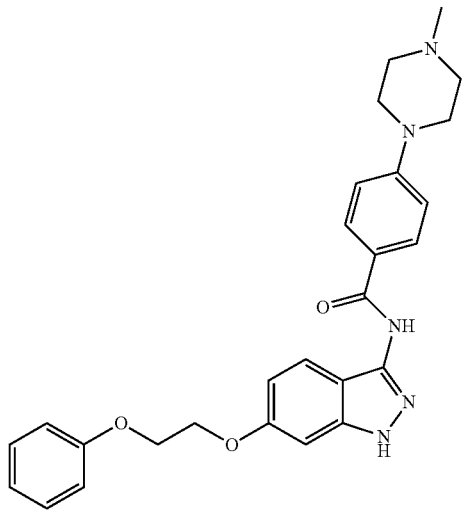 [SMILES: CN1CCN(c2ccc(C(=O)Nc3n[nH]c4cc(OCCOc5ccccc5)ccc34)cc2)CC1]

$^1$H-NMR (400 MHz), δ (ppm, DMSO-d$_6$): 12.49 (s, 1H), 10.40 (s, 1H), 7.99-7.95 (m, 2H), 7.62 (d, J=8.90 Hz, 1 H), 7.37-7.29 (m, 2H), 7.05-7.00 (m, 4H), 7.00-6.94 (m, 1H), 6.92 (d, J=2.07 Hz, 1H), 6.74 (dd, J=2.07, 8.90 Hz, 1H), 4.41-4.36 (m, 4H), 3.35-3.30 (m, 4H), 2.52-2.46 (m, 4H), 2.27 (s, 3H)

ESI (+) MS m/z 472 (MH+)

ESI (+) HRMS calcd for $C_{27}N_5O_3H_{29}+H^+$: 472.2343; found 472.2357

N-[6-(1-Benzyl-piperidin-3-yloxy)-1H-indazol-3-yl]-4-(4-methyl-piperazin-1-yl)-benzamide (Cpd. 12)

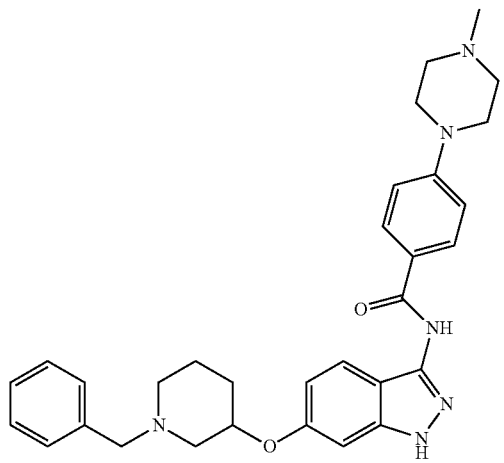 [SMILES: CN1CCN(c2ccc(C(=O)Nc3n[nH]c4cc(OC5CCCN(Cc6ccccc6)C5)ccc34)cc2)CC1]

1H-NMR (400 MHz), δ (ppm, DMSO-d$_6$): 12.37 (s, 1H), 10.38 (s, 1H), 7.99-7.93 (m, 2H), 7.58 (d, J=8.90 Hz, 1 H), 7.36-7.22 (m, 5H), 7.05-6.98 (m, 2H), 6.86 (d, J=1.83 Hz, 1H), 6.68 (dd, J=2.20, 8.90 Hz, 1H), 4.51-4.42 (m, 1H), 3.55 (s, 2H), 3.35-3.30 (m, 4H), 3.02-2.95 (m, 1H), 2.70-2.62 (m, 1H), 2.49-2.43 (m, 4H), 2.27 (s, 3H), 2.20-2.02 (m, 3H), 1.81-1.71 (m, 1H), 1.65-1.53 (m, 1H), 1.48-1.36 (m, 1H)

ESI (+) MS m/z 525 (MH+)

ESI (+) HRMS calcd for $C31N6O2H36+H^+$: 525.2972; found 525.2975

N-[6-(1-Benzyl-pyrrolidin-2-ylmethoxy)-1H-indazol-3-yl]-4-(4-methyl-piperazin-1-yl)-benzamide (Cpd. 13)

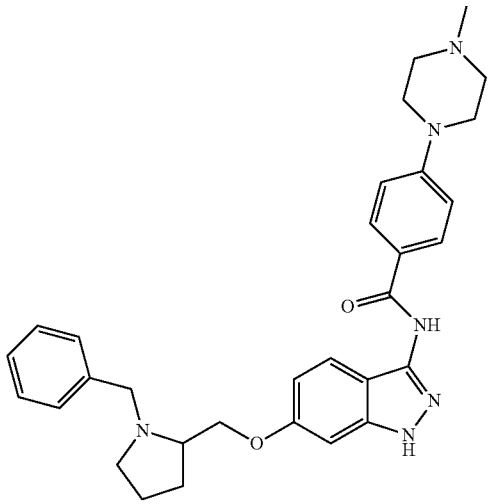 [SMILES: CN1CCN(c2ccc(C(=O)Nc3n[nH]c4cc(OCC5CCCN5Cc5ccccc5)ccc34)cc2)CC1]

¹H-NMR (400 MHz), δ (ppm, DMSO-d₆): 12.43 (s, 1H), 10.39 (s, 1H), 7.99-7.93 (m, 2H), 7.59 (d, J=8.90 Hz, 1 H), 7.38-7.21 (m, 5H), 7.04-6.99 (m, 2H), 6.83 (d, J=1.95 Hz, 1H), 6.69 (dd, J=2.07, 8.90 Hz, 1H), 4.17 (d, J=13.17 Hz, 1H), 4.04 (dd, J=5.49, 9.63 Hz, 1H), 3.90 (dd, J=6.58, 9.63 Hz, 1H), 3.49 (d, J=13.17 Hz, 1H), 3.35-3.26 (m, 5H), 3.06-2.98 (m, 1H), 2.88-2.83 (m, 1H), 2.49-2.44 (m, 4H), 2.32-2.24 (m, 1H), 2.24 (s, 3H), 2.07-1.96 (m, 1H), 1.76-1.66 (m, 2H)

ESI (+) MS m/z 525 (MH⁺)

ESI (+) HRMS calcd for $C_{31}N_6O_2H_{36}$+H⁺: 525.2972; found 525.2969

4-(4-Methyl-piperazin-1-yl)-N-(6-phenoxy-1H-indazol-3-yl)-benzamide (Cpd. 2)

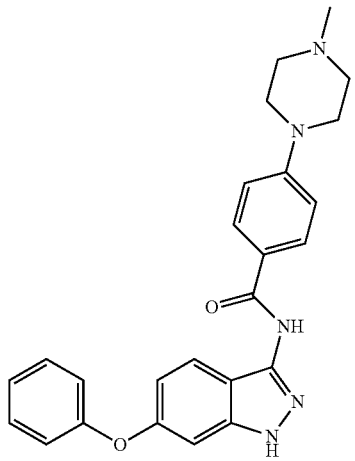 [SMILES: CN1CCN(c2ccc(C(=O)Nc3n[nH]c4cc(Oc5ccccc5)ccc34)cc2)CC1]

¹H-NMR (400 MHz), δ (ppm, DMSO-d₆): 12.57 (s, 1H), 10.54 (s, 1H), 8.06-7.99 (m, 2H), 7.74 (d, J=8.78 Hz, 1 H), 7.48-7.40 (m, 2H), 7.23-7.17 (m, 1H), 7.13-7.06 (m, 4H), 6.90 (d, J=2.07 Hz, 1H), 6.84 (dd, J=2.07, 8.90 Hz, 1H), 3.35-3.00 (m, 8H), 2.74 (s, 3H)

ESI (+) MS m/z 428 (MH⁺)

ESI (+) HRMS calcd for $C_{25}N_5O_2H_{25}$+H⁺: 428.2081; found 428.2092

N-[6-(3-Fluoro-phenoxy)-1H-indazol-3-yl]-4-(4-methyl-piperazin-1-yl)-benzamide (Cpd. 3)

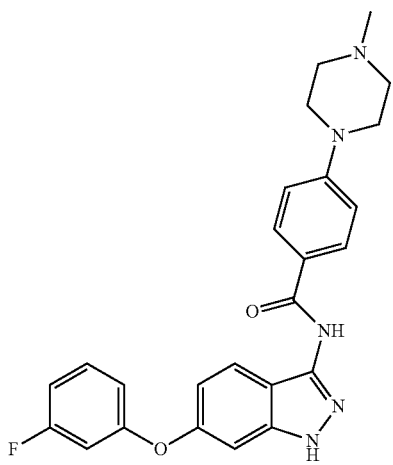 [SMILES: CN1CCN(c2ccc(C(=O)Nc3n[nH]c4cc(Oc5cccc(F)c5)ccc34)cc2)CC1]

¹H-NMR (400 MHz), δ (ppm, DMSO-d₆): 12.64 (s, 1H), 10.53 (s, 1H), 8.03-7.98 (m, 2H), 7.77 (d, J=8.78 Hz, 1 H), 7.49-7.41 (m, 1H), 7.10-6.88 (m, 6H), 6.86 (dd, J=2.07, 8.78 Hz, 1H), 3.35-3.24 (m, 4H), 2.90-2.65 (m, 4H), 2.47 (bs, 3H)

ESI (+) MS m/z 446 (MH⁺)

ESI (+) HRMS calcd for $C_{25}N_5O_2FH_{24}$+H⁺: 446.1987; found 446.1981

N-[6-(4-Benzyloxy-phenoxy)-1H-indazol-3-yl]-4-(4-methyl-piperazin-1-yl)-benzamide (Cpd. 4)

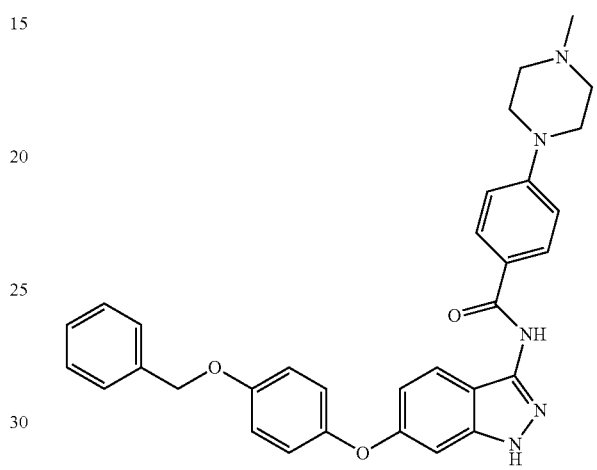

¹H-NMR (400 MHz), δ (ppm, DMSO-d₆): 12.46 (s, 1H), 10.47 (s, 1H), 8.01-7.96 (m, 2H), 7.70 (d, J=8.90 Hz, 1 H), 7.52-7.32 (m, 5H), 7.15-7.00 (m, 6H), 6.81 (dd, J=2.19, 8.90 Hz, 1H), 6.74 (d, J=2.19 Hz, 1H), 5.13 (s, 2H), 3.35-3.30 (m, 4H), 2.70-2.55 (m, 4H), 2.38 (bs, 3H)

ESI (+) MS m/z 534 (MH⁺)

ESI (+) HRMS calcd for $C_{32}N_5O_3H_{31}$+H⁺: 534.2500; found 534.2498

4-(4-Methyl-piperazin-1-yl)-N-[6-(4-phenoxy-phenoxy)-1H-indazol-3-yl]-benzamide (Cpd. 8)

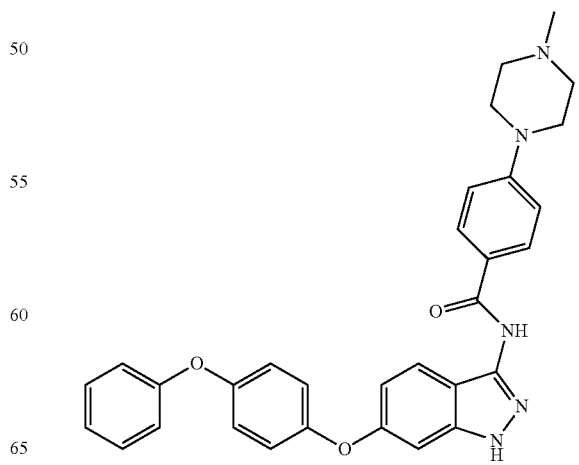

¹H-NMR (400 MHz), δ (ppm, DMSO-d₆): 12.53 (s, 1H), 10.48 (s, 1H), 8.01-7.96 (m, 2H), 7.74 (d, J=8.78 Hz, 1 H), 7.45-7.39 (m, 2H), 7.19-6.99 (m, 9H), 6.89 (d, J=2.07 Hz, 1H), 6.85 (dd, J=2.07, 8.78 Hz, 1H), 3.35-3.30 (m, 4H), 2.52-2.47 (m, 4H), 2.28 (bs, 3H)

ESI (+) MS m/z 520 (MH⁺)

ESI (+) HRMS calcd for $C_{31}N_5O_3H_{29}+H^+$: 520.2343; found 520.2346

N-[6-(3-Benzyloxy-phenoxy)-1H-indazol-3-yl]-4-(4-methyl-piperazin-1-yl)-benzamide (Cpd. 9)

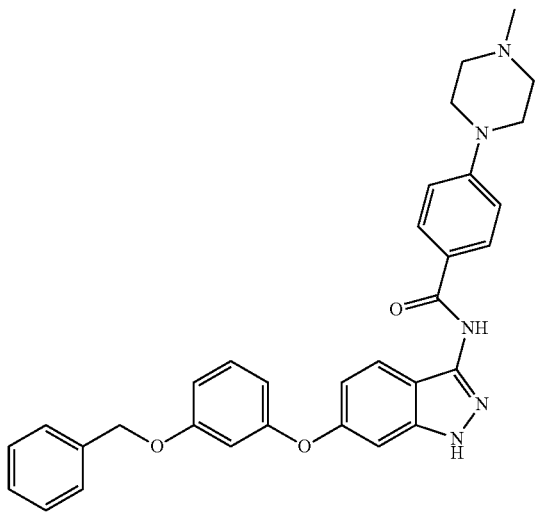 [SMILES: CN1CCN(c2ccc(C(=O)Nc3n[nH]c4cc(Oc5cccc(OCc6ccccc6)c5)ccc34)cc2)CC1]

¹H-NMR (400 MHz), δ (ppm, DMSO-d₆): 12.58 (s, 1H), 10.54 (s, 1H), 8.05-7.99 (m, 2H), 7.74 (d, J=8.90 Hz, 1 H), 7.47-7.29 (m, 6H), 7.12-7.06 (m, 2H), 6.93 (d, J=1.95 Hz, 1H), 6.87-6.81 (m, 2H), 6.76-6.73 (m, 1H), 6.65 (dd, J=2.19, 8.17 Hz, 1H), 5.11 (s, 2H), 3.35-2.80 (m, 8H), 2.65 (bs, 3H)

ESI (+) MS m/z 534 (MH⁺)

ESI (+) HRMS calcd for $C_{32}N_5O_3H_{31}+H^+$: 534.2500; found 534.2501

N-[6-(2-Benzyloxy-ethoxy)-1H-indazol-3-yl]-4-(4-methyl-piperazin-1-yl)-benzamide (Cpd. 11)

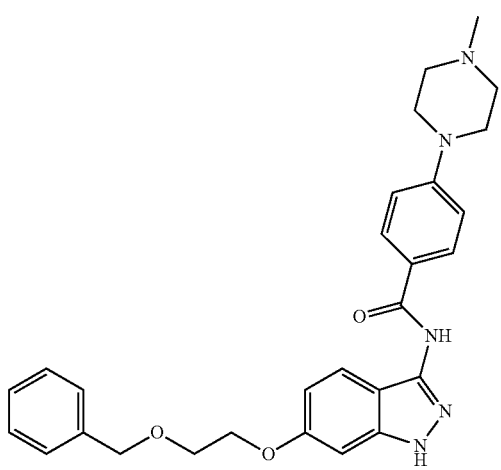 [SMILES: CN1CCN(c2ccc(C(=O)Nc3n[nH]c4cc(OCCOCc5ccccc5)ccc34)cc2)CC1]

¹H-NMR (400 MHz), δ (ppm, DMSO-d₆): 12.44 (s, 1 H) 10.38 (s, 1 H) 7.95 (d, J=9.03 Hz, 2 H) 7.59 (d, J=8.91 Hz, 1 H) 7.32-7.42 (m, 4 H) 7.23-7.32 (m, 1 H) 7.00 (d, J=9.03 Hz, 2 H) 6.85 (d, J=1.95 Hz, 1 H) 6.71 (dd, J=8.91, 2.07 Hz, 1 H) 4.58 (s, 2 H) 4.08-4.31 (m, 2 H) 3.72-3.92 (m, 2 H) 3.20-3.30 (m, 4H) 2.40-2.48 (m, 4 H) 2.23 (s, 3 H)

ESI (+) MS m/z 486 (MH⁺)

ESI (+) HRMS calcd for $C_{28}N_5O_3H_{31}+H^+$: 486.2500; found 486.2502

Preparation 10

4-(2-Benzyloxy-ethoxy)-2-fluoro-benzonitrile

Scheme 2, Step Jc)

A mixture of 2-fluoro-4-hydroxy-benzonitrile (4.57 g, 33.3 mmol), K₂CO₃ (13.8 g, 99.9 mmol) and benzyl 2-bromoethyl ether (5.79 ml, 36.6 mmol) in dry DMF (15 ml) was stirred at 70° C. for 6 h. The reaction mixture was cooled to r.t., poured into 300 ml of water and extracted with EtOAc (2×100 ml). The organic layers were combined, dried over sodium sulfate and evaporated to dryness. The crude residue was purified by chromatography (Biotage SP1 Flash Purification system) on a silica gel cartridge (Biotage SNAP 100 g) eluting with a gradient from hexane/EtOAc 100:0 to 60:40 over 20 CV, affording 8.79 g (yield: 97%) of the title compound as a colourless oil.

¹H-NMR (400 MHz), δ (ppm, DMSO-d₆): 7.75-7.90 (m, 1 H) 7.26-7.38 (m, 5 H) 7.19 (dd, J=11.96, 2.44 Hz, 1 H) 6.99 (dd, J=8.79, 2.32 Hz, 1 H) 4.55 (s, 2 H) 4.22-4.34 (m, 2 H) 3.65-3.87 (m, 2 H)

ESI (+) MS m/z 272 (MH⁺)

Operating in an analogous way, the following compounds were obtained:

2-Fluoro-4-[2-(4-trifluoromethyl-benzyloxy)-ethoxy]-benzonitrile

¹H-NMR (400 MHz), δ (ppm, DMSO-d₆): 7.82 (t, J=8.33 Hz, 1 H) 7.71 (d, J=8.06 Hz, 2 H) 7.55 (d, J=7.88 Hz, 2 H) 7.19 (dd, J=12.00, 2.29 Hz, 1 H) 7.00 (dd, J=8.70, 2.29 Hz, 1 H) 4.66 (s, 2 H) 4.28-4.31 (m, 2 H) 3.79-3.84 (m, 2 H)

ESI (+) MS m/z 340 (MH⁺)

ESI (+) HRMS calcd for $C_{17}H_{13}F_4NO_2+Na^+$: 362.0774; found 362.0771

2-Fluoro-4-[2-(4-fluoro-benzyloxy)-ethoxy]-benzonitrile

¹H-NMR (400 MHz), δ (ppm, DMSO-d₆): 7.82 (t, J=8.43 Hz, 1 H) 7.31-7.40 (m, 2 H) 7.13-7.23 (m, 3 H) 6.99 (dd, J=8.79, 2.20 Hz, 1 H) 4.53 (s, 2 H) 4.25-4.29 (m, 2 H) 3.75-3.79 (m, 2 H)

ESI (+) MS m/z 290 (MH⁺)

ESI (+) HRMS calcd for $C_{16}H_{13}F_2NO_2+Na^+$: 312.0806; found 312.0812

2-Fluoro-4-[2-(3-trifluoromethyl-benzyloxy)-ethoxy]-benzonitrile

¹H-NMR (400 MHz), δ (ppm, DMSO-d₆): 7.79-7.85 (m, 1 H) 7.55-7.67 (m, 4 H) 7.18 (dd, J=11.96, 2.32 Hz, 1 H) 6.99 (dd, J=8.79, 2.44 Hz, 1 H) 4.65 (s, 2 H) 4.29-4.34 (m, 2 H) 3.80-3.85 (m, 2 H)

ESI (+) MS m/z 340 (MH⁺)

ESI (+) HRMS calcd for $C_{17}H_{13}F_4NO_2+H^+$: 340.0955; found 340.0948

2-Fluoro-4-[2-(2-fluoro-benzyloxy)-ethoxy]-benzonitrile $^1$H-NMR (400 MHz), δ (ppm, DMSO-d$_6$): 7.82 (t, J=8.33 Hz, 1 H) 7.44 (td, J=7.65, 1.74 Hz, 1 H) 7.33-7.39 (m, 1 H) 7.15-7.23 (m, 3 H) 6.98 (dd, J=8.79, 2.20 Hz, 1 H) 4.60 (s, 2 H) 4.26-4.30 (m, 2 H) 3.79-3.83 (m, 2 H)
ESI (+) MS m/z 290 (MH$^+$)
ESI (+) HRMS calcd for C$_{16}$H$_{13}$F$_2$NO$_2$+H$^+$: 290.0987; found 290.0995

2-Fluoro-4-[2-(4-methoxy-benzyloxy)-ethoxy]-benzonitrile $^1$H-NMR (400 MHz), δ (ppm, DMSO-d$_6$): 7.81 (dd, J=8.61, 8.06 Hz, 1 H) 7.21-7.31 (m, 2 H) 7.18 (dd, J=11.90, 2.38 Hz, 1 H) 6.98 (dd, J=8.79, 2.38 Hz, 1 H) 6.85-6.91 (m, 2 H) 4.46 (s, 2 H) 4.21-4.31 (m, 2 H) 3.63-3.81 (m, 5 H)
ESI (+) MS m/z 302 (MH$^+$)
ESI (+) HRMS calcd for C$_{17}$H$_{16}$FNO$_3$+Na$^+$: 324.1006; found 324.1008

2-Fluoro-4-[2-(pyridin-4-ylmethoxy)-ethoxy]-benzonitrile $^1$H-NMR (400 MHz), δ (ppm, DMSO-d$_6$): 8.50-8.54 (m, 2 H) 7.83 (t, J=8.33 Hz, 1 H) 7.32 (d, J=5.49 Hz, 2 H) 7.20 (dd, J=11.91, 2.20 Hz, 1 H) 7.01 (dd, J=8.79, 2.38 Hz, 1 H) 4.61 (s, 2 H) 4.30-4.33 (m, 2 H) 3.81-3.84 (m, 2 H)
ESI (+) MS m/z 273 (MH$^+$)
ESI (+) HRMS calcd for C$_{15}$H$_{13}$FN$_2$O$_2$+H$^+$: 273.1034; found 273.1031

2-Fluoro-4-((E)-3-phenyl-allyloxy)-benzonitrile $^1$H-NMR (400 MHz), δ (ppm, DMSO-d$_6$): 7.84 (t, J=8.33 Hz, 1 H) 7.44-7.53 (m, 2 H) 7.36 (t, J=7.60 Hz, 2 H) 7.26-7.31 (m, 1 H) 7.23 (dd, J=11.90, 2.38 Hz, 1 H) 7.04 (dd, J=8.79, 2.38 Hz, 1 H) 6.80 (d, J=15.93 Hz, 1 H) 6.50 (dt, J=15.93, 6.04 Hz, 1 H) 4.86 (dd, J=6.04, 1.10 Hz, 2 H)
ESI (+) MS m/z 254 (MH$^+$)
ESI (+) HRMS calcd for C$_{16}$H$_{12}$FNO+Na$^+$: 276.0795; found 276.0795

Preparation 11

6-(2-Benzyloxy-ethoxy)-1H-indazol-3-ylamine

Scheme 2, Step K)
A mixture of 4-(2-benzyloxy-ethoxy)-2-fluoro-benzonitrile (8.79 g, 32.4 mmol) and hydrazine monohydrate (4.72 ml, 97.2 mmol) in n-butanol (15 ml) was stirred at 120° C. for 8 h. The reaction mixture was cooled to r.t., treated with 250 ml of water and stirred for 30 min. The precipitated solid was filtered, washed with water and dried in oven at 50° C. under high vacuum, affording 9.0 g of the title compound as white crystals (yield: 98%).

$^1$H-NMR (400 MHz), δ (ppm, DMSO-d$_6$): 11.13 (s, 1H) 7.52 (d, J=8.67 Hz, 1 H) 7.33-7.38 (m, 4 H) 7.25-7.32 (m, 1 H) 6.64 (d, J=1.83 Hz, 1 H) 6.54 (dd, J=8.67, 2.07 Hz, 1 H) 5.26 (bs, 2 H) 4.57 (s, 2 H) 4.12-4.16 (m, 2 H) 3.77-3.80 (m, 2 H)
ESI (+) MS m/z 284 (MH$^+$)

Operating in an analogous way, the following compounds were obtained:

6-[2-(4-Trifluoromethyl-benzyloxy)-ethoxy]-1H-indazol-3-ylamine $^1$H-NMR (400 MHz), δ (ppm, DMSO-d$_6$): 11.12 (s, 1 H) 7.72 (d, J=8.06 Hz, 2 H) 7.58 (d, J=8.06 Hz, 2 H) 7.52 (d, J=8.79 Hz, 1 H) 6.65 (d, J=1.83 Hz, 1 H) 6.55 (dd, J=8.70, 2.11 Hz, 1 H) 5.19 (s, 2 H) 4.68 (s, 2 H) 4.14-4.19 (m, 2 H) 3.81-3.85 (m, 2 H)
ESI (+) MS m/z 352 (MH$^+$)
ESI (+) HRMS calcd for C$_{17}$H$_{16}$F$_3$N$_3$O$_2$+H$^+$: 352.1268; found 352.1278

6-[2-(4-Fluoro-benzyloxy)-ethoxy]-1H-indazol-3-ylamine $^1$H-NMR (400 MHz), δ (ppm, DMSO-d$_6$): 11.12 (s, 1 H) 7.52 (d, J=8.79 Hz, 1 H) 7.39 (dd, J=8.52, 5.77 Hz, 2 H) 7.14-7.20 (m, 2 H) 6.64 (d, J=2.01 Hz, 1 H) 6.53 (dd, J=8.70, 2.11 Hz, 1 H) 5.19 (s, 2 H) 4.55 (s, 2 H) 4.10-4.15 (m, 2 H) 3.76-3.80 (m, 2 H)
ESI (+) MS m/z 302 (MH$^+$)
ESI (+) HRMS calcd for C$_{16}$H$_{16}$FN$_3$O$_2$+H$^+$: 302.1300; found 302.1306

6-[2-(3-Trifluoromethyl-benzyloxy)-ethoxy]-1H-indazol-3-ylamine $^1$H-NMR (400 MHz), δ (ppm, DMSO-d$_6$): 11.13 (s, 1 H) 7.71 (s, 1 H) 7.57-7.69 (m, 3 H) 7.48-7.54 (m, 1 H) 6.65 (d, J=1.95 Hz, 1 H) 6.54 (dd, J=8.79, 2.07 Hz, 1 H) 5.21 (br. s., 2 H) 4.68 (s, 2 H) 4.13-4.19 (m, 2 H) 3.80-3.87 (m, 2H)
ESI (+) MS m/z 352 (MH$^+$)
ESI (+) HRMS calcd for C$_{17}$H$_{16}$F$_3$N$_3$O$_2$+H$^+$: 352.1268; found 352.1274

6-[2-(2-Fluoro-benzyloxy)-ethoxy]-1H-indazol-3-ylamine $^1$H-NMR (400 MHz), δ (ppm, DMSO-d$_6$): 11.12 (s, 1 H) 7.52 (d, J=8.79 Hz, 1 H) 7.45-7.50 (m, 1 H) 7.33-7.40 (m, 1H) 7.16-7.24 (m, 2 H) 6.64 (d, J=1.83 Hz, 1 H) 6.53 (dd, J=8.70, 2.11 Hz, 1 H) 5.19 (s, 2 H) 4.63 (s, 2 H) 4.13 (dd, J=5.40, 3.75 Hz, 2 H) 3.82 (dd, J=5.31, 3.85 Hz, 2 H)
ESI (+) MS m/z 302 (MH$^+$)
ESI (+) HRMS calcd for C$_{16}$H$_{16}$FN$_3$O$_2$+H$^+$: 302.1300; found 302.1302

6-[2-(4-Methoxy-benzyloxy)-ethoxy]-1H-indazol-3-ylamine $^1$H-NMR (400 MHz), δ (ppm, DMSO-d$_6$): 11.11 (s, 1 H) 7.51 (d, J=8.79 Hz, 1 H) 7.27 (d, J=8.61 Hz, 2 H) 6.91 (d, J=8.61 Hz, 2 H) 6.63 (d, J=1.65 Hz, 1 H) 6.53 (dd, J=8.79, 1.83 Hz, 1 H) 5.19 (s, 2 H) 4.48 (s, 2 H) 4.09-4.13 (m, 2H) 3.68-3.78 (m, 5 H)
ESI (+) MS m/z 314 (MH$^+$)
ESI (+) HRMS calcd for C$_{17}$H$_{19}$N$_3$O$_3$+H$^+$: 314.1499; found 314.1502

6-[2-(Pyridin-4-ylmethoxy)-ethoxy]-1H-indazol-3-ylamine $^1$H-NMR (400 MHz), δ (ppm, DMSO-d$_6$): 11.13 (s, 1 H) 8.51-8.55 (m, 2 H) 7.52 (d, J=8.79 Hz, 1 H) 7.35 (d, J=5.86 Hz, 2 H) 6.65 (d, J=1.83 Hz, 1 H) 6.55 (dd, J=8.61, 2.01 Hz, 1 H) 5.20 (s, 2 H) 4.63 (s, 2 H) 4.15-4.19 (m, 2 H) 3.81-3.88 (m, 2 H)
ESI (+) MS m/z 285 (MH$^+$)
ESI (+) HRMS calcd for C$_{15}$H$_{16}$N$_4$O$_2$+H$^+$: 285.1346; found 285.1339

6-((E)-3-Phenyl-allyloxy)-1H-indazol-3-ylamine $^1$H-NMR (400 MHz), δ (ppm, DMSO-d$_6$): 11.13 (s, 1 H) 7.54 (d, J=8.61 Hz, 1 H) 7.49 (d, J=7.14 Hz, 2 H) 7.35 (t, J=7.51 Hz, 2 H) 7.24-7.30 (m, 1 H) 6.77 (d, J=15.93 Hz, 1 H) 6.70 (s, 1 H) 6.57-6.60 (m, 1 H) 6.53 (dt, J=15.93, 5.68 Hz, 1 H) 5.20 (s, 2 H) 4.73 (d, J=5.31 Hz, 2 H)

ESI (+) MS m/z 266 (MH$^+$)

ESI (+) HRMS calcd for $C_{16}H_{15}N_3O+H^+$: 266.1288; found 266.1286

Example 2

N-[6-(2-Benzyloxy-ethoxy)-1H-indazol-3-yl]-4-(4-methyl-piperazin-1-yl)-benzamide (Cpd. 11)

Scheme 2, Step L)

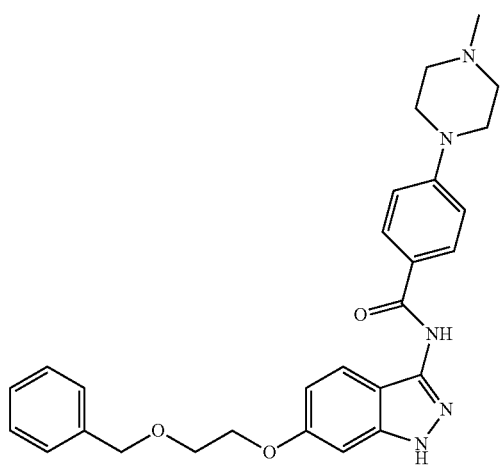 [SMILES: CN1CCN(c2ccc(C(=O)Nc3n[nH]c4cc(OCCOCc5ccccc5)ccc34)cc2)CC1]

A stirred suspension of 4-(4-methyl-piperazin-1-yl)-benzoyl chloride hydrochloride, prepared from 4.55 g (20.7 mmol) of 4-(4-methyl-piperazin-1-yl)-benzoic acid as described above in preparation 3, in dry pyridine (50 ml) was treated dropwise, at 0° C., under argon atmosphere, with a solution of 6-(2-benzyloxy-ethoxy)-1H-indazol-3-ylamine (5.31 g, 18.8 mmol) in 80 ml of dry pyridine. The reaction mixture was allowed to warm to r.t. under stirring overnight, then concentrated to 30 ml by rotary evaporation, poured into 500 ml of saturated solution of NaHCO$_3$ and extracted with 300+100 ml of DCM. The organic layers were combined, dried over sodium sulfate and evaporated to dryness. The crude residue was treated with 200 ml of EtOAc and stirred at reflux for 2 h. After cooling to r.t. the solid was filtered, washed with EtOAc and dried in oven at 50° C. under high vacuum to afford 5.23 g (yield: 57%) of the title compound as a white solid.

$^1$H-NMR (400 MHz), δ (ppm, DMSO-d$_6$): 12.44 (s, 1 H) 10.38 (s, 1 H) 7.95 (d, J=9.03 Hz, 2 H) 7.59 (d, J=8.91 Hz, 1H) 7.33-7.41 (m, 4 H) 7.25-7.32 (m, 1 H) 7.00 (d, J=9.15 Hz, 2 H) 6.85 (d, J=2.08 Hz, 1 H) 6.71 (dd, J=8.91, 2.20 Hz, 1 H) 4.58 (s, 2 H) 4.15-4.25 (m, 2 H) 3.70-3.88 (m, 2 H) 3.25-3.35 (m, 4 H) 2.42-2.48 (m, 4 H) 2.23 (s, 3 H)

ESI (+) MS m/z 486 (MH$^+$)

ESI (+) HRMS calcd for $C_{28}N_5O_3H_{31}+H^+$: 486.2500; found 486.2501

Operating in an analogous way, the following compounds were obtained:

N-[6-(2-Benzyloxy-ethoxy)-1H-indazol-3-yl]-4-dimethylaminomethyl-benzamide (Cpd. 21)

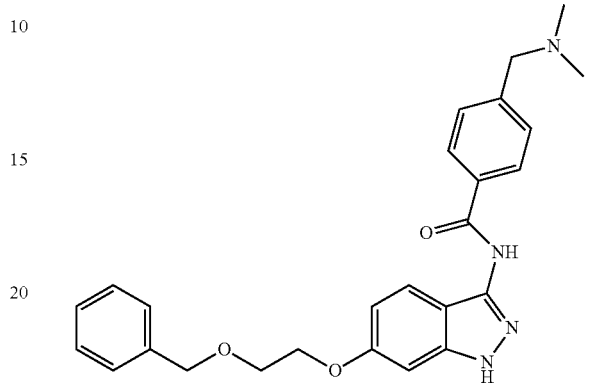

$^1$H-NMR (400 MHz), δ (ppm, DMSO-d$_6$): 12.51 (s, 1 H) 10.65 (s, 1 H) 8.02 (d, J=8.30 Hz, 2 H) 7.61 (d, J=8.91 Hz, 1H) 7.43 (d, J=8.42 Hz, 2 H) 7.33-7.38 (m, 4 H) 7.26-7.32 (m, 1 H) 6.87 (d, J=1.95 Hz, 1 H) 6.73 (dd, J=8.91, 2.08 Hz, 1 H) 4.59 (s, 2 H) 4.19-4.23 (m, 2 H) 3.79-3.84 (m, 2 H) 3.47 (s, 2 H) 2.17 (s, 6 H)

ESI (+) MS m/z 445 (MH$^+$)

ESI (+) HRMS calcd for $C_{26}N_4O_3H_{28}+H^+$: 445.2234; found 445.2224

N-[6-(2-Benzyloxy-ethoxy)-1H-indazol-3-yl]-4-(1-methyl-piperidin-4-yloxy)-benzamide (Cpd. 22)

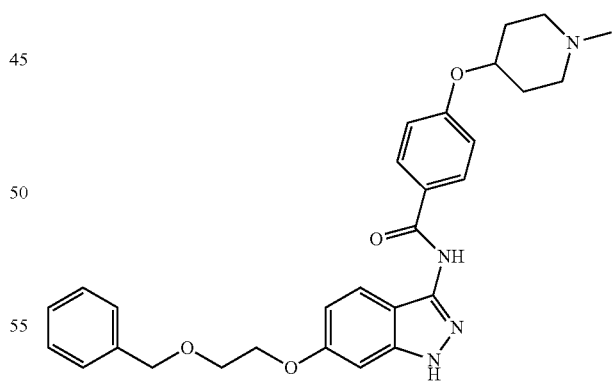

$^1$H-NMR (400 MHz), δ (ppm, DMSO-d$_6$): 12.48 (s, 1 H) 10.52 (s, 1 H) 7.99-8.04 (m, 2 H) 7.59 (d, J=8.91 Hz, 1 H) 7.33-7.40 (m, 4 H) 7.26-7.31 (m, 1 H) 7.04-7.09 (m, 2 H) 6.86 (d, J=1.95 Hz, 1 H) 6.72 (dd, J=8.91, 2.20 Hz, 1 H) 4.58 (s, 2 H) 4.44-4.54 (m, 1 H) 4.17-4.23 (m, 2 H) 3.79-3.86 (m, 2 H) 2.57-2.67 (m, 2 H) 2.14-2.25 (m, 5 H) 1.91-2.02 (m, 2 H) 1.59-1.75 (m, 2 H)

ESI (+) MS m/z 501 (MH$^+$)

ESI (+) HRMS calcd for $C_{29}N_4O_4H_{32}$+H$^+$: 501.2497; found 501.2482

N-[6-(2-Benzyloxy-ethoxy)-1H-indazol-3-yl]-3-(4-methyl-piperazin-1-yl)-benzamide hydrochloride (Cpd. 29)

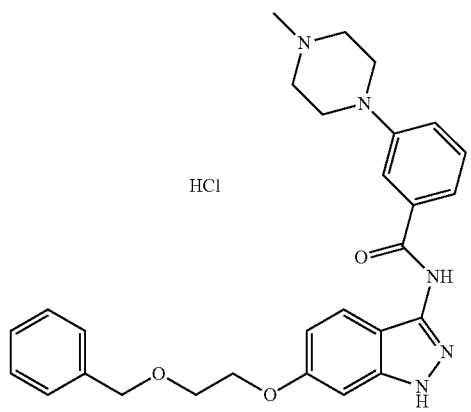 [SMILES: CN1CCN(c2cccc(C(=O)Nc3n[nH]c4cc(OCCOCc5ccccc5)ccc34)c2)CC1 ; Cl]

$^1$H-NMR (400 MHz), δ (ppm, DMSO-d$_6$): 12.56 (br. s., 1 H) 10.69 (s, 1 H) 10.17 (br. s., 1 H) 7.66 (br. s, 1 H) 7.61 (d, J=8.79 Hz, 1 H) 7.55 (d, J=7.69 Hz, 1 H) 7.41 (dd, J=8.43, 7.69 Hz, 1 H) 7.32-7.39 (m, 4 H) 7.27-7.31 (m, 1H) 7.24 (dd, J=8.43, 1.83 Hz, 1 H) 6.88 (d, J=1.83 Hz, 1 H) 6.73 (dd, J=8.79 Hz, 2.01 Hz, 1 H) 4.8 (s, 2 H) 4.16-4.24 (m, 2 H) 3.91-4.02 (m, 2 H) 3.78-3.84 (m, 2 H) 3.50-3.56 (m, 2 H) 3.01-3.23 (m, 4 H) 2.85 (d, J=4.21 Hz, 3 H)

ESI (+) MS m/z 486 (MH$^+$)
ESI (+) HRMS calcd for $C_{28}H_{31}N_5O_3$+H$^+$: 486.2500; found 486.2514

N-[6-(2-Benzyloxy-ethoxy)-1H-indazol-3-yl]-2-fluoro-4-(4-methyl-piperazin-1-yl)-benzamide (Cpd. 38)

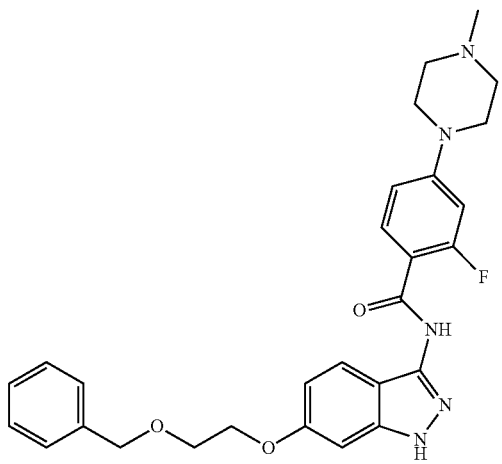 [SMILES: CN1CCN(c2ccc(C(=O)Nc3n[nH]c4cc(OCCOCc5ccccc5)ccc34)c(F)c2)CC1]

$^1$H-NMR (400 MHz), δ (ppm, DMSO-d$_6$): 12.45 (s, 1 H) 10.06 (d, J=3.66 Hz, 1 H) 7.61-7.69 (m, 2 H) 7.34-7.39 (m, 4 H) 7.27-7.31 (m, 1 H) 6.78-6.86 (m, 3 H) 6.72 (dd, J=8.88, 2.11 Hz, 1 H) 4.58 (s, 2 H) 4.18-4.21 (m, 2 H) 3.79-3.84 (m, 2 H) 3.29-3.33 (m, 4 H) 2.40-2.45 (m, 4 H) 2.22 (s, 3 H)

ESI (+) MS m/z 504 (MH$^+$)
ESI (+) HRMS calcd for $C_{28}H_{30}FN_5O_3$+H$^+$: 504.2406; found 504.2383

4-(4-Methyl-piperazin-1-yl)-N-{6-[2-(4-trifluoromethyl-benzyloxy)-ethoxy]-1H-indazol-3-yl}-benzamide (Cpd. 33)

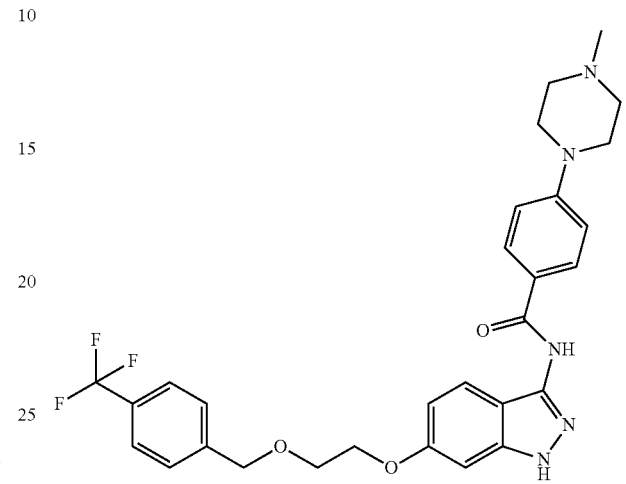

$^1$H-NMR (400 MHz), δ (ppm, DMSO-d$_6$): 12.45 (s, 1 H) 10.38 (s, 1 H) 7.95 (d, J=8.97 Hz, 2 H) 7.72 (d, J=8.06 Hz, 2H) 7.57-7.61 (m, 3 H) 7.00 (d, J=8.97 Hz, 2 H) 6.86 (d, J=1.83 Hz, 1 H) 6.72 (dd, J=8.88, 2.11 Hz, 1 H) 4.70 (s, 2 H) 4.20-4.25 (m, 2 H) 3.82-3.89 (m, 2 H) 3.27-3.35 (m, 4 H) 2.40-2.47 (m, 4 H) 2.23 (s, 3 H)

ESI (+) MS m/z 554 (MH$^+$)
ESI (+) HRMS calcd for $C_{29}H_{30}F_3N_5O_3$+H$^+$: 554.2374; found 554.2389

N-{6-[2-(4-Fluoro-benzyloxy)-ethoxy]-1H-indazol-3-yl}-4-(4-methyl-piperazin-1-yl)-benzamide (Cpd. 32)

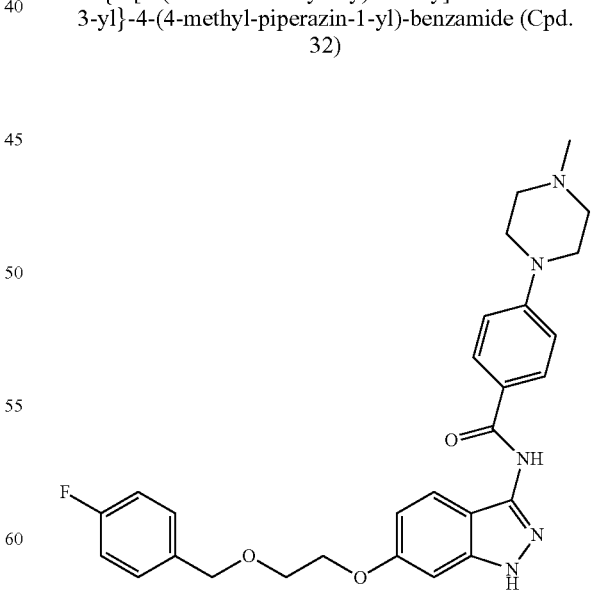

$^1$H-NMR (400 MHz), δ (ppm, DMSO-d$_6$): 12.44 (s, 1 H) 10.38 (s, 1 H) 7.95 (d, J=8.97 Hz, 2 H) 7.59 (d, J=8.79 Hz, 1H) 7.37-7.44 (m, 2 H) 7.15-7.21 (m, 2 H) 7.00 (d, J=8.97 Hz, 2 H) 6.85 (d, J=2.01 Hz, 1 H) 6.71 (dd, J=8.88, 2.11 Hz, 1 H) 4.56

(s, 2 H) 4.18-4.22 (m, 2 H) 3.79-3.82 (m, 2 H) 3.27-3.37 (m, 4 H) 2.43-2.47 (m, 4 H) 2.23 (s, 3 H)

ESI (+) MS m/z 504 (MH$^+$)

ESI (+) HRMS calcd for $C_{28}H_{30}FN_5O_3+H^+$: 504.2406; found 504.2414

4-(4-Methyl-piperazin-1-yl)-N-{6-[2-(3-trifluoromethyl-benzyloxy)-ethoxy]-1H-indazol-3-yl}-benzamide (Cpd. 34)

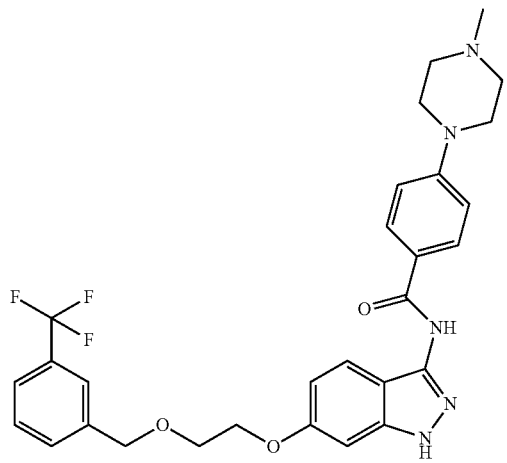 [SMILES: CN1CCN(c2ccc(C(=O)Nc3n[nH]c4cc(OCCOCc5cccc(C(F)(F)F)c5)ccc34)cc2)CC1]

$^1$H-NMR (400 MHz), δ (ppm, DMSO-d$_6$): 12.45 (s, 1 H) 10.38 (s, 1 H) 7.95 (d, J=9.03 Hz, 2 H) 7.72 (s, 1 H) 7.63-7.70 (m, 2 H) 7.56-7.63 (m, 2 H) 7.00 (d, J=9.15 Hz, 2 H) 6.86 (d, J=2.08 Hz, 1 H) 6.71 (dd, J=8.91, 2.07 Hz, 1 H) 4.70 (s, 2 H) 4.20-4.24 (m, 2 H) 3.83-3.89 (m, 2 H) 3.24-3.40 (m, 4 H) 2.42-2.48 (m, 4 H) 2.23 (s, 3 H)

ESI (+) MS m/z 554 (MH$^+$)

ESI (+) HRMS calcd for $C_{29}H_{30}F_3N_5O_3+H^+$: 554.2374; found 554.2371

N-{6-[2-(2-Fluoro-benzyloxy)-ethoxy]-1H-indazol-3-yl}-4-(4-methyl-piperazin-1-yl)-benzamide (Cpd. 30)

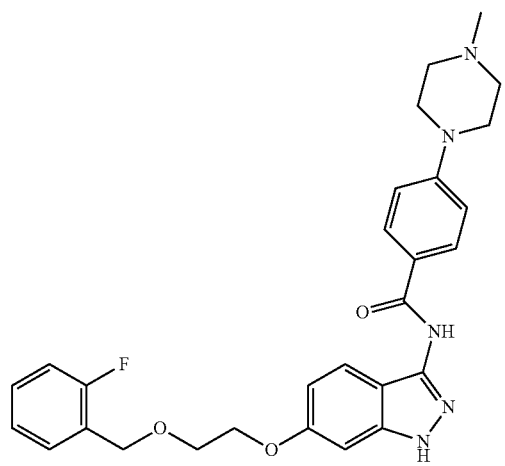 [SMILES: CN1CCN(c2ccc(C(=O)Nc3n[nH]c4cc(OCCOCc5ccccc5F)ccc34)cc2)CC1]

$^1$H-NMR (400 MHz), δ (ppm, DMSO-d$_6$): 12.44 (s, 1 H) 10.38 (s, 1 H) 7.95 (d, J=8.97 Hz, 2 H) 7.58 (d, J=8.79 Hz, 1H) 7.46-7.51 (m, 1 H) 7.35-7.40 (m, 1 H) 7.16-7.25 (m, 2 H) 7.00 (d, J=9.16 Hz, 2 H) 6.85 (d, J=1.83 Hz, 1 H) 6.70 (dd, J=8.88, 2.11 Hz, 1 H) 4.64 (s, 2 H) 4.18-4.21 (m, 2 H) 3.82-3.87 (m, 2 H) 3.22-3.31 (m, 4 H) 2.40-2.48 (m, 4 H) 2.23 (s, 3 H)

ESI (+) MS m/z 504 (MH$^+$)

ESI (+) HRMS calcd for $C_{28}H_{30}FN_5O_3+H^+$: 504.2406; found 504.2409

N-{6-[2-(4-Methoxy-benzyloxy)-ethoxy]-1H-indazol-3-yl}-4-(4-methyl-piperazin-1-yl)-benzamide (Cpd. 40)

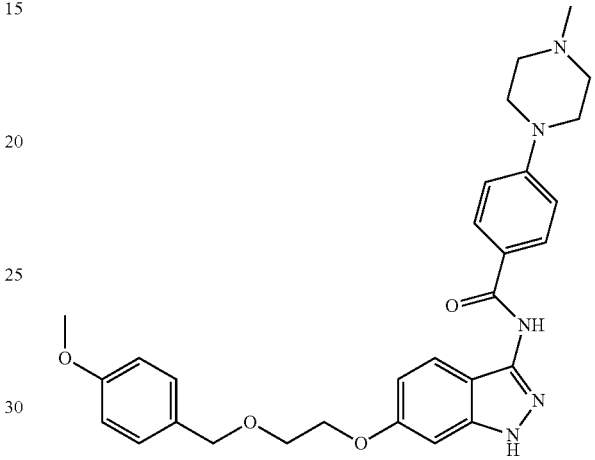

$^1$H-NMR (400 MHz), δ (ppm, DMSO-d$_6$): 12.44 (s, 1 H) 10.38 (s, 1 H) 7.95 (d, J=8.97 Hz, 2 H) 7.59 (d, J=8.97 Hz, 1H) 7.28 (d, J=8.61 Hz, 2 H) 7.00 (d, J=8.97 Hz, 2 H) 6.85-6.93 (m, 2 H) 6.84 (d, J=2.01 Hz, 1 H) 6.70 (dd, J=8.88, 2.11 Hz, 1 H) 4.50 (s, 2 H) 4.12-4.24 (m, 2 H) 3.76-3.80 (m, 2 H) 3.74 (s, 3 H) 3.27-3.34 (m, 4 H) 2.42-2.47 (m, 4 H) 2.23 (s, 3 H)

ESI (+) MS m/z 516 (MH$^+$)

ESI (+) HRMS calcd for $C_{29}H_{33}N_5O_4+H^+$: 516.2606; found 516.2617

N-[6-(2-Benzyloxy-ethoxy)-1H-indazol-3-yl]-2,4-bis-(4-methyl-piperazin-1-yl)-benzamide (Cpd. 43)

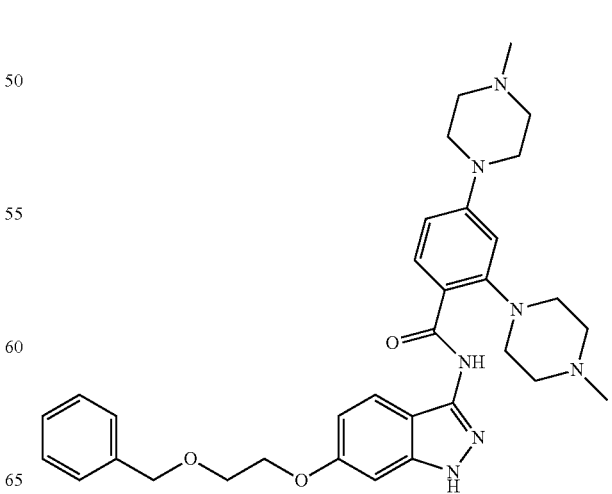

$^1$H-NMR (400 MHz), δ (ppm, DMSO-d$_6$): 12.65 (s, 1 H) 12.41 (s, 1 H) 8.01-8.05 (m, 1 H) 7.96-8.00 (m, 1 H) 7.34-7.39 (m, 4 H) 7.26-7.32 (m, 1 H) 6.84-6.89 (m, 2 H) 6.81-6.83 (m, 1 H) 6.68-6.73 (m, 1 H) 4.58 (s, 2 H) 4.17-4.21 (m, 2 H) 3.79-3.83 (m, 2 H) 3.27-3.32 (m, 4 H) 3.01-3.06 (m, 4 H) 2.56-2.71 (m, 4 H) 2.41-2.48 (m, 4 H) 2.25 (s, 3 H) 2.23 (s, 3 H)

ESI (+) MS m/z 584 (MH$^+$)

ESI (+) HRMS calcd for C$_{33}$H$_{41}$N$_7$O$_3$+H$^+$: 584.3344; found 584.3340

4-(4-Methyl-piperazin-1-yl)-N-{6-[2-(pyridin-4-ylmethoxy)-ethoxy]-1H-indazol-3-yl}-benzamide (Cpd. 35)

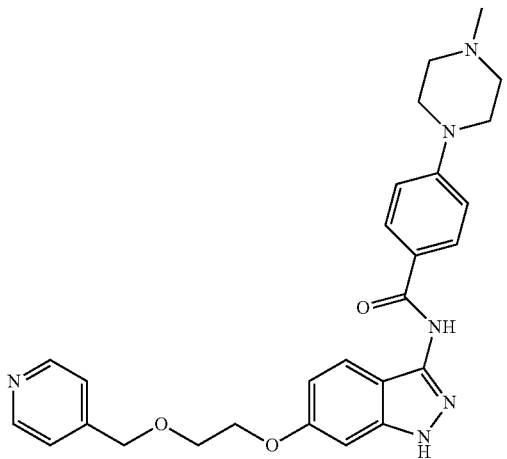 [SMILES: CN1CCN(c2ccc(C(=O)Nc3n[nH]c4cc(OCCOCc5ccncc5)ccc34)cc2)CC1]

$^1$H-NMR (400 MHz), δ (ppm, DMSO-d$_6$): 12.45 (s, 1 H) 10.38 (s, 1 H) 8.53 (d, J=4.58 Hz, 2 H) 7.95 (d, J=8.06 Hz, 2H) 7.60 (d, J=8.97 Hz, 1 H) 7.35 (d, J=4.58 Hz, 2 H) 7.00 (d, J=8.24 Hz, 2 H) 6.87 (s, 1 H) 6.72 (d, J=8.97 Hz, 1 H) 4.65 (s, 2 H) 4.21-4.25 (m, 2 H) 3.85-3.88 (m, 2 H) 3.27-3.37 (m, 4 H) 2.43-2.48 (m, 4 H) 2.23 (s, 3 H)

ESI (+) MS m/z 487 (MH$^+$)

ESI (+) HRMS calcd for C$_{27}$H$_{30}$N$_6$O$_3$+H$^+$: 487.2452; found 487.2450

4-(4-Methyl-piperazin-1-yl)-N-[6-((E)-3-phenyl-allyloxy)-1H-indazol-3-yl]-benzamide (Cpd. 39)

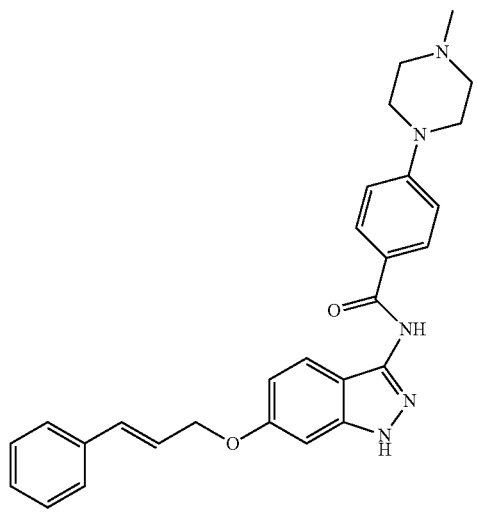 [SMILES: CN1CCN(c2ccc(C(=O)Nc3n[nH]c4cc(OC/C=C/c5ccccc5)ccc34)cc2)CC1]

$^1$H-NMR (400 MHz), δ (ppm, DMSO-d$_6$): 12.45 (s, 1 H) 10.39 (s, 1 H) 7.95 (d, J=8.97 Hz, 2 H) 7.61 (d, J=8.97 Hz, 1H) 7.48-7.52 (m, 2 H) 7.36 (t, J=7.69 Hz, 2 H) 7.26-7.31 (m, 1 H) 7.00 (d, J=8.97 Hz, 2 H) 6.91 (d, J=1.83 Hz, 1 H) 6.81 (d, J=16.12 Hz, 1 H) 6.75 (dd, J=8.97, 2.20 Hz, 1 H) 6.56 (dt, J=15.98, 5.75 Hz, 1 H) 4.80 (d, J=5.13 Hz, 2 H) 3.28-3.32 (m, 4 H) 2.43-2.47 (m, 4 H) 2.23 (s, 3 H)

ESI (+) MS m/z 468 (MH$^+$)

ESI (+) HRMS calcd for C$_{28}$H$_{29}$N$_5$O$_2$+H$^+$: 468.2394; found 468.2394

Preparation 12

N-[6-(2-Benzyloxy-ethoxy)-1H-indazol-3-yl]-4-bromo-benzamide

Scheme 2, Step M)

To a stirred solution of 6-(2-benzyloxy-ethoxy)-1H-indazol-3-ylamine (3.0 g, 10.6 mmol) in 30 ml of dry pyridine, at 0° C., under argon atmosphere, was added portionwise 4-bromo-benzoyl chloride (2.32 g, 10.6 mmol). The reaction mixture was allowed to warm to r.t. under stirring overnight then evaporated to dryness. The residue was treated with 50 ml of MeOH and 25 ml of 2N NaOH and stirred at r.t. for 1 h. The mixture was concentrated to ca. 10 ml by rotary evaporation, diluted with 200 ml of water, stirred for 15 min at r.t. and the suspended solid filtered and washed with water. After drying under vacuum, the crude solid was purified by chromatography (Biotage SP1 Flash Purification system) on a silica gel cartridge (Biotage SNAP 100 g) using DCM as eluant A and DCM/MeOH 9:1 as eluant B. Elution with a gradient from A/B 100:0 to 70:30 over 25 CV gave a pink solid that was triturated with EtOAc (50 ml), filtered, washed with EtOAc and dried affording 3.01 g (yield: 61%) of the title compound as a whitish solid.

$^1$H-NMR (400 MHz), δ (ppm, DMSO-d$_6$): 12.54 (s, 1 H) 10.81 (s, 1 H) 7.99 (d, J=8.54 Hz, 2 H) 7.75 (d, J=8.67 Hz, 2H) 7.62 (d, J=8.91 Hz, 1 H) 7.21-7.42 (m, 5 H) 6.87 (d, J=1.95 Hz, 1 H) 6.73 (dd, J=8.97, 2.14 Hz, 1 H) 4.58 (s, 2 H) 4.11-4.29 (m, 2 H) 3.71-3.98 (m, 2 H)

ESI (+) MS m/z 467 (MH$^+$)

Preparation 13

2-(4-trifluoromethyl-benzyloxy)-ethanol

Under argon atmosphere, at r.t., sodium hydride (60% dispersion in mineral oil, 1.92 g, 48 mmol) was stirred with n-hexane (ca. 10 ml). The hexane/mineral oil solution was drawn off and discarded and the left sodium hydride was treated with 20 ml of dry THF. Ethylene glycol (17.8 ml, 320 mmol) was then slowly dropped at r.t. (caution: hydrogen evolution) and the mixture stirred at r.t. for 1.5 hours. After heating up to reflux (80° C. oil bath) a solution of 1-bromomethyl-4-trifluoromethyl-benzene (7.6 g, 32 mmol) in 20 ml of dry THF was added and the reaction mixture stirred at reflux for 2.5 hours. After cooling to r.t., 100 ml of ammonium chloride saturated solution was added. The organic layer was separated, washed with 50 ml of water, dried over sodium sulfate and evaporated to dryness. The crude residue was purified by flash chromatography (Biotage SP1 Flash Purification system) on a silica gel cartridge (Varian SF40-120 g) using n-hexane as eluant A and EtOAc as eluant B. Elution with a gradient from A/B 75:25 to 70:30 over 2 CV then from 70:30 to 0:100 over 2 CV then 100% of B afforded 5.9 g (yield: 84%) of the title compound as a yellow oil (yield: 93%).

¹H-NMR (400 MHz), δ (ppm, DMSO-d₆): 7.71 (d, J=8.06 Hz, 2 H) 7.56 (d, J=7.88 Hz, 2 H) 4.66 (t, J=5.49 Hz, 1 H) 4.60 (s, 2 H) 3.56 (q, J=5.31 Hz, 2 H) 3.48-3.51 (m, 2 H)

ESI (+) MS m/z 221 (MH⁺)

ESI (+) HRMS calcd for $C_{10}H_{11}F_3O_2$+Na⁺: 243.0603; found 243.0594

Operating in an analogous way, the following compounds were obtained:

2-(4-Fluoro-benzyloxy)-ethanol

¹H-NMR (400 MHz), δ (ppm, DMSO-d₆): 7.37 (dd, J=8.43, 5.86 Hz, 2 H) 7.16 (t, J=8.88 Hz, 2 H) 4.62 (t, J=5.49 Hz, 1H) 4.46 (s, 2 H) 3.53 (q, J=5.19 Hz, 2 H) 3.41-3.47 (m, 2 H)

ESI (+) MS m/z 171 (MH⁺)

ESI (+) HRMS calcd for $C_9H_{11}FO_2$+Na⁺: 193.0635; found 193.0635

2-(3-Trifluoromethyl-benzyloxy)-ethanol

¹H-NMR (400 MHz), δ (ppm, DMSO-d₆): 7.55-7.72 (m, 4 H) 4.66 (t, J=5.49 Hz, 1 H) 4.59 (s, 2 H) 3.53-3.59 (m, 2H) 3.47-3.52 (m, 2 H)

ESI (+) MS m/z 221 (MH⁺)

2-(2-Fluoro-benzyloxy)-ethanol

¹H-NMR (400 MHz), δ (ppm, DMSO-d₆): 7.47 (td, J=7.51, 1.65 Hz, 1 H) 7.36 (tdd, J=7.76, 7.76, 5.63, 1.74 Hz, 1 H) 7.14-7.21 (m, 2 H) 4.63 (t, J=5.49 Hz, 1 H) 4.54 (s, 2 H) 3.51-3.55 (m, 2 H) 3.46-3.50 (m, 2 H)

ESI (+) MS m/z 171 (MH⁺)

ESI (+) HRMS calcd for $C_9H_{11}FO_2$+Na⁺: 193.0635; found 193.0635

2-(4-Methoxy-benzyloxy)-ethanol

¹H-NMR (400 MHz), δ (ppm, DMSO-d₆): 7.25 (d, J=8.79 Hz, 2 H) 6.90 (d, J=8.61 Hz, 2 H) 4.58 (t, J=5.59 Hz, 1 H) 4.40 (s, 2 H) 3.74 (s, 3 H) 3.51 (q, J=5.31 Hz, 2 H) 3.39-3.43 (m, 2 H)

ESI (+) MS m/z 183 (MH⁺)

ESI (+) HRMS calcd for $C_{10}H_{14}O_3$+Na⁺: 205.0835; found 205.0835

2-(Pyridin-4-ylmethoxy)-ethanol

¹H-NMR (400 MHz), δ (ppm, DMSO-d₆): 8.51-8.54 (m, 2 H) 7.32-7.36 (m, 2 H) 4.68 (t, J=5.49 Hz, 1 H) 4.55 (s, 2H) 3.57 (q, J=5.25 Hz, 2 H) 3.46-3.52 (m, 2 H)

ESI (+) MS m/z 154 (MH⁺)

ESI (+) HRMS calcd for $C_8H_{11}NO_2$+H⁺: 154.0863; found 154.0857

Preparation 14

Methanesulfonic acid 2-(4-trifluoromethyl-benzyloxy)-ethyl ester

To a solution of 2-(4-trifluoromethyl-benzyloxy)-ethanol (1.0 g, 4.5 mmol) in dry DCM (20 ml) and DIPEA (2.36 ml, 13.5 mmol), at 0° C., under argon atmosphere, was added methanesulfonyl chloride (421 µl, 5.4 mmol). The reaction mixture was stirred at 0° C. for 10 minutes, then the ice-bath removed and the stirring continued for 2 hours at r.t. The mixture was then diluted with 70 ml of DCM and washed with 50 ml of NaHCO₃ saturated solution, 100 ml of water, 100 ml of 2N HCl and 100 ml of water, dried over sodium sulfate and evaporated to dryness affording 1.35 g (yield: quantitative) of methanesulfonic acid 2-(4-trifluoromethyl-benzyloxy)-ethyl ester as a brown oil that was used as such for the next step without further purification.

¹H-NMR (400 MHz), δ (ppm, DMSO-d₆): 7.73 (d, J=8.06 Hz, 2 H) 7.57 (d, J=7.88 Hz, 2 H) 4.64 (s, 2 H) 4.35-4.42 (m, 2 H) 3.71-3.78 (m, 2 H) 3.18 (s, 3 H)

ESI (+) MS m/z 299 (MH⁺)

ESI (+) HRMS calcd for $C_{11}H_{13}F_3O_4S$+Na⁺: 321.0379; found 321.0380

Operating in an analogous way, the following compounds were obtained:

Methanesulfonic acid 2-(4-fluoro-benzyloxy)-ethyl ester

¹H-NMR (400 MHz), δ (ppm, DMSO-d₆): 7.30-7.44 (m, 2 H) 7.12-7.23 (m, 2 H) 4.51 (s, 2 H) 4.29-4.38 (m, 2 H) 3.63-3.75 (m, 2 H) 3.17 (s, 3 H)

ESI (+) MS m/z 249 (MH⁺)

ESI (+) HRMS calcd for $C_{11}H_{13}F_3O_4S$+Na⁺: 271.0411; found 271.0412

Methanesulfonic acid 2-(3-trifluoromethyl-benzyloxy)-ethyl ester

¹H-NMR (400 MHz), δ (ppm, DMSO-d₆): 7.55-7.72 (m, 4 H) 4.64 (s, 2 H) 4.34-4.42 (m, 2 H) 3.71-3.78 (m, 2 H) 3.18 (s, 3 H)

ESI (+) MS m/z 299 (MH⁺)

Methanesulfonic acid 2-(2-fluoro-benzyloxy)-ethyl ester

¹H-NMR (400 MHz), δ (ppm, DMSO-d₁₆): 7.44-7.48 (m, 1 H) 7.34-7.41 (m, 1 H) 7.16-7.25 (m, 2 H) 4.59 (s, 2 H) 4.34-4.36 (m, 2 H) 3.71-3.75 (m, 2 H) 3.16 (s, 3 H)

ESI (+) MS m/z 249 (MH⁺)

ESI (+) HRMS calcd for $C_{11}H_{13}F_3O_4S$+Na⁺: 271.0411; found 271.0411

Methanesulfonic acid 2-(4-methoxy-benzyloxy)-ethyl ester

¹H-NMR (400 MHz), δ (ppm, DMSO-d₆): 7.26 (d, J=8.79 Hz, 2 H) 6.76-7.00 (m, 2 H) 4.45 (s, 2 H) 4.28-4.35 (m, 2H) 3.74 (s, 3 H) 3.60-3.68 (m, 2 H) 3.16 (s, 3 H)

ESI (+) MS m/z 261 (MH⁺)

ESI (+) HRMS calcd for $C_{11}H_{16}O_5S$+Na⁺: 283.0610; found 283.0614

Methanesulfonic acid 2-(pyridin-4-ylmethoxy)-ethyl ester

¹H-NMR (400 MHz), δ (ppm, DMSO-d₆): 8.51-8.57 (m, 2 H) 7.34 (d, J=5.86 Hz, 2 H) 4.60 (s, 2 H) 4.36-4.41 (m, 2H) 3.72-3.78 (m, 2 H) 3.19 (s, 3 H)

ESI (+) MS m/z 232 (MH⁺)

ESI (+) HRMS calcd for $C_9H_{13}NO_4S$+H⁺: 232.0638; found 232.0636

Example 3

N-[6-(2-Benzyloxy-ethoxy)-1H-indazol-3-yl]-4-(4-dimethylamino-piperidin-1-yl)-benzamide (Cpd. 15)

Scheme 2, Step N)

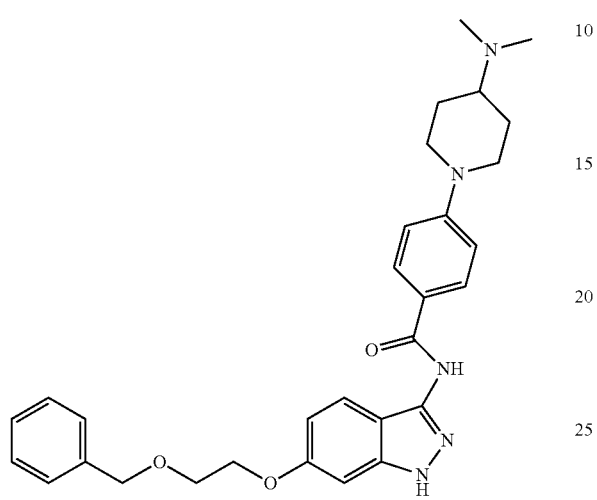

A solution of N-[6-(2-benzyloxy-ethoxy)-1H-indazol-3-yl]-4-bromo-benzamide (1.3 g, 2.79 mmol) and 4-dimethylamino-piperidine (1.18 ml, 8.37 mmol) in dry THF (20 ml) was degassed by three vacuum-argon atmosphere cycles and treated at r.t., under argon atmosphere, with $Pd_2(dba)_3$ (50 mg), 2-dicyclohexylphosphino-2'-(N,N-dimethylamino)biphenyl (50 mg) and 1M LiHMDS in THF (22.3 ml, 22.3 mmol). The reaction mixture was heated to reflux and stirred for 15 min then cooled to r.t., poured into 200 ml of water and extracted with 200 ml of EtOAc. The organic layer was separated, dried over sodium sulfate and evaporated to dryness. The crude residue was purified by chromatography (Biotage SP1 Flash Purification system) on a silica gel cartridge (Varian SF40-120 g) using DCM as eluant A and DCM/7N $NH_3$ in MeOH 10:1 as eluant B. Elution with a gradient from A/B 100:0 to 0:100 over 10 CV, followed by an isocratic elution with eluant B (5 CV), gave a yellow solid that was triturated with EtOAc (15 ml), filtered, washed with EtOAc and dried affording 1.04 g (yield: 73%) of the title compound as a white solid.

$^1$H-NMR (400 MHz), δ (ppm, DMSO-$d_6$): 12.44 (s, 1 H) 10.35 (s, 1 H) 7.85-8.01 (m, 2 H) 7.59 (d, J=8.91 Hz, 1 H) 7.33-7.40 (m, 4 H) 7.25-7.32 (m, 1 H) 6.93-7.06 (m, 2 H) 6.85 (d, J=2.07 Hz, 1 H) 6.71 (dd, J=8.91, 2.08 Hz, 1 H) 4.58 (s, 2 H) 4.14-4.26 (m, 2 H) 3.86-3.98 (m, 2 H) 3.73-3.85 (m, 2 H) 2.74-2.90 (m, 2 H) 2.23-2.35 (m, 1 H) 2.19 (s, 6 H) 1.77-1.87 (m, 2 H) 1.35-1.50 (m, 2 H)

ESI (+) MS m/z 514 (MH$^+$)

ESI (+) HRMS calcd for $C_{30}N_5O_3H_{35}+H^+$: 514.2813; found 514.2817

Operating in an analogous way, the following compounds were obtained:

N-[6-(2-Benzyloxy-ethoxy)-1H-indazol-3-yl]-4-[(2-dimethylamino-ethyl)-methyl-amino]-benzamide (Cpd. 16)

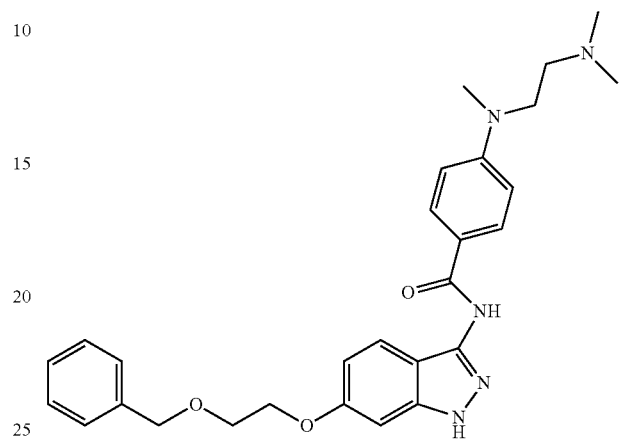

$^1$H-NMR (400 MHz), δ (ppm, DMSO-$d_6$): 12.41 (s, 1 H) 10.27 (s, 1 H) 7.89-7.96 (m, 2 H) 7.59 (d, J=8.91 Hz, 1 H) 7.33-7.38 (m, 4 H) 7.25-7.32 (m, 1 H) 6.85 (d, J=2.07 Hz, 1 H) 6.68-6.76 (m, 3 H) 4.58 (s, 2 H) 4.17-4.22 (m, 2H) 3.78-3.85 (m, 2 H) 3.50 (t, J=7.08 Hz, 2 H) 2.99 (s, 3 H) 2.40 (t, J=7.02 Hz, 2 H) 2.19 (s, 6 H)

ESI (+) MS m/z 488 (MH$^+$)

ESI (+) HRMS calcd for $C_{28}N_5O_3H_{33}+H^+$: 488.2656; found 488.2654

N-[6-(2-Benzyloxy-ethoxy)-1H-indazol-3-yl]-4-[(3-dimethylamino-propyl)-methyl-amino]-benzamide (Cpd. 17)

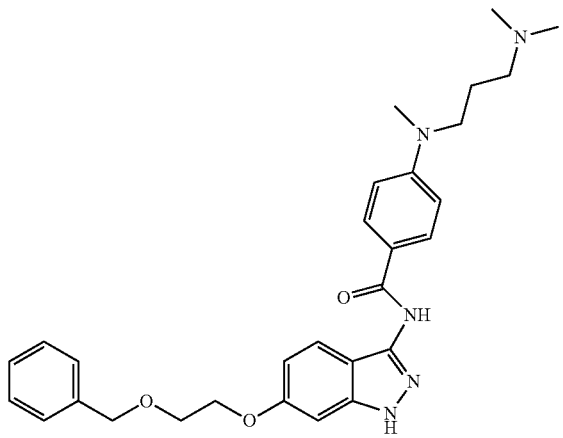 [SMILES: CN(C)CCCN(C)c1ccc(C(=O)Nc2n[nH]c3cc(OCCOCc4ccccc4)ccc23)cc1]

$^1$H-NMR (400 MHz), δ (ppm, DMSO-$d_6$): 12.41 (s, 1 H) 10.26 (s, 1 H) 7.90-7.95 (m, 2 H) 7.59 (d, J=8.91 Hz, 1 H) 7.34-7.40 (m, 4 H) 7.27-7.32 (m, 1 H) 6.85 (d, J=2.07 Hz, 1 H) 6.72-6.77 (m, 2 H) 6.70 (dd, J=8.91, 2.20 Hz, 1 H) 4.58 (s, 2 H) 4.17-4.23 (m, 2 H) 3.79-3.83 (m, 2 H) 3.43 (t, J=7.14 Hz, 2 H) 2.98 (s, 3 H) 2.23 (t, J=6.84 Hz, 2 H) 2.14 (s, 6 H) 1.61-1.71 (m, 2 H)

ESI (+) MS m/z 502 (MH$^+$)

ESI (+) HRMS calcd for $C_{29}N_5O_3H_{35}$+H$^+$: 502.2813; found 502.2794

4-{4-[6-(2-Benzyloxy-ethoxy)-1H-indazol-3-ylcarbamoyl]-phenyl}-piperazine-1-carboxylic acid tert-butyl ester (Cpd. 18)

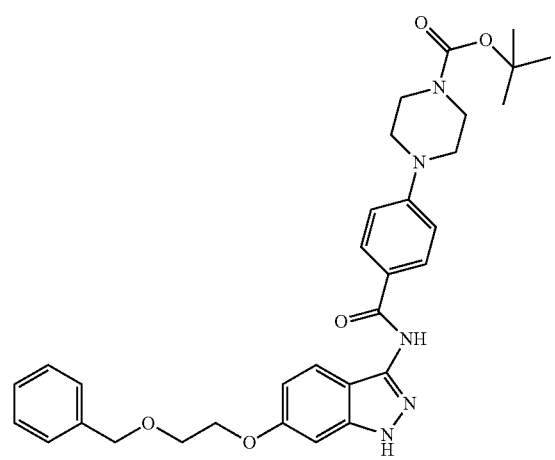 [SMILES: CC(C)(C)OC(=O)N1CCN(c2ccc(C(=O)Nc3n[nH]c4cc(OCCOCc5ccccc5)ccc34)cc2)CC1]

$^1$H-NMR (400 MHz), δ (ppm, DMSO-d$_6$): 12.45 (s, 1 H) 10.40 (s, 1 H) 7.95-7.99 (m, 2 H) 7.59 (d, J=9.03 Hz, 1 H) 7.34-7.38 (m, 4 H) 7.26-7.33 (m, 1 H) 6.98-7.05 (d, J=9.15 Hz, 2 H) 6.85 (d, J=2.20 Hz, 1 H) 6.71 (dd, J=8.91, 2.07 Hz, 1 H) 4.58 (s, 2 H) 4.16-4.23 (m, 2 H) 3.79-3.86 (m, 2 H) 3.44-3.51 (m, 4 H) 3.27-3.32 (m, 4 H) 1.43 (s, 9 H)

ESI (+) MS m/z 572 (MH$^+$)

ESI (+) HRMS calcd for $C_{32}N_5O_5H_{37}$+H$^+$: 572.2868; found 572.2862

N-[6-(2-Benzyloxy-ethoxy)-1H-indazol-3-yl]-4-(1-methyl-piperidin-4-ylamino)-benzamide (Cpd. 19)

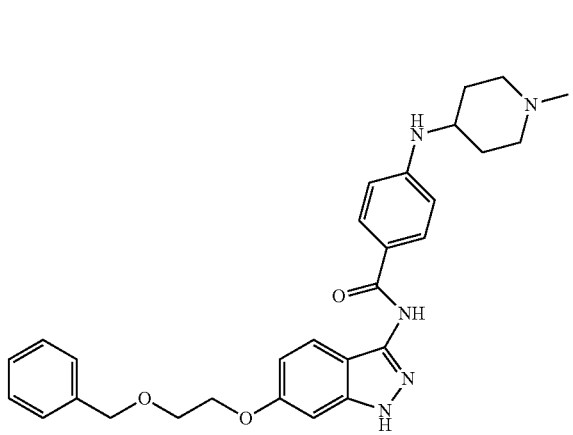 [SMILES: CN1CCC(Nc2ccc(C(=O)Nc3n[nH]c4cc(OCCOCc5ccccc5)ccc34)cc2)CC1]

$^1$H-NMR (400 MHz), δ (ppm, DMSO-d$_6$): 12.40 (s, 1 H) 10.18 (s, 1 H) 7.83 (d, J=8.91 Hz, 2 H) 7.58 (d, J=8.91 Hz, 1H) 7.34-7.39 (m, 4 H) 7.25-7.30 (m, 1 H) 6.84 (d, J=2.07 Hz, 1 H) 6.69 (dd, J=8.91, 2.20 Hz, 1 H) 6.62 (d, J=8.91 Hz, 2 H) 6.15 (d, J=7.81 Hz, 1 H) 4.58 (s, 2 H) 4.17-4.23 (m, 2 H) 3.78-3.84 (m, 2 H) 2.70-2.78 (m, 2 H) 2.17 (s, 3H) 1.96-2.09 (m, 2 H) 1.83-1.94 (m, 2 H) 1.33-1.51 (m, 2 H)

ESI (+) MS m/z 500 (MH$^+$)

ESI (+) HRMS calcd for $C_{29}N_5O_3H_{33}$+H$^+$: 500.2656; found 500.2648

N-[6-(2-Benzyloxy-ethoxy)-1H-indazol-3-yl]-4-[methyl-(1-methyl-piperidin-4-yl)-amino]-benzamide (Cpd. 23)

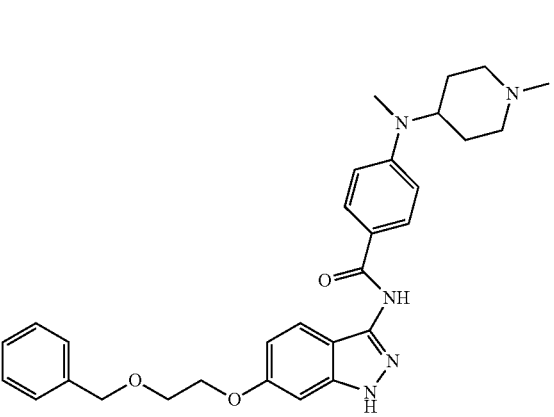 [SMILES: CN1CCC(N(C)c2ccc(C(=O)Nc3n[nH]c4cc(OCCOCc5ccccc5)ccc34)cc2)CC1]

$^1$H-NMR (400 MHz), δ (ppm, DMSO-d$_6$): 12.42 (s, 1 H) 10.28 (s, 1 H) 7.93 (d, J=8.91 Hz, 2 H) 7.59 (d, J=8.91 Hz, 1H) 7.33-7.39 (m, 4 H) 7.25-7.34 (m, 1 H) 6.80-6.87 (m, 3 H) 6.70 (dd, J=8.91, 2.07 Hz, 1 H) 4.58 (s, 2 H) 4.17-4.23 (m, 2 H) 3.79-3.85 (m, 2 H) 3.66-3.79 (m, 1 H) 2.82-2.88 (m, 2 H) 2.82 (s, 3 H) 2.19 (s, 3 H) 2.00-2.11 (m, 2 H) 1.71-1.85 (m, 2 H) 1.55-1.64 (m, 2 H)

ESI (+) MS m/z 514 (MH$^+$)

ESI (+) HRMS calcd for $C_{30}N_5O_3H_{35}$+H$^+$: 514.2813; found 514.2792

N-[6-(2-Benzyloxy-ethoxy)-1H-indazol-3-yl]-4-morpholin-4-yl-benzamide (Cpd. 24)

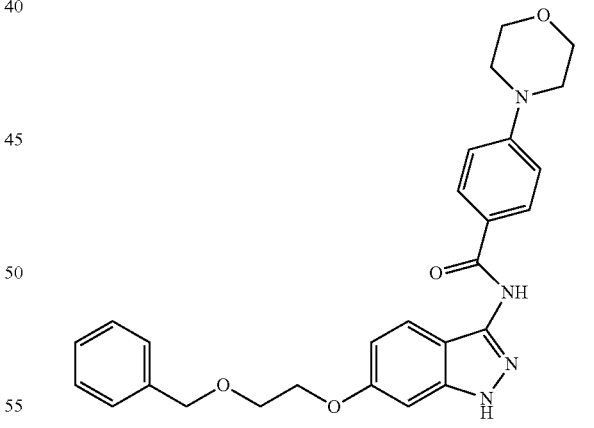

$^1$H-NMR (400 MHz), δ (ppm, DMSO-d$_6$): 12.45 (s, 1 H) 10.40 (s, 1 H) 7.97 (d, J=9.03 Hz, 2 H) 7.59 (d, J=8.91 Hz, 1H) 7.34-7.39 (m, 4 H) 7.25-7.33 (m, 1 H) 7.02 (d, J=9.03 Hz, 2 H) 6.85 (d, J=1.83 Hz, 1 H) 6.71 (dd, J=8.91, 2.20 Hz, 1 H) 4.58 (s, 2 H) 4.16-4.23 (m, 2 H) 3.78-3.84 (m, 2 H) 3.71-3.77 (m, 4 H) 3.24-3.28 (m, 4 H)

ESI (+) MS m/z 473 (MH$^+$)

ESI (+) HRMS calcd for $C_{27}N_4O_4H_{28}$+H$^+$: 473.2184; found 473.2169

N-[6-(2-Benzyloxy-ethoxy)-1H-indazol-3-yl]-4-(2-morpholin-4-yl-ethylamino)-benzamide hydrochloride (Cpd. 25)

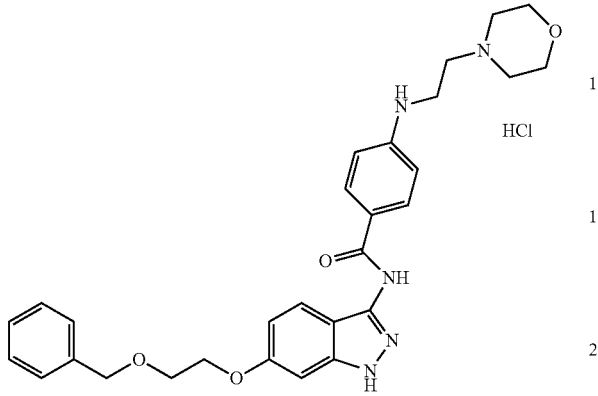

$^1$H-NMR (400 MHz), δ (ppm, DMSO-d$_6$): 12.44 (bs, 1 H) 10.66 (bs, 1 H) 10.30 (s, 1 H) 7.91 (d, J=8.79 Hz, 2 H) 7.59 (d, J=8.91 Hz, 1 H) 7.33-7.39 (m, 4 H) 7.25-7.32 (m, 1 H) 6.85 (d, J=1.83 Hz, 1 H) 6.67-6.75 (m, 3 H) 4.58 (s, 2H) 4.16-4.23 (m, 2 H) 3.90-4.04 (m, 2 H) 3.70-3.87 (m, 4 H) 3.54-3.62 (m, 2 H) 3.44-3.54 (m, 2 H) 3.24-3.33 (m, 2 H) 3.03-3.23 (m, 2 H)

ESI (+) MS m/z 516 (MH$^+$)

ESI (+) HRMS calcd for C$_{29}$N$_5$O$_4$H$_{33}$+H$^+$: 516.2606; found 516.2584

N-[6-(2-Benzyloxy-ethoxy)-1H-indazol-3-yl]-4-(tetrahydro-pyran-4-ylamino)-benzamide (Cpd. 26)

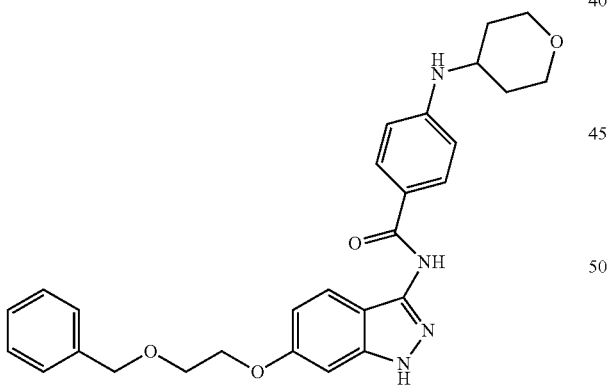

$^1$H-NMR (400 MHz), δ (ppm, DMSO-d$_6$): 12.40 (s, 1 H) 10.20 (s, 1 H) 7.84 (d, J=8.67 Hz, 2 H) 7.58 (d, J=8.91 Hz, 1H) 7.34-7.38 (m, 4 H) 7.26-7.31 (m, 1 H) 6.84 (d, J=1.71 Hz, 1 H) 6.70 (dd, J=8.91, 1.83 Hz, 1 H) 6.65 (d, J=8.67 Hz, 2 H) 6.22 (d, J=7.81 Hz, 1 H) 4.58 (s, 2 H) 4.16-4.22 (m, 2 H) 3.84-3.92 (m, 2 H) 3.79-3.84 (m, 2 H) 3.50-3.63 (m, 1 H) 3.40-3.48 (m, 2 H) 1.85-1.94 (m, 2 H) 1.32-1.47 (m, 2 H)

ESI (+) MS m/z 487 (MH$^+$)

ESI (+) HRMS calcd for C$_{28}$N$_4$O$_4$H$_{30}$+H$^+$: 487.2340; found 487.2340

N-[6-(2-Benzyloxy-ethoxy)-1H-indazol-3-yl]-4-[(1-methyl-piperidin-4-ylmethyl)-amino]-benzamide (Cpd. 27)

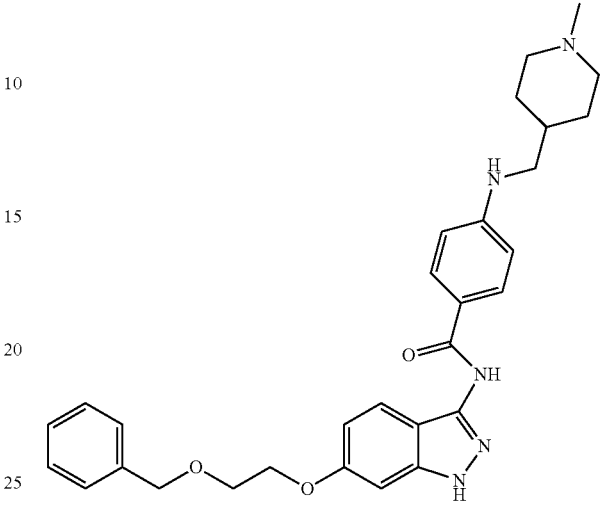

$^1$H-NMR (400 MHz), δ (ppm, DMSO-d$_6$): 12.39 (s, 1 H) 10.18 (s, 1 H) 7.83 (d, J=8.67 Hz, 2 H) 7.58 (d, J=8.91 Hz, 1H) 7.33-7.40 (m, 4 H) 7.25-7.30 (m, 1 H) 6.84 (d, J=1.83 Hz, 1 H) 6.70 (dd, J=8.91, 2.07 Hz, 1 H) 6.61 (d, J=8.79 Hz, 2 H) 6.33 (t, J=5.68 Hz, 1 H) 4.58 (s, 2 H) 4.17-4.23 (m, 2 H) 3.78-3.85 (m, 2 H) 2.97 (t, J=6.16 Hz, 2 H) 2.72-2.80 (m, 2 H) 2.14 (s, 3 H) 1.76-1.86 (m, 2 H) 1.67-1.76 (m, 2 H) 1.42-1.59 (m, 1 H) 1.14-1.30 (m, 2 H)

ESI (+) MS m/z 514 (MH$^+$)

ESI (+) HRMS calcd for C$_{30}$N$_5$O$_3$H$_{35}$+H$^+$: 514.2813; found 514.2797

N-[6-(2-Benzyloxy-ethoxy)-1H-indazol-3-yl]-4-(3-pyrrolidin-1-yl-azetidin-1-yl)-benzamide (Cpd. 28)

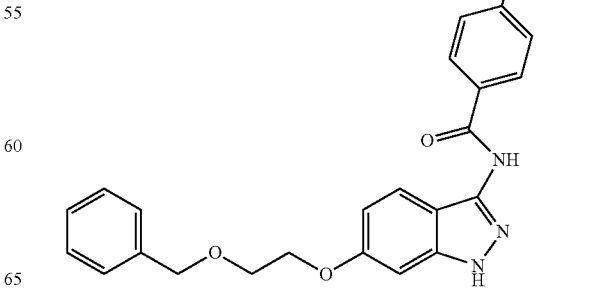

¹H-NMR (400 MHz), δ (ppm, DMSO-d₆): 12.42 (s, 1 H) 10.30 (s, 1 H) 7.93 (d, J=8.67 Hz, 2 H) 7.59 (d, J=8.91 Hz, 1H) 7.32-7.40 (m, 4 H) 7.26-7.30 (m, 1 H) 6.85 (d, J=1.95 Hz, 1 H) 6.70 (dd, J=8.91, 2.07 Hz, 1 H) 6.45 (d, J=8.79 Hz, 2 H) 4.58 (s, 2 H) 4.10-4.27 (m, 2 H) 4.00 (t, J=7.38 Hz, 2 H) 3.80-3.87 (m, 2 H) 3.75 (dd, J=7.87, 4.94 Hz, 2H) 3.41-3.49 (m, 1 H) 2.45-2.49 (m, 4 H) 1.66-1.82 (m, 4 H)

ESI (+) MS m/z 512 (MH⁺)

ESI (+) HRMS calcd for $C_{30}N_5O_3H_{33}+H^+$: 512.2656; found 512.2650

Example 4

N-[6-(2-Benzyloxy-ethoxy)-1H-indazol-3-yl]-4-(4-methyl-4-oxy-piperazin-1-yl)-benzamide (Cpd. 14)

Conversion 7

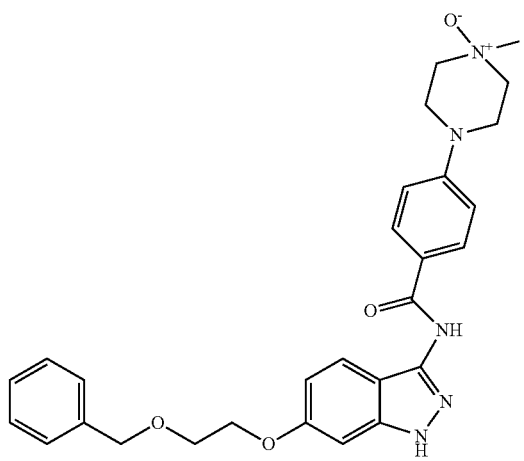 [SMILES: C[N+]1([O-])CCN(c2ccc(C(=O)Nc3n[nH]c4cc(OCCOCc5ccccc5)ccc34)cc2)CC1]

A solution of N-[6-(2-benzyloxy-ethoxy)-1H-indazol-3-yl]-4-(4-methyl-piperazin-1-yl)-benzamide (300 mg, 0.62 mmol) in DCM (5 ml) and MeOH (5 ml) was treated at r.t. with 3-chloroperbenzoic acid (107 mg, 0.62 mmol). After stirring for 2 h at r.t. the precipitated solid was filtered, washed with few ml of DCM/MeOH 1:1 and with MeOH and dried in vacuo affording 125 mg of the title compound (yield: 40%) as a white solid.

¹H-NMR (400 MHz), δ (ppm, DMSO-d6): 12.47 (s, 1H) 10.43 (s, 1 H) 7.95-8.02 (m, 2 H) 7.60 (d, J=9.08 Hz, 1 H) 7.25-7.40 (m, 5 H) 7.03-7.12 (m, 2 H) 6.86 (d, J=2.05 Hz, 1 H) 6.71 (dd, J=9.08, 2.05 Hz, 1 H) 4.59 (s, 2 H) 4.16-4.24 (m, 2 H) 3.79-3.86 (m, 2 H) 3.67-3.77 (m, 2 H) 3.43-3.63 (m, 4H) 3.12 (s, 3 H) 3.96-3.07 (m, 2 H)

ESI (+) MS m/z 502 (MH⁺)

ESI (+) HRMS calcd for $C_{28}N_5O_4H_{31}+H^+$: 502.2449; found 502.2443

The title compound (120 mg) was then suspended in 10 ml of ethanol, treated with 2N HCl (0.5 ml) and stirred until a clear solution was obtained. Evaporation of the solvent, trituration with diethyl ether and drying in vacuo afforded 127 mg of the hydrochloride salt of the title compound as a white solid.

¹H-NMR (400 MHz), δ (ppm, DMSO-d₆): 12.55 (s, 1 H) 12.51 (bs, 1 H) 10.48 (s, 1 H) 8.02 (d, J=8.79 Hz, 2 H) 7.59 (d, J=8.91 Hz, 1 H) 7.33-7.41 (m, 4 H) 7.25-7.32 (m, 1 H) 7.13 (d, J=8.91 Hz, 2 H) 6.86 (d, J=1.59 Hz, 1 H) 6.72 (dd, J=8.85, 1.89 Hz, 1 H) 4.58 (s, 2 H) 4.14-4.26 (m, 2 H) 3.94-4.03 (m, 2 H) 3.74-3.89 (m, 6 H) 3.59 (s, 3 H) 3.40-3.50 (m, 2 H)

ESI (+) MS m/z 502 (MH⁺)

ESI (+) HRMS calcd for $C_{28}N_5O_4H_{31}+H^+$: 502.2449; found 502.2438

Operating in an analogous way, the following compounds were obtained:

N-[6-(2-Benzyloxy-ethoxy)-1H-indazol-3-yl]-4-[methyl-(1-methyl-1-oxy-piperidin-4-yl)-amino]-benzamide (Cpd. 41)

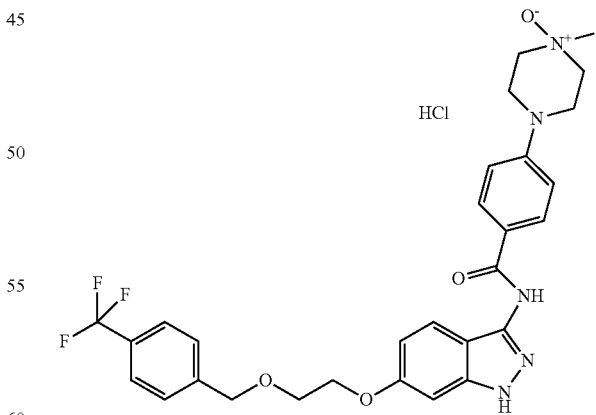

¹H-NMR (400 MHz), δ (ppm, DMSO-d₆): 12.49 (s, 1 H) 10.32 (s, 1 H) 7.95 (d, J=9.03 Hz, 2 H) 7.59 (d, J=8.91 Hz, 1H) 7.33-7.41 (m, 4 H) 7.24-7.33 (m, 1 H) 6.87 (d, J=9.15 Hz, 2 H) 6.85 (d, J=2.20 Hz, 1 H) 6.70 (dd, J=8.97, 2.14 Hz, 1 H) 4.58 (s, 2 H) 4.15-4.24 (m, 2 H) 3.93-4.06 (m, 1 H) 3.77-3.85 (m, 2 H) 3.45-3.56 (m, 2 H) 3.07 (s, 3 H) 3.03 (br. s., 1 H) 2.86 (s, 3 H) 2.43-2.55 (m, 3H) 1.48 (m, J=12.08 Hz, 2 H)

ESI (+) MS m/z 530 (MH⁺)

ESI (+) HRMS calcd for $C_{30}H_{35}N_5O_4+H^+$: 530.2762; found 530.2769

4-(4-Methyl-4-oxy-piperazin-1-yl)-N-{6-[2-(4-trifluoromethyl-benzyloxy)-ethoxy]-1H-indazol-3-yl}-benzamide hydrochloride (Cpd. 42)

¹H-NMR (400 MHz), δ (ppm, DMSO-d₆): 12.55 (s, 1 H) 12.50 (br. s., 1 H) 10.49 (s, 1 H) 8.03 (d, J=8.97 Hz, 2 H) 7.72 (d, J=8.06 Hz, 2 H) 7.57-7.61 (m, 3 H) 7.10-7.15 (m, 2 H) 6.87 (d, J=1.83 Hz, 1 H) 6.73 (dd, J=8.88, 2.11 Hz, 1 H) 4.70 (s, 2 H) 4.21-4.25 (m, 2 H) 3.99 (d, J=14.29 Hz, 2 H) 3.75-3.89 (m, 6 H) 3.59 (s, 3 H) 3.40-3.48 (m, 2H)

ESI (+) MS m/z 570 (MH$^+$)
ESI (+) HRMS calcd for $C_{29}H_{30}F_3N_5O_4$+H$^+$: 570.2323; found 570.2330

Example 5

N-[6-(2-Benzyloxy-ethoxy)-1H-indazol-3-yl]-4-piperazin-1-yl-benzamide (Cpd. 20)

Conversion 8

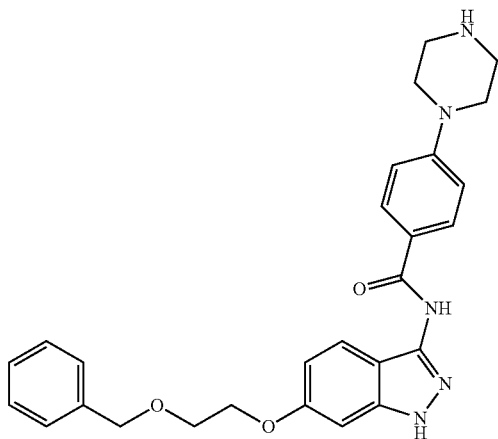 [SMILES: O=C(Nc1n[nH]c2cc(OCCOCc3ccccc3)ccc12)c1ccc(N2CCNCC2)cc1]

A solution of 4-{4-[6-(2-benzyloxy-ethoxy)-1H-indazol-3-ylcarbamoyl]-phenyl}-piperazine-1-carboxylic acid tert-butyl ester (180 mg, 0.31 mmol) in 1,4-dioxane (10 ml) and MeOH (5 ml) was treated with 4M hydrochloric acid in 1,4-dioxane (6 ml, 24 mmol). After stirring for 2 h at r.t. the reaction mixture was evaporated to dryness, diluted with water (50 ml) and brought to basic pH by addition of a saturated solution of NaHCO$_3$. The precipitated solid was filtered, washed with water, dried and purified by chromatography (Biotage SP1 Flash Purification system) on a silica gel cartridge (Biotage SNAP 25 g) using DCM as eluant A and DCM/7N NH$_3$ in MeOH 10:1 as eluant B. Elution with a gradient from A/B 100:0 to 0:100 over 15 CV, followed by an isocratic elution with eluant B (5 CV), gave a yellow solid that was triturated with diethyl ether (15 ml) affording 111 mg (yield: 75%) of the title compound as a white solid.

$^1$H-NMR (400 MHz), δ (ppm, DMSO-d$_6$): 12.44 (s, 1 H) 10.36 (s, 1 H) 7.95 (d, J=9.03 Hz, 2 H) 7.59 (d, J=9.03 Hz, 1H) 7.33-7.40 (m, 4 H) 7.25-7.32 (m, 1 H) 6.98 (d, J=9.15 Hz, 2 H) 6.85 (d, J=1.95 Hz, 1 H) 6.71 (dd, J=2.07, 8.91 Hz, 1 H) 4.58 (s, 2 H) 4.15-4.25 (m, 2 H) 3.77-3.86 (m, 2 H) 3.17-3.23 (m, 4 H) 2.78-2.86 (m, 4 H)

ESI (+) MS m/z 472 (MH$^+$)
ESI (+) HRMS calcd for $C_{27}N_5O_3H_{29}$+H$^+$: 472.2343; found 472.2327

PHARMACOLOGY

The short forms and abbreviations used herein have the following meaning:
DMSO dimethylsulfoxide
g gram
IC$_{50}$ concentration inhibiting by 50%
mg milligram
microg microgram
microL microliter
mL milliliter
mM millimolar
microM micromolar
nM nanomolar
Assays Compounds of the present invention were tested in biochemical assays, as described below.

Preparation of FLT3 and KIT Kinase Cytoplasmic Domains for use in Biochemical Assay Cloning, Expression and Purification FLT3 cytoplasmic domain (aa 564-993end of the 993 aminoacid long full length sequence, accession number P36888 of UniProtKB/Swiss-Prot. database) was amplified by PCR starting from a testis cDNA library and then cloned into pVL vector for expression in insect cells through the baculovirus system. The GST-FLT3 cytoplasmic domain has been expressed in Sf21 cells infected for 72 hours at 27° C. The recombinant protein has been purified by affinity on GSH-sepharose and eluted with glutathione. A further purification step has been performed on heparine sepharose. The final yield was of 0.5 mg/billion cells and the protein resulted >90% pure by coomassie staining.

KIT cytoplasmic domain (aa 544-976end of the 976 aminoacid long full length sequence, accession number P10721 of UniProtKB/Swiss-Prot database) was cloned into pVL vector for expression in insect cells through the baculovirus system. The GST-KIT cytoplasmic domain has been expressed in Sf21 cells infected for 66 hrs at 27° C. The recombinant protein has been purified by affinity on GSH-sepharose and eluted with glutathione. The final yield was of 9 mg/billion cells and the protein resulted >80% pure by coomassie staining.

Purified proteins were stored at −80° C. prior its use in biochemical assay.

Biochemical Assays i. General Principle—A specific peptidic substrate was trans-phosphorylated by the kinase in the presence of ATP traced with 33Pγ-ATP. At the end of the phosphorylation reaction, the not reacted ATP, cold and radioactive, was captured by an excess of dowex ion exchange resin that eventually settled by gravity to the bottom of the reaction plate. The supernatant was subsequently withdrawn and transferred into a counting plate that was then evaluated by β-counting.

ii. Dowex resin preparation—500 g of wet resin (SIGMA, custom prepared resin DOWEX 1×8 200-400 mesh, 2.5 Kg) were weighed out and diluted to 2 L in 150 mM sodium formate, pH 3.00. The resin was allowed to settle down overnight and then the supernatant was discarded. After three washes as above over a couple of days, the resin was allowed to settle and two volumes (with respect to the resin volume) were added of 150 mM sodium formate buffer.

Biochemical Assay for Inhibitors of FLT3 Kinase Activity i. Enzyme—The assay was performed using FLT3 cytoplasmic domain product and purified in house as GST fused protein. The FLT3 protein (1 microM) was pre activated with 800 microM ATP for 1 hour at 28*C in order to obtain a linear kinetic.

ii. FLT3 Kinase Buffer (KB)—Kinase buffer was composed of 50 mM HEPES pH 7.9 containing 4 mM MgCl$_2$, 1 mM DTT, 10 microM Na$_3$VO$_4$, and 0.2 mg/mL BSA iii. Assay conditions—The FLT3 kinase assay was run with a final pre activated enzyme concentration of 2 nM, in the presence of 254 microM ATP (residual ATP from KIT pre activation step is negligible), 8 nM 33P-γ-ATP and 55 microM of substrate BioDB n*24 (Aminoacidic sequence: GGKKKVSRSGLYRSPSMPENLNRPR- SEQ ID NO: 1). The peptide was purchased from American Peptide Company (Sunnyvale, Calif.).

Biochemical Assay for Inhibitors of KIT Kinase Activity i. Enzyme—The assay has been performed using KIT cytoplasmic domain product and purified in house as GST fused protein. The KIT protein (4.5 microM) was pre activated with 300 microM ATP for 1 hour at 28*C in order to obtain a linear kinetic.

ii. KIT kinase Buffer (KB)—Kinase buffer was composed of 50 mM HEPES pH 7.9 containing 5 mM $MgCl_2$, 1 mM $MnCl_2$, 10 mM DTT, 3 microM $Na_3VO_4$, and 0.2 mg/mL BSA iii. Assay conditions—The KIT kinase assay was run with a final pre activated enzyme concentration of 4 nM, in the presence of 4.4 microM ATP (residual ATP from KIT pre activation step is negligible), 3.9 nM 33P-γ-ATP and 2.5 microM of substrate BioDB n*138 (Aminoacidic sequence: KWEEINGNNYVYIDPTQLPYDHKWEF-PRNR- SEQ ID NO: 2). The peptide was purchased from American Peptide Company (Sunnyvale, Calif.).

Compound Testing i. Compound Dilution—For $IC_{50}$ determination, test compounds were received as a 1 mM solution in 100% DMSO, distributed into 96 well plates: compounds were then plated into the first column of a microtiter plate (A1 to G1), 100 microL/well. An automated station for serial dilutions (Biomek FX, Beckman) was used for producing 1:3 dilutions in 100% DMSO, from line A1 to A10, and for all the compounds in the column. Moreover, 4-5 copies of daughter plates were prepared by reformatting 5 microL of this first set of 100% DMSO dilution plates into 384 deep well-plates: one of these plates with the serial dilutions of test compounds was thawed the day of the experiments, reconstituted at a 3× concentration with water and used in the $IC_{50}$ determination assays. In a standard experiment, the highest concentration (3×) of all compounds was 30 microM, while the lowest one was 1.5 nM.

Each 384 well-plate contained at least one curve of the standard inhibitor staurosporine and reference wells (total enzyme activity vs. no enzymatic activity) for the Z' and signal to background evaluation.

ii. Assay Scheme—384-well plates, V bottom (test plates) were prepared with 5 microL of the compound dilution (3×) and then placed onto a PlateTrak 12 robotized station (Perkin Elmer; the robot had one 384-tip pipetting head for starting the assay plus one 96-tip head for dispensing the resin) together with one reservoir for the Enzyme mix (3×) and one for the ATP mix (3×). At the start of the run, the robot aspirated 5 μl of ATP mix, made an air gap inside the tips (3 microL) and aspirated 5 microL of Enzyme mix. The following dispensation into the plates plus 3 cycles of mixing, done by the robot itself, started the kinase reaction. At this point, the correct concentrations were restored for all the reagents. The robot incubated the plates for 60 minutes at r.t., and then stopped the reaction by pipetting 60 microL of dowex resin suspension into the reaction mix. In order to avoid tip clogging, wide bore tips were used to dispense the resin suspension. Three cycles of mixing were done immediately after the addition of the resin. Another mixing cycle was performed after all the plates were stopped, this time using normal tips: the plates were then allowed to rest for about one hour in order to allow resin sedimentation. At this point, 27 microL of the supernatant were transferred into 384-Optiplates (Perkin-Elmer), with 50 microL of Microscint 40 (Perkin-Elmer); after 5 min of orbital shaking the plates were read on a Perkin-Elmer Top Count radioactivity counter.

iii. Data Fitting—Data were analyzed by an internally customized version of the SW package "Assay Explorer" that provided sigmoidal fitting of the ten-dilutions curves for $IC_{50}$ determination in the secondary assays/hit confirmation routines.

Cell-Based Assays for Inhibitors of FLT3 Kinase Activity

In vitro Cell Proliferation Assay for Inhibitors of FLT3 Kinase Activity

The human acute leukemia MOLM-13 AND MV-4-11 cells, bearing a FLT3-ITD mutation, were seeded (5000 cells/well) in white 384 well-plates in complete medium (RPMI 1640 plus 10% Fetal bovine serum) and treated with compounds dissolved in 0.1% DMSO, 24 h after seeding. The cells were incubated at 37° C. and 5% $CO_2$ and after 72 h the plates were processed using CellTiter-Glo assay (Promega) following the manufacturer's instruction.

CellTiter-Glo is a homogenous method based on the quantification of the ATP present, an indicator of metabolitically active cells. ATP was quantified using a system based on luciferase and D-luciferin resultant into light generation. The luminescent signal was proportional to the number of cells present in culture.

Briefly, 25 microL/well reagent solution were added to each well and, after 5 minutes shaking, microplates were read by Envision (PerkinElmer) luminometer. Inhibitory activity was evaluated comparing treated versus control data using Symyx Assay Explorer (Symyx Technologies Inc.) program. $IC_{50}$ was calculated using sigmoidal interpolation curve. The compounds of formula (I) tested as described above, resulted to possess a remarkable FLT3 and KIT inhibitory activity, together with very good potency in inhibiting MOLM-13 AND MV-4-11 cells proliferation.

See, as an example, the following Table I, reporting the experimental data of some representative compounds of the invention being tested in biochemical assays as FLT3 and KIT kinase inhibitors ($IC_{50}$ microM), and Table II, reporting the experimental data of some representative compounds of the invention being tested in cell proliferation assays as MOLM-13 and MV-4-11 inhibitors ($IC_{50}$ microM), in comparison with the closest compound of the prior art (Ref. compound), described in WO03/028720, page 77, Table XI, entry 226, compound A02-M2-B05, having the following structure:

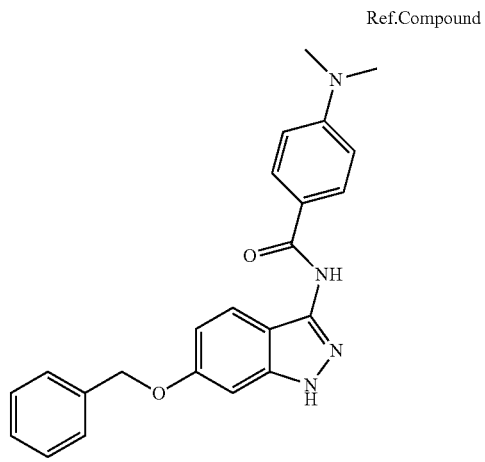 [SMILES: CN(C)c1ccc(C(=O)Nc2n[nH]c3cc(OCc4ccccc4)ccc23)cc1]

Ref.Compound

In biochemical assays, the $IC_{50}$ values are typically lower than 2 microM on FLT3 and lower than 3 microM on KIT. In cell proliferation assays, the $IC_{50}$ values are typically lower than 3 microM, with 26 compounds having $IC_{50}$ values lower than 0.1 microM on both cell lines.

TABLE I

| Cpd No. | FLT3 IC$_{50}$ (microM) Biochemical assay | KIT IC$_{50}$ (microM) Biochemical assay |
|---|---|---|
| 1 | 0.428 | 2.805 |
| 2 | 1.134 | 0.172 |
| 3 | 0.639 | 0.564 |
| 4 | 0.974 | >10 |
| 5 | 1.171 | 2.619 |
| 6 | 0.248 | 6.888 |
| 7 | 0.249 | 1.505 |
| 9 | 1.504 | 0.713 |
| 10 | <0.050 | 0.956 |
| 11 | <0.050 | 0.113 |
| 14 | <0.050 | 0.118 |
| 15 | <0.050 | 0.076 |
| 16 | <0.050 | 0.106 |
| 17 | 0.062 | 0.146 |
| 18 | 0.414 | 1.392 |
| 19 | <0.050 | 0.061 |
| 20 | <0.050 | 0.052 |
| 21 | 0.104 | 0.134 |
| 22 | 0.056 | 0.055 |
| 23 | <0.050 | 0.109 |
| 24 | 0.162 | 0.260 |
| 25 | 0.074 | 0.197 |
| 26 | 0.090 | 0.124 |
| 27 | <0.050 | 0.091 |
| 28 | 0.136 | 0.306 |
| 29 | 0.635 | 1.078 |
| 30 | 0.166 | 1.405 |
| 32 | <0.050 | <0.050 |
| 33 | <0.050 | <0.050 |
| 34 | 0.056 | 0.058 |
| 35 | 1.176 | 2.370 |
| 38 | 0.539 | 0.613 |
| 39 | 0.062 | 0.528 |
| 40 | <0.050 | 0.088 |
| 41 | 0.052 | 0.180 |
| 42 | <0.050 | 0.055 |
| Ref. Compound | 3.175 | >10 |

TABLE II

| Cpd No. | MOLM-13 IC$_{50}$ (microM) Cell proliferation assay | MV-4-11 IC$_{50}$ (microM) Cell proliferation assay |
|---|---|---|
| 1 | 0.789 | 0.683 |
| 2 | 1.158 | 1.475 |
| 3 | 0.990 | 0.987 |
| 4 | 0.092 | <0.050 |
| 5 | 0.557 | 0.513 |
| 6 | 0.673 | 0.163 |
| 7 | 0.240 | 0.110 |
| 8 | 1.978 | 2.753 |
| 9 | 0.245 | 0.101 |
| 10 | 0.139 | 0.118 |
| 11 | <0.050 | <0.050 |
| 14 | <0.050 | <0.050 |
| 15 | <0.050 | <0.050 |
| 16 | <0.050 | <0.050 |
| 17 | 0.087 | <0.050 |
| 19 | <0.050 | <0.050 |
| 20 | <0.050 | <0.050 |
| 21 | 0.068 | <0.050 |
| 22 | 0.065 | <0.050 |
| 23 | <0.050 | <0.050 |
| 24 | <0.050 | <0.050 |
| 25 | <0.050 | <0.050 |
| 26 | <0.050 | <0.050 |
| 27 | <0.050 | <0.050 |
| 28 | <0.050 | <0.050 |
| 29 | <0.050 | <0.050 |
| 30 | <0.050 | <0.050 |
| 32 | <0.050 | <0.050 |
| 33 | <0.050 | <0.050 |
| 34 | <0.050 | <0.050 |
| 35 | <0.050 | <0.050 |
| 38 | <0.050 | <0.050 |
| 39 | 0.081 | 0.050 |
| 40 | <0.050 | <0.050 |
| 41 | <0.050 | <0.050 |
| 43 | 0.240 | 0.118 |
| Ref. Compound | 3.911 | 5.537 |

The invention claimed is:

1. A compound of formula (I):

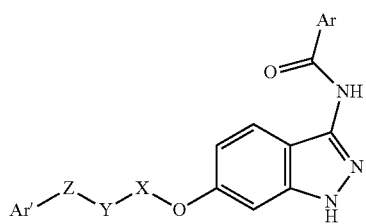

wherein:

Ar is a group selected from

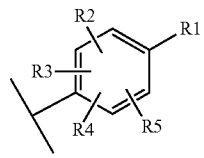 Ar1

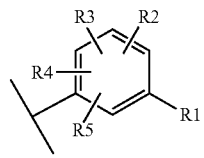 Ar2

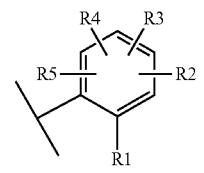 Ar3 wherein:

R1 is an optionally substituted heterocyclyl;

R2, R3, R4 and R5 are independently hydrogen, halogen, nitro, cyano, $SO_nR9$, COR10, NR11R12, OR13 or an optionally substituted group selected from straight or branched $C_1$-$C_6$ alkyl, straight or branched $C_2$-$C_6$ alkenyl, straight or branched $C_2$-$C_6$ alkynyl, and $C_3$-$C_6$ cycloalkyl wherein:

R9 is NR11R12 or an optionally substituted group selected from straight or branched $C_1$-$C_6$ alkyl, straight or branched $C_2$-$C_6$ alkenyl, straight or branched $C_2$-$C_6$ alkynyl, $C_3$-$C_6$ cycloalkyl, heterocyclyl, aryl and heteroaryl;

R10 is hydrogen, NR11R12, OR13 or an optionally substituted group selected from straight or branched $C_1$-$C_6$ alkyl, straight or branched $C_2$-$C_6$ alkenyl, straight or branched $C_2$-$C_6$ alkynyl, $C_3$-$C_6$ cycloalkyl, heterocyclyl, aryl and heteroaryl;

R11 and R12, taken together with the nitrogen atom to which they are bound, may form an optionally substituted heterocyclyl group;

R13 is hydrogen, COR10 or an optionally substituted group selected from straight or branched $C_1$-$C_6$ alkyl, straight or branched $C_2$-$C_6$ alkenyl, straight or branched $C_2$-$C_6$ alkynyl, $C_3$-$C_6$ cycloalkyl, heterocyclyl, aryl and heteroaryl, wherein R10 is as defined above;

n is 0, 1 or 2;

X is an optionally substituted straight or branched $C_1$-$C_6$ alkyl;

Y is a bond or oxygen;

Z is an optionally substituted straight or branched $C_1$-$C_6$ alkyl;

Ar' is an optionally substituted aryl or an optionally substituted heteroaryl;

or a pharmaceutically acceptable salt thereof.

2. The compound of formula (I) as defined in claim 1 wherein:

Ar is Ar1 or Ar2; and R2, R3, R4, R5 are each independently hydrogen, halogen, NR11R12 or OR13, wherein R11, R12 and R13 are as defined in claim 1.

3. A compound of formula (I) or a pharmaceutically acceptable salt thereof as defined in claim 1 which is selected from the group consisting of:

N-[6-(2-Benzyloxy-ethoxy)-1H-indazol-3-yl]-4-(4-methyl-piperazin-1-yl)-benzamide, N-[6-(2-Benzyloxy-ethoxy)-1H-indazol-3-yl]-4-(4-methyl-4-oxy-piperazin-1-yl)-benzamide, N-[6-(2-Benzyloxy-ethoxy)-1H-indazol-3-yl]-4-(4-dimethylamino-piperidin-1-yl)-benzamide, 4-{4-[6-(2-Benzyloxy-ethoxy)-1H-indazol-3-ylcarbamoyl]-phenyl}-piperazine-1-carboxylic acid tert-butyl ester, N-[6-(2-Benzyloxy-ethoxy)-1H-indazol-3-yl]-4-piperazin-1-yl-benzamide, N-[6-(2-Benzyloxy-ethoxy)-1H-indazol-3-yl]-4-morpholin-4-yl-benzamide, N-[6-(2-Benzyloxy-ethoxy)-1H-indazol-3-yl]-4-(3-pyrrolidin-1-yl-azetidin-1-yl)-benzamide, N-[6-(2-Benzyloxy-ethoxy)-1H-indazol-3-yl]-3-(4-methyl-piperazin-1-yl)-benzamide, N-{6[2-(2-Fluoro-benzyloxy)-ethoxy]-1H-indazol-3-yl)}-4-(4-methyl-piperazin-1-yl)-benzamide, N-{6[2-(3-Fluoro-benzyloxy)-ethoxy]-1H-indazol-3-yl}-4-(4-methyl-piperazin-1-yl)-benzamide, N-{6-[2-(4-Fluoro-benzyloxy)-ethoxy]-1H-indazol-3-yl]-4-(4-methyl-piperazin-1-yl)-benzamide, 4-(4-Methyl-piperazin-1-yl)-N-{6[2-(4-trifluoromethyl-benzyloxy)-ethoxy]-1H-indazol-3-yl}-benzamide, 4-(4-Methyl-piperazin-1-yl)-N-{6-[2-(3-trifluoromethyl-benzyloxy)-ethoxy]-1H-indazol-3-yl}-benzamide, 4-(4-Methyl-piperazin-1-yl)-N-{6-[2-(pyridin-4-yl-methoxy)-ethoxy]-1H-indazol-3-yl}-benzamide, 4-(4-Methyl-piperazin-1-yl)-N-{6-[2-(pyridin-3-yl-methoxy)-ethoxy]-1H-indazol-3-yl}-benzamide, 4-(4-Methyl-piperazin-1-yl)-N-{6-[2-(pyridin-2-yl-methoxy)-ethoxy]-1H-indazol-3-yl}-benzamide, N-[6-(2-Benzyloxy-ethoxy)-1H-indazol-3-yl]-2-fluoro-4-(4-methyl-piperazin-1-yl)-benzamide, N-{6-[2-(4-Methoxy-benzyloxy)-ethoxy]-1H-indazol-3-yl}-4-(4-methyl-piperazin-1-yl)-benzamide, and 4-(4-Methyl-4-oxy-piperazin-1-yl)-N-{6-[2-(4-trifluoromethyl-benzyloxy)-ethoxy]-1H-indazol-3-yl}-benzamide.

4. A pharmaceutical composition comprising a therapeutically effective amount of a compound of formula (I) or a pharmaceutically acceptable salt thereof, as defined in claim 1, and at least one pharmaceutically acceptable excipient, carrier and/or diluent.

5. A pharmaceutical composition according to claim 4 further comprising one or more chemotherapeutic agents.

6. A product comprising a compound of formula (I) or a pharmaceutically acceptable salt thereof, as defined in claim 1, and one or more chemotherapeutic agents, as a combined preparation for simultaneous, separate or sequential use in anticancer therapy.

\* \* \* \* \*